(12) United States Patent
Kolter et al.

(10) Patent No.: US 9,131,687 B2
(45) Date of Patent: Sep. 15, 2015

(54) ROSEOBACTICIDES AND USES THEREOF

(75) Inventors: Roberto Kolter, Cambridge, MA (US);
Rebecca Case, Edmonton, CA (US);
Jon Clardy, Jamaica Plain, MA (US);
Mohammad Seyedsayamdost, Newton, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 13/817,839

(22) PCT Filed: Aug. 22, 2011

(86) PCT No.: PCT/US2011/048628
§ 371 (c)(1),
(2), (4) Date: Jun. 3, 2013

(87) PCT Pub. No.: WO2012/033631
PCT Pub. Date: Mar. 15, 2012

(65) Prior Publication Data
US 2013/0252815 A1    Sep. 26, 2013

Related U.S. Application Data

(60) Provisional application No. 61/375,315, filed on Aug. 20, 2010.

(51) Int. Cl.
*A01N 43/38* (2006.01)
*A01N 43/12* (2006.01)
*A01N 63/02* (2006.01)
*C07D 307/93* (2006.01)
*C07D 405/04* (2006.01)
*C07D 405/14* (2006.01)

(52) U.S. Cl.
CPC ............... *A01N 43/38* (2013.01); *A01N 43/12* (2013.01); *A01N 63/02* (2013.01); *C07D 307/93* (2013.01); *C07D 405/04* (2013.01); *C07D 405/14* (2013.01)

(58) Field of Classification Search
CPC ....... A01N 43/12; A01N 43/38; A01N 63/02; A01P 13/00; C07D 307/93; C07D 405/04; C07D 405/14; C07D 407/12

USPC ................. 504/118, 129, 140, 141, 189, 298; 549/200, 429, 462, 466; 514/183, 421, 514/443, 444, 445, 470; 424/405, 93.3, 424/780; 106/18.33, 18.34; 523/122
See application file for complete search history.

(56) References Cited

U.S. PATENT DOCUMENTS

| | | | |
|---|---|---|---|
| 2,688,583 A | 9/1954 | Darragh et al. |
| 2,692,231 A | 10/1954 | Stayner et al. |
| 2,734,028 A | 2/1956 | Domogalla |
| 3,702,298 A | 11/1972 | Zsoldos et al. |
| 6,004,543 A | 12/1999 | Galey |
| 7,022,317 B2 | 4/2006 | Erdelmeier et al. |

FOREIGN PATENT DOCUMENTS

JP     06-306032     11/1994

OTHER PUBLICATIONS

U.S. Patent and Trademark Office, 2014 Interim Guidance on Patent Subject Matter Eligibility, 2014, 79 Fed. Reg. 74618.*
Seyedsayamdost et al., "The Jekyll- and-Hyde chemistry of Phaeobacter gallaeciensis", 2011, Nature Chemistry, Advance Online Publication, www.nature.com/naturechemistry, DOI : 10.1038/NCHEM.1002, pp. 1-5.*
Seyedsayamdost et al., J Am Chem Soc, 133:18343-18349 (2011). "Roseobacticides: small molecule modulators of an algal-bacterial symbiosis."
Seyedsayamdost et al., Nature Chemistry, Advance Online Publication DOI: 10.1038/NCHEM.1002, published online Feb. 27, 2011. "The Jekyll- and-Hyde chemistry of Phaeobacter gallaeciensis."

* cited by examiner

*Primary Examiner* — Jane C Osweki
(74) *Attorney, Agent, or Firm* — Nixon Peabody LLP; David S. Resnick

(57) ABSTRACT

Embodiments of the invention relate to compounds and methods for controlling algal growth, for example, in bodies of water or surfaces exposed to algae. Provided are compounds having algicidal activities and methods of use of these compounds as well as formulations and compositions comprising the compound having algicidal activities.

15 Claims, 45 Drawing Sheets

R=OH, ROSEOBACTICIDE A, 6
R=H, ROSEOBACTICIDE B, 7

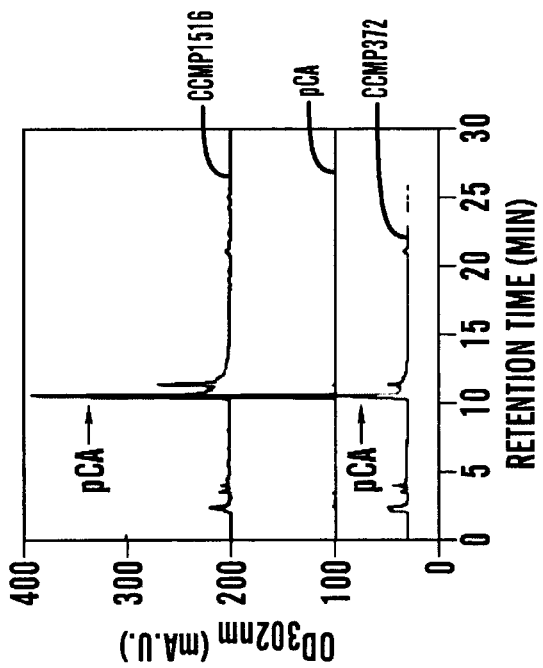
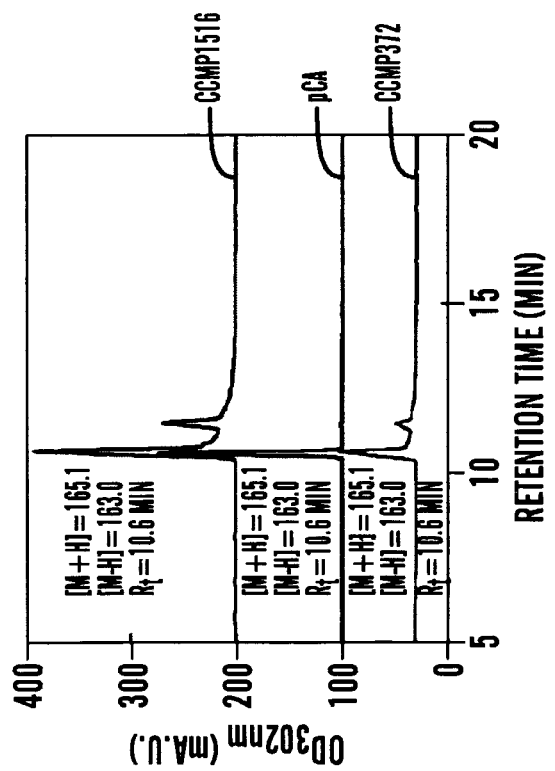
FIG. 12C
FIG. 12A p-coumaric ACID (14) $R^1=R^3=H, R^2=OH$

SINAPIC ACID (15) $R^1=R^3=OCH_3, R^2=OH$

FERULIC ACID (16) $R^1=OCH_3, R^2=OH, R^3=H$

CINNAMIC ACID (17) $R^1=R^2=R^3=H$

CAFFEIC ACID (18) $R^1=R^2=OH, R^3=H$

ROSEOBACTICIDES AND USES THEREOF

GOVERNMENT SUPPORT

This invention was made with Government support under Grant Nos.: R01 GM082137, GM086258, and AI057159 awarded by the National Institutes of Health, and under Grant No: N000141010447 awarded by the Office of Naval Research. The Government has certain rights in the invention.

CROSS-REFERENCE TO RELATED APPLICATIONS

This application is a 35 U.S.C. §371 National Phase Entry Application of International Application No. PCT/US2011/048628 filed Aug. 22, 2011, which designates the U.S., and which claims benefit under 35 U.S.C. §119(e) of U.S. Provisional Patent Application Ser. No. 61/375,315 filed Aug. 20, 2010, the contents of which are hereby incorporated by reference in their entireties.

BACKGROUND

Undesired and/or uncontrolled algal bloom is a constant problem in bodies of water such as swimming pools, aquaculture ponds, freshwater ponds, aquariums, urban drainage systems, industrial cooling water systems and even in the vast ocean. Such algal blooms, if left unchecked, can multiply to the point of rendering the water unfit for human use. For example, filamentous algae, or commonly referred to as "pond scum" or "pond moss" forms greenish mats upon the water's surface. The stringy, fast-growing algae can cover a pond with slimy, lime-green clumps or mats in a short period of time. Some common types of problematic filamentous algae are of the genera *Spirogyra, Cladophora* and *Pithophora*. Algal blooms of the toxic algae such as dinoflagellates of the genus *Alexandrium* and *Karenia* occur worldwide on a regular basis and threatening people's access to food (e.g., fish and shellfishes) and their livelihoods. These toxic algae produce potent toxins given the right conditions. Algal blooms can cause harm through the production of toxins or by their accumulated biomass, which can affect co-occurring organisms, e.g., fishes that feed on them, and alter food-web dynamics. Impacts include human illness and mortality following consumption of or indirect exposure to the harmful algal bloom toxins, substantial economic losses to coastal communities and commercial fisheries, and algal bloom-associated fish, bird and mammal mortalities. To the human eye, such blooms can appear greenish, brown, and even reddish-orange depending upon the algal species, the aquatic ecosystem, and the concentration of the organisms. When the bloom takes on a red or brown hue, it is known colloquially as a red tide.

Various strategies have been used to control algal blooms. Early attempts to solve this problem have included the use of active chlorine, copper-containing compounds or quaternary ammonium salts. Natural algicides (or "algaecides") such as barley straws are also used. In England, barley straws are placed in mesh bags and floated in fish ponds or water gardens to help reduce algal growth without harming pond plants and animals. Herbicides are used on a regular basis to control any unwanted aquatic vegetation and to prevent fouling of aquaculture cages. However, this has led to the development of herbicide resistant algae, e.g., *Pithophora*. Synthetic algicides include copper sulphate, chromate-based compounds and n-alkyl-dimethyl benzyl ammonium chloride (e.g., Polyquat and Clorox) which are very toxic and environmentally hazardous. Active chlorine-containing compounds also have other serious drawbacks including rapid decomposition, pungent odor and corrosive action of water handling systems.

Copper compounds, such as copper sulfate, copper carbonate and other related copper salts tend to exert algaecidic activity only at relatively high concentrations making use of such compounds expensive. Copper salts, such as copper sulfate, also have a tendency to precipitate from aqueous solutions containing carbonates and bicarbonates. U.S. Pat. No. 2,734,028 to Domogalla attempts to solve this problem of copper precipitation by the inclusion of an hydroxyamine, such as alkanolamine, as a solubilizing agent to maintain the copper cation in solution in a variety of hard water systems or in water having large amounts of dissolved carbon dioxide.

Quaternary ammonium compounds have also been proposed as algaecides and bactericides. Their bactericidal power has been attributed to the tensio-active effect and the formation of compounds between quaternary ammonium salts and proteins. These compounds, however, have been known to irritate human skin and to loose activity in the presence of hard, calcium-containing water. Stayner et al., U.S. Pat. No. 2,692,231, indicate that quaternary ammonium salts, such as alkyl dimethyl benzyl ammonium chlorides by themselves are inadequate under certain circumstances. Their attempted solution is to combine the quaternary ammonium salt with a nonanionic organic material having a water solubility of less than about 5%. The nonanionic organic material is characterized as being hydrophobic-weakly hydrophilic species and as a promoter for the quaternary ammonium salt enhancing the microbicidal effect of the quaternary ammonium compound.

Darragh et al., U.S. Pat. No. 2,688,583, disclose that quaternary ammonium salts have the further drawback of producing a cloudy dispersion upon being added to water. Their solution to this problem is to include with the quaternary ammonium salt an inorganic water soluble aluminum salt capable of producing clear aqueous dispersions throughout a range of concentrations. Aluminum sulfate or aluminum chloride has been employed in this capacity.

Zsoldos et al., U.S. Pat. No. 3,702,298, have attempted to control the growth of micro-organisms in water by maintaining a highly oxidizing alkaline aqueous solution consisting of an oxidizer bank of a large excess of peroxy compounds in combination with copper or silver salts (such as nitrate or sulfate salts) acting as an in situ catalyst. Optionally, a chelating agent, such as sodium citrate or acetate, can be employed to prevent precipitation of the metal catalyst.

SUMMARY OF INVENTION

Embodiments of the invention relate to compounds and methods for controlling algal growth.

In some embodiments, provided herein is a compound comprising a formula I:

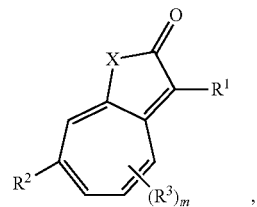

FORMULA (I)

$R^1$ is optionally substituted aryl, optionally substituted heteroaryl, optionally substituted phenyl or an optionally substitute indole.

A preferred substituted phenyl is

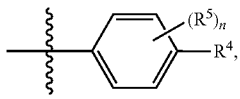

wherein $R^4$ is H, $OR^6$, $SR^6$, halogen, CN, $CF_3$, $N(R^6)_2$, $NO_2$, optionally substituted alkyl, optionally substituted alkenyl, or optionally substituted alkynyl; n is 0, 1, 2, 3, or 4; and $R^5$ is $OR^6$, $SR^6$, $SSR^6$, halogen, CN, $CF_3$, $N(R^6)_2$, $NO_2$, optionally substituted alkyl, optionally substituted alkenyl, or optionally substituted alkynyl. Preferably, $R^4$ is H or $OR^6$. More preferably $R^4$ is H, OH, or OMe.

In some embodiments, n is 0.

In some embodiments, $R^4$ is

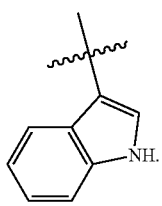

$R^2$ is $OR^7$, $SR^7$, $SO_2R^7$, $SSR^7$, wherein $R^7$ is H, optionally substituted alkyl, optionally substituted alkenyl, optionally substituted alkynyl, optionally substituted acyl, optionally substituted aryl or formula (I).

In some embodiments, $R^7$ is H, methyl, ethyl, propyl, butyl, pentyl, or hexyl. In some embodiments, $R^7$ is an optionally substituted arylcarbonyl. One exemplary optionally substituted arylcarbonyl is

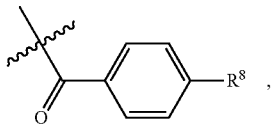

wherein $R^8$ is H, $OR^6$, $SR^6$, halogen, CN, $CF_3$, $N(R^6)_2$, $NO_2$, optionally substituted alkyl, optionally substituted alkenyl, or optionally substituted alkynyl.

In some embodiments, m is 0, 1, 2, 3, or 4, and $R^3$ is $OR^6$, $SR^6$, $SSR^6$, halogen, CN, $N(R^6)_2$, $NO_2$, optionally substituted alkyl, optionally substituted alkenyl, or optionally substituted alkynyl. In some embodiments, m is 1.

In some embodiments, $R^3$ is $OR^6$, $SR^6$, $SSR^6$. $R^6$ is H, optionally substituted alkyl, optionally substituted alkenyl, optionally substituted alkynyl, optionally substituted acyl. Preferred alkyls for $R^6$ include methyl, ethyl, propyl, butyl, pentyl, and hexyl. Preferred $R^6$ groups for $R^3$ include H, methyl, ethyl, propyl, butyl, pentyl, and hexyl.

In some embodiments, m is 1 and $R^3$ is OH, SH, or SSH.

X is O, S, $NR^6$. Preferably X is O.

In some embodiments, $R^7$ is

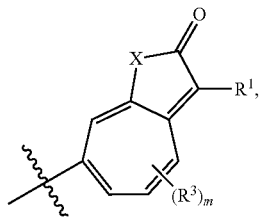

with variables $R^1$, $R^3$, and X as defined for formula (I) herein.

In some embodiments, $R^1$ is phenyl. In some embodiments, R4 is H, $R^2$ is SH, X is O, and m=0. In some embodiments, $R^1$ is substituted phenyl wherein n=0, $R^4$ is OH, $R^2$ is SH, X is O, and m=0.

In one preferred embodiment, $R^1$ is a substituted phenyl, $R^4$ is H, X is O, $R^2$ is SH, and n and m are both 0. The compound having the formula I of this preferred embodiment is Roseobacticide B.

In another preferred embodiment, $R^1$ group is a substituted phenyl, $R^4$ is OH, X is O, $R^2$ is SH, and n and m are both 0. The compound having the formula I of this preferred embodiment is Roseobacticide A.

In some embodiments, compound of formula (I) is selected from the group consisting of Roseobacticide A

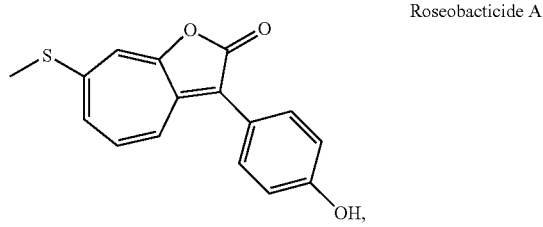

Roseobacticide B

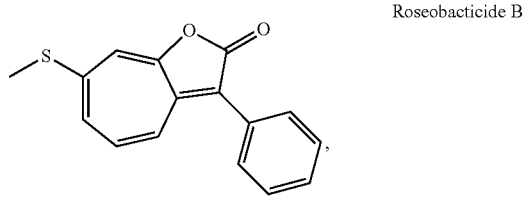

Roseobacticide C

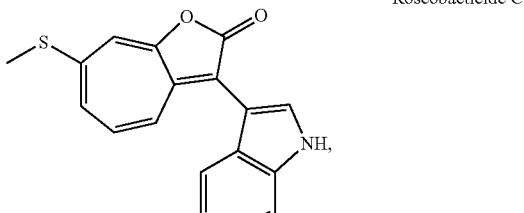

Roseobacticide D

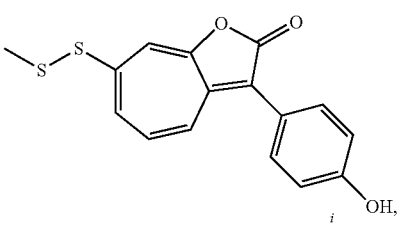

Roseobacticide E
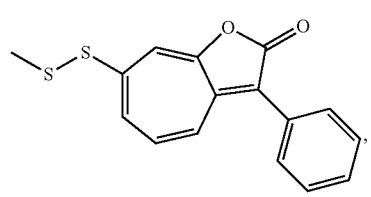
Roseobacticide F
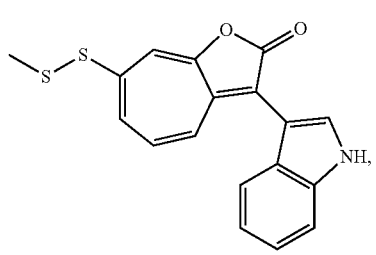
Roseobacticide G
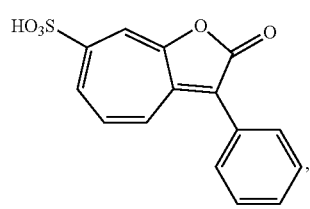
Roseobacticide H
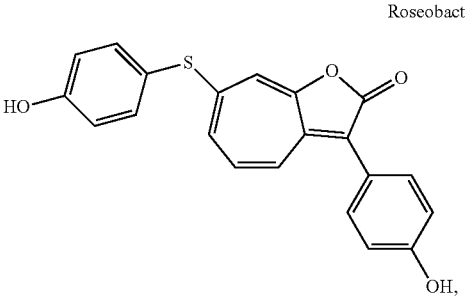
Roseobacticide I
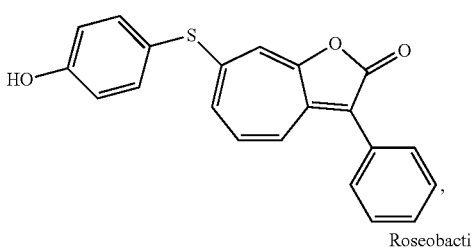
Roseobacticide J
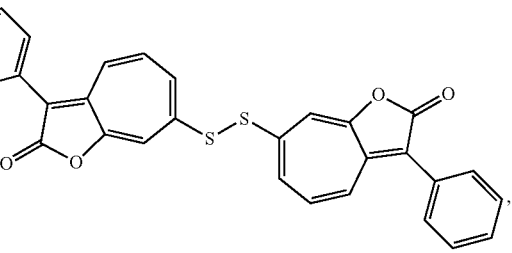
Roseobacticide K
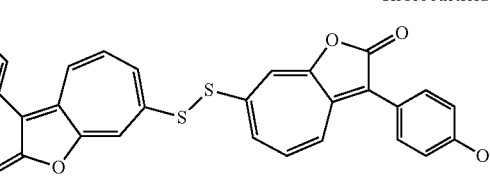
Roseobacticide L
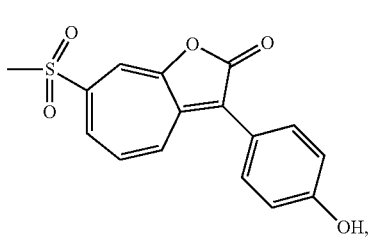
Roseobacticide M
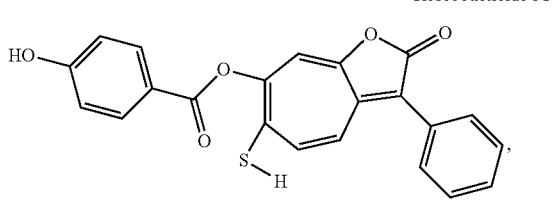
Roseobacticide N
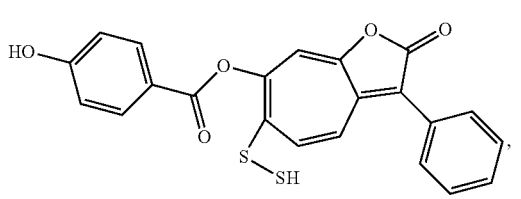
Roseobacticide O
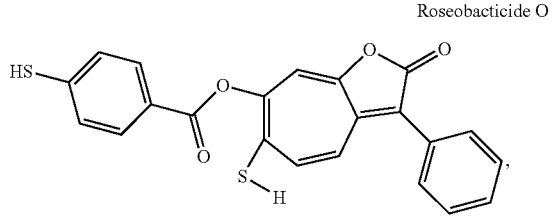
Roseobacticide P
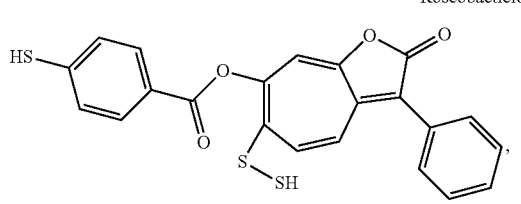
Roseobacticide Q
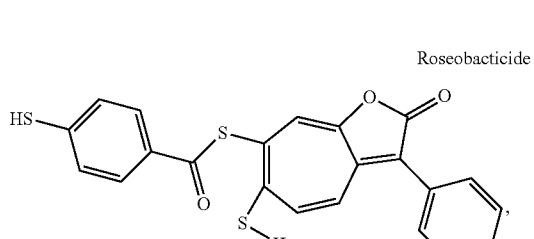
Roseobacticide R
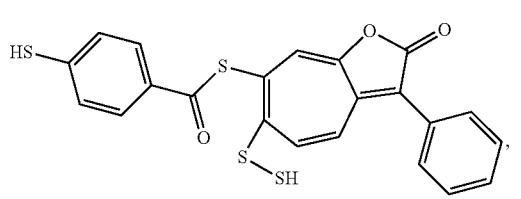

Roseobacticide S

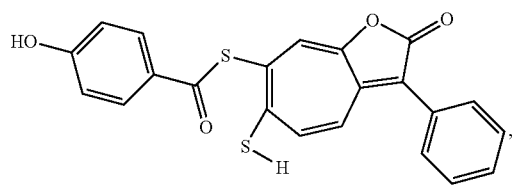

Roseobacticide T

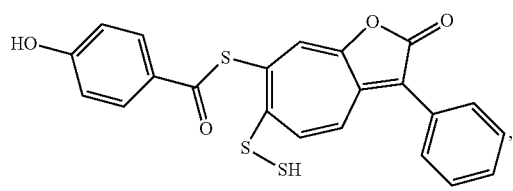

Roseobacticide U

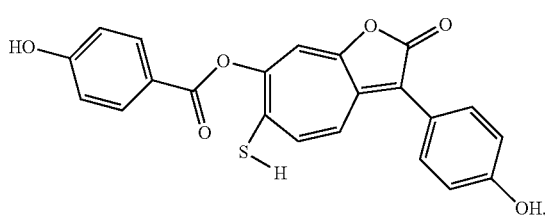

Roseobacticide V

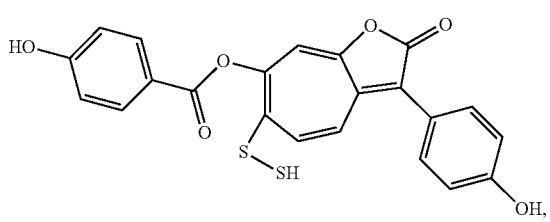

Roseobacticide W

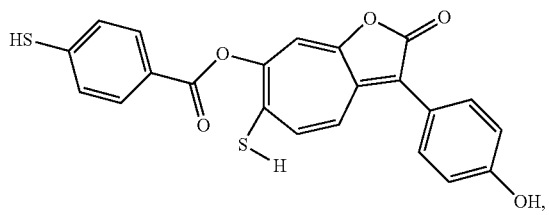

Roseobacticide X

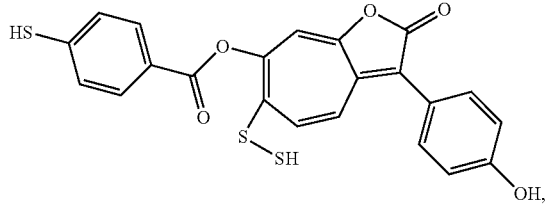

Roseobacticide Y

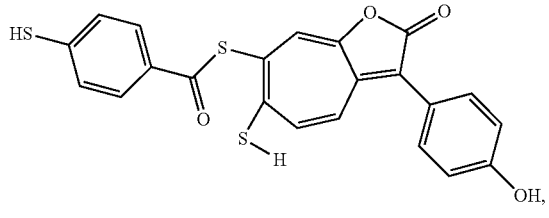

Roseobacticide Z

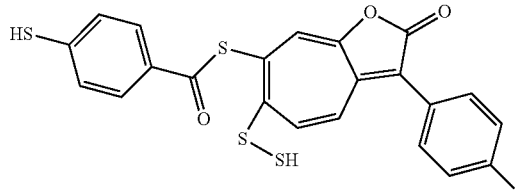

Roseobacticide AA

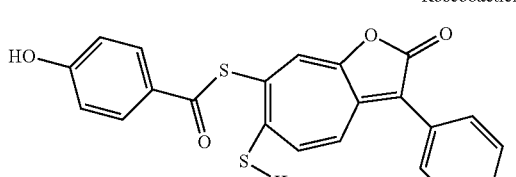

Roseobacticide BB

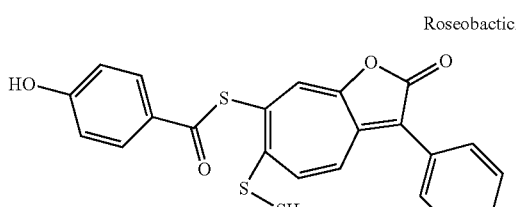

Roseobacticide CC

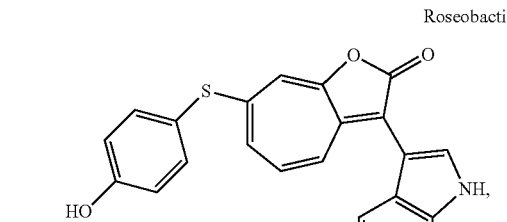

Roseobacticide DD

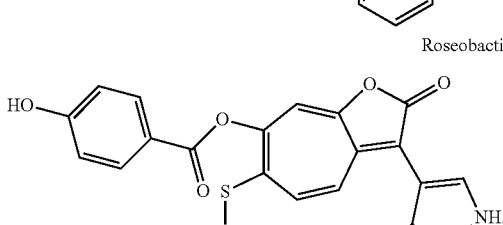

Roseobacticide EE

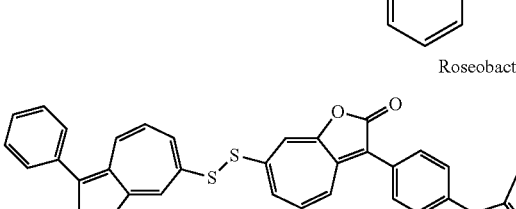

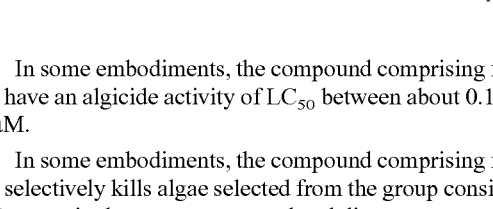

In some embodiments, the compound comprising formula I have an algicide activity of $LC_{50}$ between about 0.1 μM-35 μM.

In some embodiments, the compound comprising formula I selectively kills algae selected from the group consisting of Prymnesiophytes, cryptomonad and diatoms.

In some embodiments, the invention provides for methods of controlling algal growth in bodies of water, the method comprising adding to the water a sufficient amount of a compound comprising formula I or a salt thereof to inhibit the growth of algae in the water. Examples of bodies of water include but are not limited to swimming pools, aquaculture ponds, freshwater ponds, aquariums, urban drainage systems, industrial cooling water systems.

In some embodiments, the invention provides for methods for protecting an industrial product against infestation and destruction by algae, cyanobacteria and other photoautotrope microorganisms, the method comprising incorporating in the industrial product an effective amount of a compound of comprising formula I or a salt thereof to kill and/or prevent algae growth.

In some embodiments, the invention provides for a material or industrial product comprising a compound, composition and/or formulation comprising formula I, wherein the compound, composition and/or formulation is applied thereon or is incorporated within. The material or industrial product is selected from the group consisting of paints, polyvinyl chloride-containing plastics, varnishes, sealing materials, textile finishes, synthetic resin rendering, wood finishes and coatings, and roof tile coatings.

In some embodiments, the compound comprising formula I or a salt thereof is about 0.001 to 99% by weight when added to the body of water. In some embodiments, the compound comprising formula I or a salt thereof is from 5 to 50% by weight. More preferably, from 0.01 to 20% by weight.

In some embodiments, the concentration of compound comprising formula I or a salt thereof when used in controlling algal growth is between about 0.001 to 10 parts per million (ppm) in the water. In other embodiments, the concentration is between about 0.025 to 10 ppm, between about 0.1 to 10 ppm, between about 0.025 to 3 ppm or between about 0.1 to 3 ppm.

In some embodiments, the amount of a compound comprising formula I or a salt thereof used is sufficient to kill the algae present in the water. In some embodiments, the amount of a compound comprising formula I or a salt thereof used is sufficient to inhibit growth of algae for three consecutive days. In some embodiments, the amount of a compound comprising formula I or a salt thereof used is sufficient to inhibit growth of algae for one or more consecutive days, e.g., for one or more days, or for two or more days, or for three or more days, or for four or more days.

In some embodiments, the compound comprising formula I or a salt thereof is used in combination with other compounds, e.g., other algicides, herbicides, and other anti-microbial growth, such as fungal and bacterial growth.

BRIEF DESCRIPTION OF THE DRAWINGS

FIGS. 12A-12D demonstrate that *E. huxleyi* produces p-coumaric acid. FIG. 12A depicts the HPLC-MS profiles of commercially available pCA (middle trace) and extracts from *E. huxleyi* CCMP1516 (top trace) and *E. huxleyi* CCMP372 (bottom trace). For each peak, the retention time (Rt) and the associated mass ions in positive and negative detection modes are shown ($pCA_{MW}$=164 Da). Quantitation of pCA from two independent measurements yields a bulk solution concentration of 25±11 μM and 11±5 μM for CCMP1516 and CCMP372, respectively. FIG. 12B depicts the UV-vis spectra of the main peaks in FIG. 12A for pCA (middle trace), CCMP1516 (top trace) and CCMP372 (bottom trace). FIGS. 12C-12D depict the entire elution profile of *E. huxleyi* extracts monitored at 302 nm (FIG. 12C, pCA=middle trace; CCMP372=bottom trace; CMMP1516=top trace) and 280 nm (FIG. 12D, CCMP372=bottom trace; CCMP1516=top trace).

FIG. 20A depicts the profiles of extracts of *P. gallaeciensis* BS107 cultures grown in the absence (bottom trace) or presence of 1 mM pCA (top trace). FIG. 20B depicts the profiles of extracts of *P. gallaeciensis* BS107 cultures grown in the presence of cinnamic acid (bottom trace), and profile of purified roseobacticides A (6), B (7), C (19) and E (21) (top trace). FIG. 20C depicts the profiles of extracts of *P. gallaeciensis* BS107 cultures grown in the absence (second trace from bottom) or presence of 1 mM ferulic acid (third trace from bottom) or 1 mM sinapic acid (top trace). A profile of purified roseobacticides A (6), B (7), C (19), E (21), and J (26) is also shown (bottom trace).

FIG. 25A depicts HPLC-MS trace of roseobacticide E (21) before (top trace) and after reaction with DTT (middle trace), and extracted MS trace for the [M+H]+ ion of 28 (bottom trace)—see FIG. 18. FIG. 25B depicts UV-vis spectrum of 28 resulting from reduction of roseobacticide E. FIG. 25C depicts HPLC-MS trace of roseobacticide J (26) before (top trace) and after reaction with DTT (middle trace), and extracted MS trace for the [M+H]+ ion of 28 (bottom trace)—see FIG. 18. FIG. 25D depicts UV-vis spectrum of 28 resulting from reduction of roseobacticide J.

DETAILED DESCRIPTION OF THE INVENTION

Figure 1A:
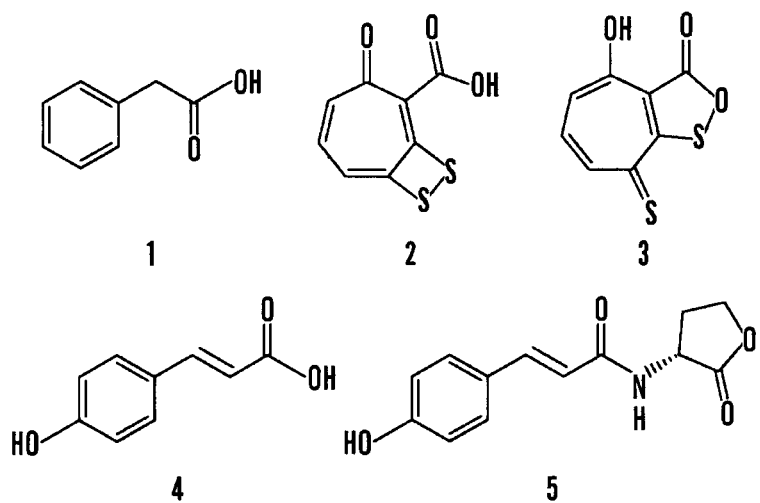
FIG. 1A shows structures of a phenylacetic acid (1), the potent broad spectrum antibotic TDA (2), and its valence tautomer thiotropocin (3) produced by *Phaeobacter gallaeciensis*; the structure of the lignin breakdown product p-coumaric acid, pCA (4) and the secondary metabolite p-coumaroyl-homoserine lactone, pCA-HSL (5).

Embodiments of the invention relate to compounds having algicidal activities and methods of use of these compounds as well as formulations and compositions comprising the compound having algicidal activities. For example, in some embodiments of the invention relates to a method of controlling algal growth in bodies of water; the compound having algicidal activities is used to treat the water, to kill the algae and/or inhibit further growth of algae in the water. Examples of bodies of water include but are not limited to swimming pools, aquaculture ponds, freshwater ponds, aquariums, urban drainage systems, industrial cooling water systems. Such uses can protect bodies of water against infestation and destruction by uncontrolled algal bloom. In some embodiments, the invention relates to methods of incorporating the compounds within and/or on surfaces, such as, into paints, varnish, plastics etc, to prevent growth of algae on building materials, industrial machines and structures that are continually being exposed to algae.

Embodiments of the present invention are based on the discovery of compounds produced by the *Roseobacter* genus strain *Phaeobacter gallaeciensis* BS107 bacteria (formerly named *Roseobacter gallaeciensis*). By way of non-limiting example, two compounds, named herein as Roseobacticide A and Roseobacticide B, both have anti-algal or algicidal activity in that they can cause algae to lyse. The algicidal activity is with an $LC_{50}$ range of 0.10 µM to 35 µM depending on the type of alga. Therefore, Roseobacticide A and Roseobacticide B are potent and specific algicides, and can be used for controlling algal growth.

As used herein, the term "an algaecide" or "an algicide" is a substance used for killing algae, e.g., by causing the lysis of algae. In some embodiments, "an algaecide" or "an algicide" is a substance that halts, inhibits and prevents further growth of algae.

As used herein, in some embodiments, the term "kill" can include lysing the algae. In some embodiments, the term "kill" refers to preventing or halting the growth of algae.

In some embodiments, "further growth of algae" refers to the increase in size, mass and/or weight when the alga is a multi-cellular organism; or an increase in cell number or cell density owing to cell division of the algae when the reference algae is a unicellular organism.

As used herein, the phrase "a compound having an algicidal activity" refers to a compound having the ability to kill alga with an $LC_{50}$ of at least <0.1 mM. In some embodiments, "a compound having an algicidal activity" refers to a compound that halts, inhibits and/or prevents further growth of algae.

As used herein, the term "Phaeobacticide" and "Roseobacticide" are used interchangeably.

The term "alkyl" refers to saturated non-aromatic hydrocarbon chains that may be a straight chain or branched chain, containing the indicated number of carbon atoms, which may be optionally inserted with N, O, or S. For example, C1-C20 indicates that the group may have from 1 to 20 (inclusive) carbon atoms in it. Preferred alkyl includes linear or branched C1-C10 alkyls. Some exemplary alkyls include, but are not limited to, methyl, ethyl, propyl, n-butyl, t-butyl, pentyl, and hexyl.

The term "alkenyl" refers to alkyl groups having at least one double bond. The term "alkynyl" refers to alkyl groups having at least one triple bind. Some exemplary C2-C6 alkenyls include, but are not limited to, ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, and 5-hexenyl.

The term "substituted" means that a hydrogen is replaced by a substituent group in the substituted entity. Suitable substituents include, without limitation, halo, hydroxy, oxo, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

The term "alkoxy" refers to an —O-alkyl radical.

The term "alkylamine" refers to an alkyl substituted with an amino.

The term "mercapto" refers to an —SH radical. The term "thioalkoxy" refers to an —S-alkyl radical.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like.

The term "arylalkyl" or the term "aralkyl" refers to alkyl substituted with an aryl.

The term "arylalkoxy" refers to an alkoxy substituted with aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heteroarylalkyl" or the term "heteroaralkyl" refers to an alkyl substituted with a heteroaryl.

The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "halogen" or "halo" refers to Br, Cl, F, or I.

As used herein the term "comprising" or "comprises" is used in reference to compounds, compositions, formulation and methods, respective component(s) thereof, that are essential to the invention, yet open to the inclusion of unspecified elements, whether essential or not.

The term "consisting of" refers to compounds, compositions, formulations, methods, and respective components thereof as described herein, which are exclusive of any element not recited in that description of the embodiment.

Accordingly, in some embodiments, provided herein is a compound comprising the formula I:

FORMULA (I)

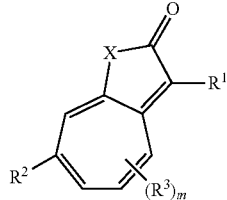

wherein $R^1$ is optionally substituted aryl, optionally substituted heteroaryl, optionally substituted phenyl or an optionally substitute indole;

wherein $R^2$ is $OR^7$, $SR^7$, $SO_2R^7$, $SSR^7$, wherein $R^7$ is H, optionally substituted alkyl, optionally substituted alkenyl, optionally substituted alkynyl, optionally substituted acyl, optionally substituted aryl or formula (I);

wherein $R^3$ is $OR^6$, $SR^6$, $SSR^6$, halogen, CN, $N(R^6)_2$, $NO_2$, optionally substituted alkyl, optionally substituted alkenyl, or optionally substituted alkynyl;

wherein X is O, S, $NR^6$; and wherein m is 0, 1, 2, 3, or 4.

A preferred substituted phenyl is

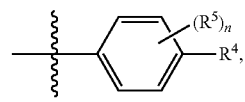

wherein $R^4$ is H, $OR^6$, $SR^6$, halogen, CN, $CF_3$, $N(R^6)_2$, $NO_2$, optionally substituted alkyl, optionally substituted alkenyl, or optionally substituted alkynyl; n is 0, 1, 2, 3, or 4; and $R^5$ is $OR^6$, $SR^6$, $SSR^6$, halogen, CN, $CF_3$, $N(R^6)_2$, $NO_2$, optionally substituted alkyl, optionally substituted alkenyl, or optionally substituted alkynyl. Preferably, $R^4$ is H or $OR^6$. More preferably $R^4$ is H, OH, or OMe.

In some embodiments, n is 0.

In some embodiments, $R^4$ is

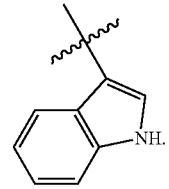 [SMILES: *c1c[nH]c2ccccc12]

In some embodiments, $R^7$ is H, methyl, ethyl, propyl, butyl, pentyl, or hexyl. In some embodiments, $R^7$ is an optionally substituted arylcarbonyl. One exemplary optionally substituted arylcarbonyl is

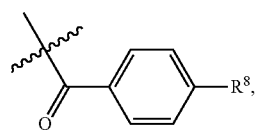

wherein $R^8$ is H, $OR^6$, $SR^6$, halogen, CN, $CF_3$, $N(R^6)_2$, $NO_2$, optionally substituted alkyl, optionally substituted alkenyl, or optionally substituted alkynyl.

In some embodiments, $R^7$ is optionally substituted aryl. In some embodiments, optionally substituted aryl is optionally substituted phenyl. In some embodiments, optionally substituted phenyl is

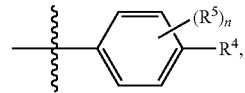

wherein $R^4$ is H, $OR^6$, $SR^6$, halogen, CN, $CF_3$, $N(R^6)_2$, $NO_2$, optionally substituted alkyl, optionally substituted alkenyl, or optionally substituted alkynyl; n is 0, 1, 2, 3, or 4; and $R^5$ is $OR^6$, $SR^6$, $SSR^6$, halogen, CN, $CF_3$, $N(R^6)_2$, $NO_2$, optionally substituted alkyl, optionally substituted alkenyl, or optionally substituted alkynyl. Preferably, $R^4$ is H or $OR^6$. More preferably R⁴ is H, OH, or OMe. In some embodiments, optionally substituted phenyl is p-hydroxy-phenyl. In some embodiments, optionally substituted phenyl is phenyl.

In some embodiments, m is 1.

In some embodiments, $R^3$ is $OR^6$, $SR^6$, $SSR^6$. $R^6$ is H, optionally substituted alkyl, optionally substituted alkenyl, optionally substituted alkynyl, optionally substituted acyl. Preferred alkyls for $R^6$ include methyl, ethyl, propyl, butyl, pentyl, and hexyl. Preferred $R^6$ groups for $R^3$ include H, methyl, ethyl, propyl, butyl, pentyl, and hexyl.

In some embodiments m is 1 and $R^3$ is OH, SH, or SSH.

In some embodiments, X is O.

In some embodiments, $R^7$ is

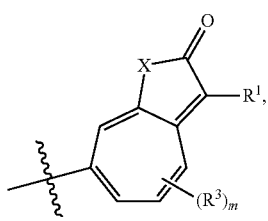

with variables $R^1$, $R^3$, and X as defined for formula (I) herein.

In some embodiments, $R^1$ is phenyl. In some embodiments, $R^4$ is H, $R^2$ is SH, X is O, and m=0. In some embodiments, $R^1$ is substituted phenyl wherein n=0, $R^4$ is OH, $R^2$ is SH, X is O, and m=0.

In one preferred embodiment, $R^1$ group is a substituted phenyl, $R^4$ is H, X is O, $R^2$ is SH, and n and m are both 0. The compound having the formula I of this preferred embodiment is Roseobacticide B.

In another preferred embodiment, $R^1$ group is a substituted phenyl, $R^4$ is OH, X is O, $R^2$ is SH, and n and m are both 0. The compound having the formula I of this preferred embodiment is Roseobacticide A.

In some embodiments, compound of formula (I) is selected from the group consisting of Roseobacticide A

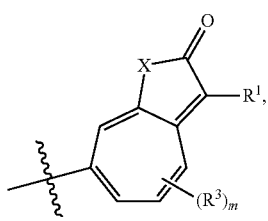

Roseobacticide B

Roseobacticide C

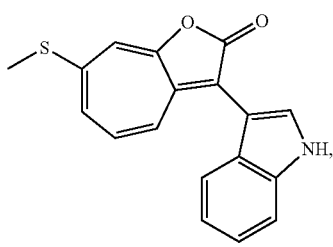

Roseobacticide D

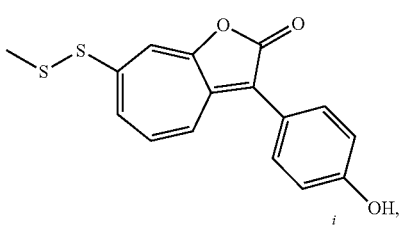

Roseobacticide E

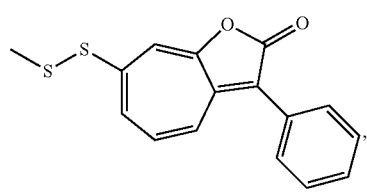

Roseobacticide F

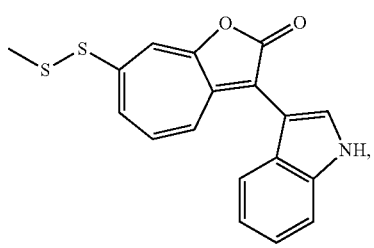

Roseobacticide G

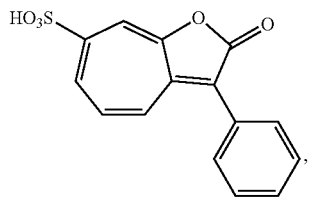

Roseobacticide H

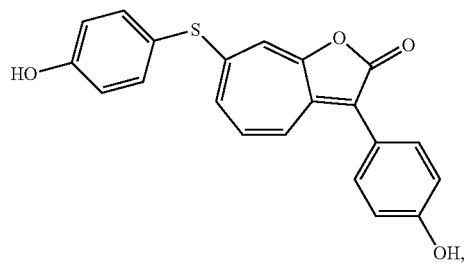

Roseobacticide I
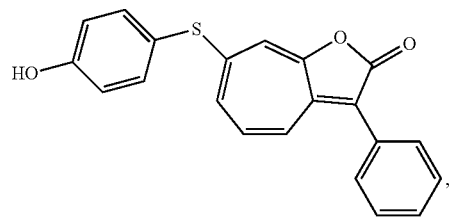
Roseobacticide J
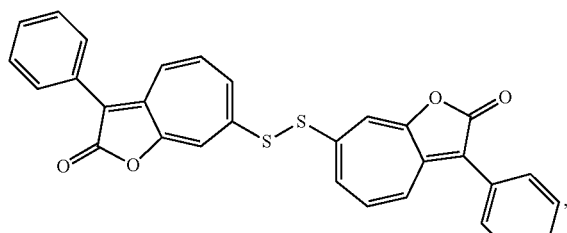
Roseobacticide K
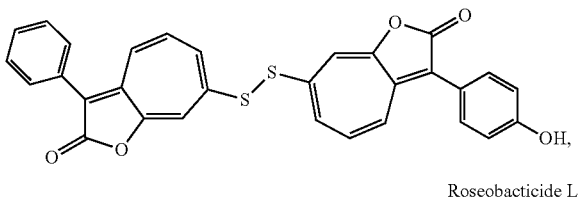
Roseobacticide L
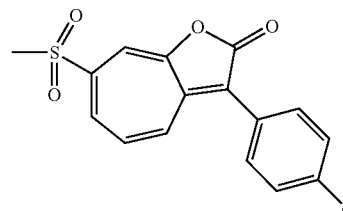
Roseobacticide M
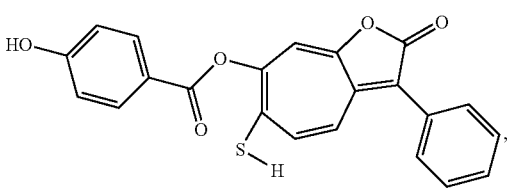
Roseobacticide N
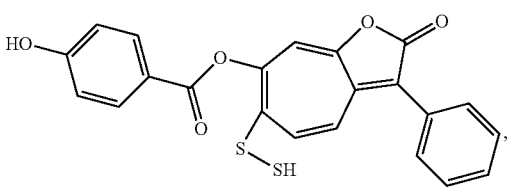
Roseobacticide O
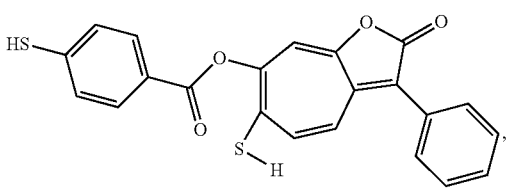
Roseobacticide P
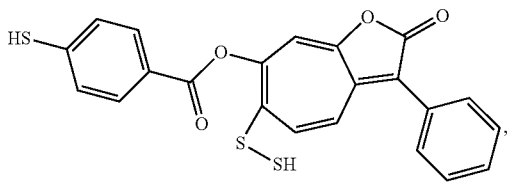
Roseobacticide Q
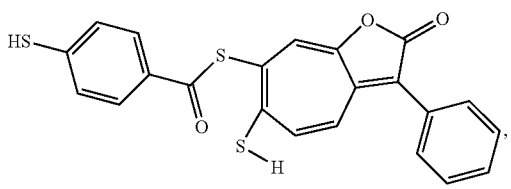
Roseobacticide R
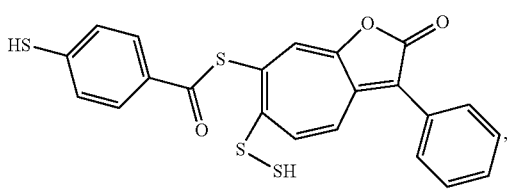
Roseobacticide S
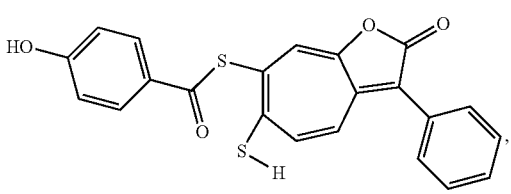
Roseobacticide T
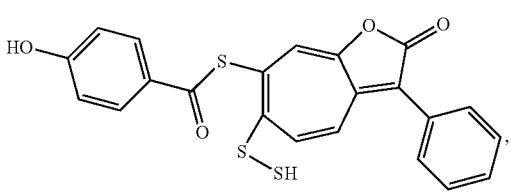
Roseobacticide U
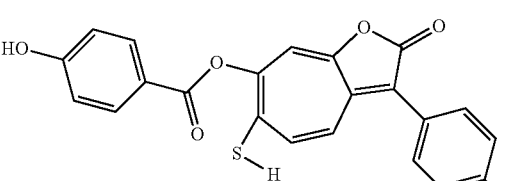
Roseobacticide V
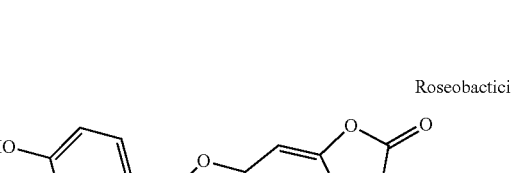
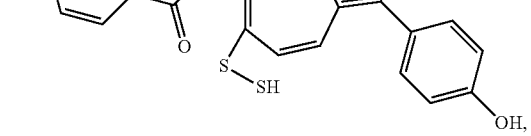

Roseobacticide W

Roseobacticide X

Roseobacticide Y

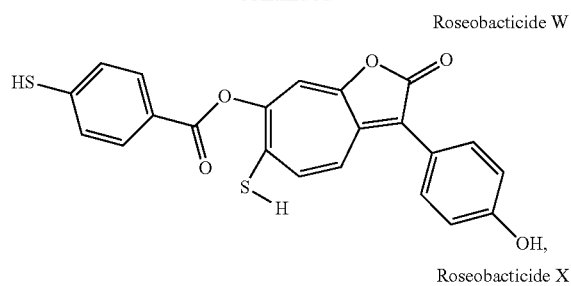

Roseobacticide Z

Roseobacticide AA

Roseobacticide BB

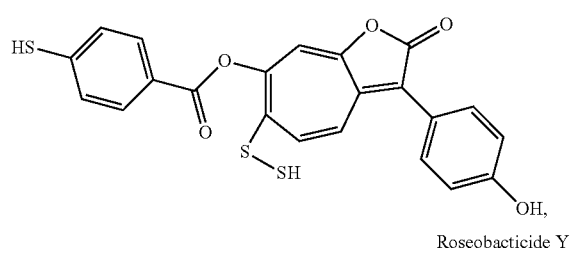

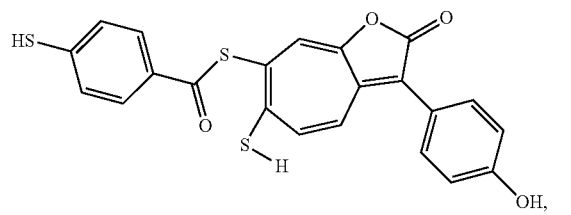

Roseobacticide CC

Roseobacticide DD

Roseobacticide EE

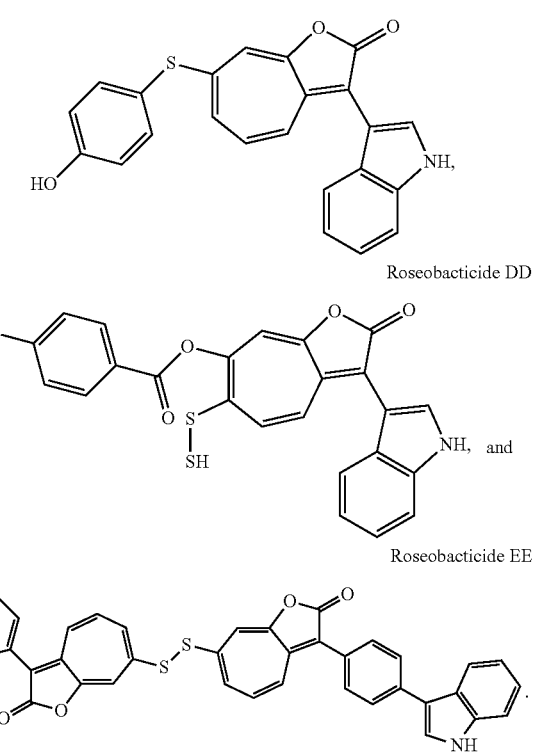

In some embodiments, the compound comprising the formula I has algicidal activity.

Marine bacteria and algae engage in intermittent symbioses mediated by unknown molecular signals and responses. Aspects of the invention are based on the discovery presented herein that p-coumaric acid (pCA) and other lignin-derived molecules, converts the *Roseobacter* genus strain *P. gallaeciensis* BS107 from a mutualist to a pathogen with respect to its bacterial relationship with the alga. pCA is the external signal that induces *P. gallaeciensis* BS107 to produce the potent phytotoxins, the Roseobacticides.

In part, described herein is the isolation and purification of Roseobacticides from *P. gallaeciensis* BS107 that were induced by pCA or other lignin-related molecules. Roseobacticides A-EE have unusual structures with no close relatives among known molecules. Both Roseobacticides A and B have an absorption peak at 430 nm. In addition, they share a 1-oxaazulan-2-one bicyclic core with an 8-thiomethyl group and a 3-phenyl or 3-(p-hydroxyphenyl) substituent. The bicyclic part of Roseobacticide A is planar, and its plane is rotated 33° around the C3-C11 bond relative to the plane of the p-hydroxyphenyl substituent.

The isolated and purified Roseobacticide A and Roseobacticide B exhibited potent but selective algaecidal activity. Incubation of *E. huxleyi* with Roseobacticide A and B resulted in cell lysis after 24 h, with cellular damage visible after 12 h (see FIG. 3). For example, Roseobacticide A showed an $IC_{50}$ of ≥2.2 μM, 0.10 μM, and >35 μM against the Prymnesiophytes *Emiliana huxleyi*, the cryptomonad *Rhodomonas salina* and the several diatoms, e.g., *Chaetoceros muelleri*, respectively. Roseobacticide B has an $IC_{50}$ of 0.19 μM when tested against *E. Huxleyi*.

In some embodiments, the compound comprising formula I has an algicidal activity of $LC_{50}$ between about 0.1 μM-35 μM. In some embodiments, the compound comprising formula I has an algicidal activity of $LC_{50}$ between about 0.1 µM-0.5 µM. In some embodiments, the compound comprising formula I has an algicidal activity of $LC_{50}$ between about 0.1 µM-1.0 µM. In some embodiments, the compound comprising formula I has an algicidal activity of $LC_{50}$ between about 0.5 µM-10 µM. In some embodiments, the compound comprising formula I has an algicidal activity of $LC_{50}$ between about 1.0 µM-10 µM. In some embodiments, the compound comprising formula I has an algicidal activity of $LC_{50}$ between about 10 µM-35 µM.

In some embodiments, the compound comprising formula I has an algicidal activity of $LC_{50}$ between 0.1 µM-35 µM selectively kill algae selected from the group consisting of Prymnesiophytes, cryptomonad and diatoms.

In some embodiments, provided herein is a composition comprises a compound having the formula I. In some embodiments, the composition has an algicidal activity. In some embodiments, provided herein is an algicidal formulation having a compound comprising formula I.

One skilled in the art can be easily determine algicidal activity, calculate $LC_{50}$ and estimate the affective amount or concentration necessary for use in controlling algal growth by any method known in the art, for example, in Sun-Og Lee, et al., 2000, Appl. Environ. Microbiol., 66:4334; Min-Ju Kim, et al., 2008, J. Appl. Phycology, 20:1069; X. Mayali and G. J. Doucette, 2002, Harmful Algae, 1:277; K. K. Schrader, 2002 in charter 4: Natural algicides for the control of Cyanobacterial-related off-Flavor in catfish aquaculture of "Off-Flavors in Aquaculture", pg. 195-208, U.S. Pat. Nos. 4,299,614, 5,541,150, 5,529,700, and International PCT application Publication No: WO/2007/073011. These references are incorporated herein by reference in their entirety. In some embodiments, algicidal activities of the compounds described herein can be determined but not limited to the lysis of algae method described in the Examples section.

Prymnesiophyta, also known as Haptophyta, includes about 500 living species in 50 genera, with many additional fossil genera and species, most notably the coccolithophorids. Members of this group are primarily unicellular and are photosynthetic. They are often important sources of food for aquatic communities. Prymnesiophyte algae are generally marine and are mostly tropical, though there are a few freshwater and terrestrial species reported. The group occurs worldwide, and several species have global distributions.

Some prymnesiophytes produce algal blooms which can cause serious problems for fish and for fishermen. Large blooms are problematic because of the mucilage surrounding the algal cells; it can clog fish gills, or render them permeable to dissolved toxins. Another problem is the production of dimethyl sulfide (DMS), a noxious-smelling compound which has been known to cause fish migrations to alter their normal routes.

The cryptomonads (or cryptophytes) are a group of algae, most of which have chloroplasts. They are common in freshwater, and also occur in marine and brackish habitats. Cells tend to be rather large, varying in shape between ovoid and elliptical. Each cell is around 10-50 µm in size and flattened in shape, with an anterior groove or pocket. At the edge of the pocket there are typically two slightly unequal flagella which aid in their movement. Uncontrolled cryptomonad algal blooms have been associated with increased inorganic and organic materials such as iron and phosphate run off into the rivers and lakes.

Diatoms are a major group of algae, and are one of the most common types of phytoplankton. Most diatoms are unicellular, although they can exist as colonies in the shape of filaments or ribbons (e.g., Fragillaria), fans (e.g., Meridion), zigzags (e.g., Tabellaria), or stellate colonies (e.g., Asterionella). Diatoms are producers within the food chain. A characteristic feature of diatom cells is that they are encased within a unique cell wall made of silica (hydrated silicon dioxide) called a frustule. These frustules show a wide diversity in form, but usually consist of two asymmetrical sides with a split between them, hence the group name.

In some embodiments, the compounds comprising formula I have an algicide activity selective against *E. huxleyi, R. sauna,* and *C. muelleri*.

In some embodiments, the compound and composition described herein are used for controlling algal growth, such as in preventing or halting the growth of algae in bodies of water, e.g., swimming pools, aquaculture ponds, freshwater ponds, aquariums, urban drainage systems, industrial cooling water systems, etc. The use of a compound comprising formula I or salts thereof as algicide in the treatment of water is distinguished by the surprisingly high algicidal action and therewith the very low dosage amount based on the estimated $LC_{50}$ values.

Accordingly, in some embodiments, the invention provides for a method of controlling algal growth in bodies of water, the method comprising adding to the water a sufficient amount of a compound comprising formula I or a salt thereof to kill and/or inhibit growth of algae in the water.

In some embodiments, provided herein is a method for the algicidal treatment of water containing algae, the method comprising adding to the water a sufficient amount of a compound comprising formula I or a salt thereof to kill and/or inhibit the growth of algae in the water.

In some embodiments, 100% of the algae is killed or lysed within 24 hr of adding the algicide. In some embodiments, about 95% of the algae is killed or lysed within 24 hr of adding the algicide. In other embodiments, about 90% of the algae, about 85% of the algae, about 80% of the algae, about 75% of the algae, about 70% of the algae, about 65% of the algae, about 60% of the algae, about 55% of the algae, about 50% of the algae, about 45% of the algae, about 40% of the algae, about 35% of the algae, about 30% of the algae, about 25% of the algae, about 20% of the algae, about 15% of the algae, about 10% of the algae, about 5% of the algae, or about 2% of the algae is killed or lysed within 24 hr of adding the algicide. One skilled in the art would recognize that the percent killed or lysed depends on several factors, e.g., the amount or concentration of the algicide added to the water needing treatment and the amount of algae colonizing of the water.

In some embodiments, complete 100% inhibition of growth of algae occurs within 24 hr of adding the algicide and this level of inhibition remains for consecutive 3 days after adding the algicide. In some embodiments, 75% inhibition of growth of algae occurs within 24 hr of adding the algicide and this level of inhibition remains for 3 days after adding the algicide. In some embodiments, 50% inhibition of growth of algae occurs within 24 hr of adding the algicide and this level of inhibition remains for 3 days after adding the algicide. One skilled in the art would recognize that the percent algal growth depends on several factors, e.g., the amount or concentration of the algicide added to the water needing treatment and the amount of algae colonizing of the water.

In some embodiments, provided herein is a method for the algicidal treatment of swimming pool water containing algae, the method comprising adding to the swimming pool water an effective amount of the compound comprising formula I or a salt thereof to kill and/or inhibit the growth of the algae in the swimming pool water.

In some embodiments, the water or bodies of water is selected from the group consisting of swimming pools, aquaculture ponds, freshwater ponds, aquariums, urban drainage systems and industrial cooling water systems.

In some embodiments, the salts of the compound comprising formula I includes but are not limited to lactates, gluconates, chlorides, acetates, bromides, sulfates, acetates, formates, trichloroacetates, hydrocarbonates and other solubilizing anions. In some embodiments, the salts help dissolve the compound in water. In some embodiments, water-soluble salts of the compound are used, e.g., lactate or gluconate, is preferred. These water-soluble salts can be used in solid form or as aqueous solution. Alternatively, more poorly soluble salts such as chloride or acetate can be added as powder, granulate or tablets to the water to be treated.

In some embodiments, the compound comprising formula I or a salt thereof is between about 0.001 to 99% by weight when added to the body of water. In other embodiments, the compound comprising formula I or a salt thereof is from about 0.001 to 50% by weight, about 0.05 to 50% by weight, about 5 to 50% by weight, about 10 to 50% by weight, about 20 to 50% by weight, about 30 to 50% by weight, about 40 to 50% by weight, about 1 to 80% by weight, about 5 to 80% by weight, about 10 to 80% by weight, about 20 to 80% by weight, about 30 to 80% by weight, about 40 to 80% by weight, about 50 to 80% by weight, about 60 to 80% by weight, about 70 to 80% by weight, about 5 to 30% by weight, about 10 to 30% by weight, about 15 to 30% by weight or about 20 to 30% by weight. More preferably, from 0.001 to 20% by weight.

In some embodiments, the compound comprising Roseobacticide A or Roseobacticide B or a salt thereof respectively is between about 0.001 to 99% by weight when added to the body of water. In some embodiments, the compound comprising Roseobacticide A or Roseobacticide B or a salt thereof respectively is about 0.001 to 50% by weight, about 0.01 to 50% by weight, about 0.05 to 50% by weight, about 1 to 50% by weight, about 5 to 50% by weight, about 10 to 50% by weight, about 20 to 50% by weight, about 30 to 50% by weight, about 40 to 50% by weight, about 1 to 80% by weight, about 5 to 80% by weight, about 10 to 80% by weight, about 20 to 80% by weight, about 30 to 80% by weight, about 40 to 80% by weight, about 50 to 80% by weight, about 60 to 80% by weight, about 70 to 80% by weight, about 5 to 30% by weight, about 10 to 30% by weight, about 15 to 30% by weight or about 20 to 30% by weight. More preferably, from 0.001 to 20% by weight.

In some embodiments, the compound comprising any one or multiples of Roseobacticides A-EE or a salt thereof respectively is between about 0.001 to 99% by weight when added to the body of water. In some embodiments, the compound comprising any one or multiples of Roseobacticides A-EE or a salt thereof respectively is about 0.001 to 50% by weight, about 0.01 to 50% by weight, about 0.05 to 50% by weight, about 1 to 50% by weight, about 5 to 50% by weight, about 10 to 50% by weight, about 20 to 50% by weight, about 30 to 50% by weight, about 40 to 50% by weight, about 1 to 80% by weight, about 5 to 80% by weight, about 10 to 80% by weight, about 20 to 80% by weight, about 30 to 80% by weight, about 40 to 80% by weight, about 50 to 80% by weight, about 60 to 80% by weight, about 70 to 80% by weight, about 5 to 30% by weight, about 10 to 30% by weight, about 15 to 30% by weight or about 20 to 30% by weight. More preferably, from 0.001 to 20% by weight.

In some embodiments, a compound comprising multiples of Roseobacticides A-EE, can comprise two or more of Roseobacticides A-EE, e.g., two of Roseobacticides A-EE, or three of Roseobacticides A-EE, or four of Roseobacticides A-EE, or five or more of Roseobacticides A-EE.

The concentration of the compound comprising formula I or a salt thereof added to water is a function of the purpose and of the special requirements. In some embodiments, the concentration of compound comprising formula I or a salt thereof is between about 0.001 to 10 parts per million (ppm) calculated as the compound comprising formula I or salt thereof in the water. In other embodiments, the concentration is between about 0.025 to 10 ppm, between about 0.01 to 10 ppm, between about 0.1 to 10 ppm, between about 0.5 to 10 ppm, between about 1 to 10 ppm, between about 3 to 10 ppm, between about 5 to 10 ppm, between about 0.025 to 3 ppm, between about 0.01 to 3 ppm, between about 0.1 to 3 ppm, between about 0.5 to 3 ppm, between about 1 to 3 ppm, between about 2 to 3 ppm, between about 0.025 to 5 ppm, between about 0.01 to 5 ppm, between about 0.1 to 5 ppm, between about 0.5 to 5 ppm, between about 1 to 5 ppm, between about 2 to 5 ppm, between about 3 to 5 ppm or between about 4 to 5 ppm.

In some embodiments, the concentration of compound comprising Roseobacticide A or Roseobacticide B or a salt thereof respectively when used in controlling alga growth is between about 0.001 to 10 parts per million (ppm) calculated as the compound comprising Roseobacticide A or Roseobacticide B or salt thereof respectively in the water. In other embodiments, the concentration is between about 0.025 to 10 ppm, between about 0.01 to 10 ppm, between about 0.1 to 10 ppm, between about 0.5 to 10 ppm, between about 1 to 10 ppm, between about 3 to 10 ppm, between about 5 to 10 ppm, between about 0.025 to 3 ppm, between about 0.01 to 3 ppm, between about 0.1 to 3 ppm, between about 0.5 to 3 ppm, between about 1 to 3 ppm, between about 2 to 3 ppm, between about 0.025 to 5 ppm, between about 0.01 to 5 ppm, between about 0.1 to 5 ppm, between about 0.5 to 5 ppm, between about 1 to 5 ppm, between about 2 to 5 ppm, between about 3 to 5 ppm or between about 4 to 5 ppm.

In some embodiments, the concentration of compound comprising any one of or multiples of Roseobacticides A-EE or a salt thereof respectively when used in controlling alga growth is between about 0.001 to 10 parts per million (ppm) calculated as the compound comprising any one of or multiples of Roseobacticides A-EE or salt thereof respectively in the water. In other embodiments, the concentration is between about 0.025 to 10 ppm, between about 0.01 to 10 ppm, between about 0.1 to 10 ppm, between about 0.5 to 10 ppm, between about 1 to 10 ppm, between about 3 to 10 ppm, between about 5 to 10 ppm, between about 0.025 to 3 ppm, between about 0.01 to 3 ppm, between about 0.1 to 3 ppm, between about 0.5 to 3 ppm, between about 1 to 3 ppm, between about 2 to 3 ppm, between about 0.025 to 5 ppm, between about 0.01 to 5 ppm, between about 0.1 to 5 ppm, between about 0.5 to 5 ppm, between about 1 to 5 ppm, between about 2 to 5 ppm, between about 3 to 5 ppm or between about 4 to 5 ppm.

In some embodiments, the concentration of compound comprising formula I or a salt thereof can be present in the range of about 0.5 g/l to about 250 g/l, in the range of about 1 g/l to about 250 g/l, in the range of about 5 g/l to about 50 g/l, in the range of about 1 g/l to about 50 g/l, in the range of about 5 g/l to about 20 g/l, in the range of about 1 g/l to about 20 g/l, in the range of about 5 g/l to about 250 g/l, in the range of about 5 g/l to about 100 g/l, in the range of about 1 g/l to about 100 g/l, in the range of about 5 g/l to about 20 g/l, in the range of about 1 g/l to about 200 g/l, in the range of about 10 g/l to about 250 g/l, in the range of about 10 g/l to about 50 g/l, in the range of about 10 g/l to about 20 g/l, in the range of about 10 g/l to about 100 g/l, in the range of about 10 g/l to about 200 g/l, in the range of about 50 g/l to about 250 g/l, in the range of about 50 g/l to about 200 g/l, in the range of about 50 g/l to about 100 g/l, in the range of about 100 g/l to about 250 g/l, or in the range of about 100 g/l to about 200 g/l it the water.

In some embodiments, the amount of the compound comprising formula I or a salt thereof used is sufficient to kill the alga present in the water. In some embodiments, the amount of the compound comprising formula I or a salt thereof used is sufficient to inhibit growth of alga for three consecutive days. In some embodiments, the amount of the compound comprising formula I or a salt thereof is an amount effective to keep the water clear of algae for at least three days. In some embodiments, the amount of the compound comprising formula I or a salt thereof is an amount effective to prevent algae in the water from increasing for at least three days.

In some embodiments, the amount of the compound comprising formula I or salt thereof added is sufficient to convert the swimming pool water from green to colorless in appearance, wherein the green color is due to algal growth in the pool.

In some embodiments, provided herein is a method for protecting an industrial product against infestation and destruction by algae, cyanobacteria and other photoautotrope microorganisms, the method comprising incorporating in the industrial product an effective amount of a compound comprising formula I or a salt thereof to kill and/or prevent algae growth. In some embodiments, incorporating refers to coating the industrial product with a compound comprising formula I or a salt thereof. In some embodiments, a composition and/or formulation comprising a compound of formula I or a salt thereof is used to protect an industrial product.

Industrial materials which are in contact with water for a major part of their functional life are easily colonized by algae and adversely affected by the algal metabolic activities. Examples include fishing nets and plastics used in swimming pools. The performance of fishing nets can be severely affected by algal growth. It is therefore customary to apply coatings containing algicides.

Moreover, other industrial material coatings that contain organic film formers can be colonized relatively quickly by algae. Such coatings are used on mineral substrates, textile finishes and wood paints and also materials made of plastics. Algal growth on these surfaces causes these surfaces to become discolored within a few months to an unsightly green/black. Additionally, these algae provide the platform upon which fungi, lichen and moss can grow; and the fungi, lichen and moss can destroy the coating chemically or mechanically by their growth. Therefore, preventing and/or inhibiting algal colonization and growth can prevent subsequent colonization and growth of cyanobacteria and other photoautotrope microorganisms which can destroy the coating on the industrial product.

An example of an industrial product that can benefit from the use of a compound comprising the formula I is the high-efficiency heat protection system. This system contain synthetic resin rendering that are mounted on to exterior walls for energy conservation. The synthetic resin renderings, owing to their physical properties, have a strong tendency to be colonized by algae. To maintain their value, these coatings are often admixed with microbicides.

In some embodiments, the materials or industrial products for which an effective amount of a compound comprising formula I or a salt thereof can be incorporated to inhibit and/or prevent algal growth include but are not limited to paints for exterior walls, synthetic resin rendering, wood coatings, wood varnishes, coatings for concrete, roof tile coatings, silicate paints, sealing materials, and textile finishes.

In some embodiments, a compound comprising formula I or a salt thereof according to the invention can be employed in the form of polyvinyl chloride-containing plastics, since they are temperature-stable and will not be destroyed by the thermal stress occurring during calendering. The use of such plastics for coating, e.g., fishing nets, can be prepared in easily processable formulations and in particular as a finely divided aqueous dispersion.

The concentration of a compound comprising formula I or a salt thereof to be used depends on several factors, e.g., the kind of material to be protected, the leach out stress and the expected degree of infestation by algae and other microbes, and can range from about 0.001 to 3% by weight, from about 0.01 to 3% by weight, from about 0.05 to 3% by weight, from about 0.01 to 2% by weight, from about 0.05 to 2% by weight, from about 0.005 to 1% by weight, from about 0.01 to 1% by weight, from about 0.05 to 1% by weight, from about 0.005 to 0.5% by weight, from about 0.01 to 0.5% by weight, from about 0.05 to 0.5% by weight, and preferably from 0.01 to 0.2% by weight, of a compound comprising formula I or a salt thereof, based on the material to be protected.

In some embodiments, the compound comprising formula I or a salt thereof is used in combination with other compounds, e.g., other algicides, herbicides, and other anti-microbial growth (e.g., fungal or bacterial growth). In some embodiments, provided herein is an algicidal formulation comprises a compound comprising formula I or a salt thereof. In some embodiments, provided herein is an algicidal formulation comprises a compound comprising formula I or a salt thereof in combination with other compounds, e.g., other algicides, herbicides, bactericides and fungicides. In some embodiments, the combination includes one other compound. In some embodiments, the combination includes more than one other compound, e.g., a herbicide and fungicide or a bactericide and a fungicide.

The compound comprising formula I or a salt thereof can be used for the algicidal treatment of water alone or in combination with other algicides and/or other microbicidal active substances, e.g., bactericidal, virucidal and fungicidal active substances. However, other algicides and/or other microbicidal active substances, e.g., bactericidal, virucidal and fungicidal active substances, are not required and are only optionally used in the methods described here using the compound comprising formula I or a salt thereof.

In some embodiments, the methods described here can include the enzymes utilized in U.S. Pat. No. 5,356,803 and the aryl- or aryloxyalkanol, anionic surfactant, zwitterionic and amphoteric surfactant, nonionic surfactant, dihydric alcohol, C8-12 fatty acid, solubilizer, and/or deionized water utilized in EP-A 0,259,249 (corresponding to AU 8775999). In other embodiments, the methods described here do not require or do not use the enzymes utilized in U.S. Pat. No. 5,356,803. Furthermore, the present invention does not require or does not use the aryl- or aryloxyalkanol, anionic surfactant, zwitterionic and amphoteric surfactant, nonionic surfactant, dihydric alcohol, C8-12 fatty acid, solubilizer, and/or deionized water utilized in EP-A 0,259,249.

There are certain advantages to combining other compounds with the compound comprising formula I or a salt thereof. For example, combinations of the compound comprising formula I or a salt thereof with an algicidally active, polymeric guanidine compound, e.g., polyhexamethylene biguanide, can be very effective. The dosages of the biguanide, when used alone, i.e. without the compound comprising formula I, is at or over 10 ppm. When used in combination with the compound comprising formula I, the concentration of biguanide used can be considerably reduced by such a combination so that the disadvantages associated with the high concentration of biguanide are reduced. For example, a disadvantage associated with using polymeric biguanide is the formation of slimy particles in the water which occurs when it is used for a fairly long time; these particles can hinder the functioning of sieves and filters and optically disturb the bathers. Moreover, after fairly long usage the algicidal action is insufficient, so that an increased use of hydrogen peroxide or per salts is necessary. When a reduced amount of biguanide is used, any opacity that occurs will dissolve again given sufficient dilution with the water to be treated.

An example of an herbicide that can be used with the compound comprising formula I or a salt thereof described and also can be use as an algicide is diuron. Diuron is used for finishing industrial materials, e.g., in paints for exterior walls and in renders. Other examples include but are not limited to ametryn, desmetryn, dimethametryn, dipropetryn, methoprotryn, prometryn, terbutryn and 2-methylthio-4-cyclopropylamino-6-tert-butylamino-1,3,5-triazine (Mctt), chlorbromuron, chlortoluron, diuron, difenoxuron, fluometuron, isoproturon and neburon described in U.S. Pat. No. 6,117,817. This reference is incorporated herein by reference in its entirety.

Examples of fungicides and bactericides that can be used with the compound comprising formula I or a salt thereof described include but are not limited to the following: benzimidazole derivatives, such as, for example, carbendazim or thiabendazole, quaternary ammonium salts (quats), such as, for example, didecyldimethylammonium chloride, thiocyanate compounds, such as, for example, 2-thiocyanatomethylthiobenzothiazole, carbamates, such as, for example, iodopropynyl butylcarbamate, isothiazolinone derivatives, such as, for example, 2-octylisothiazolin-3-one, triazole fungicides, such as, for example, tebuconazole, imidazole fungicides, such as, for example, prochloraz, halogenated sulfides, such as, for example, dichlofluanid, tolylfluanid, captan, folpet and nitriles, such as, for example, tetrachlorophthalodinitrile.

Formulations comprising a compound comprising formula I or a salt thereof according to the invention and a fungicide mixture can also be advantageous. An example is a combination of carbendazim, 2-octylisothiazolinone, terbutryn and difenoxuron. These active compound combinations ensure a comprehensive long-term protection of industrial materials against infestation by discolorizing and destructive microorganisms. The active compounds can be formulated as a solution in a manner known per se. The choice of solvent is not decisive, particularly suitable solvents for apolar systems are aromatic petroleum fractions, xylene, trimethylbenzene; ketones, such as, for example, acetone, cyclohexanone, isophorone, methyl isobutyl ketone; ethers and glycol ethers, such as, for example, diisopropyl ether, dimethoxyethane, diethylene glycol dimethyl ether, triethylene glycol dimethyl ether; esters, such as ethyl acetate, butyl acetate; glycols, mono- and diethers thereof or mono- or diesters thereof; amides, such as, for example, dimethylformamide, N-methylpyrrolidone and N-octylpyrrolidone. The mentioned solvents can also be employed as mixtures. In solvent-free aqueous systems, preference is given to using water-based pastes of the algicides.

In some embodiments, the algaecide formulation further comprises a defoamer, e.g., an anti-foaming agent. In some embodiments, the anti-foaming agent is eucalytptus oil.

Isolation and Purification of Roseobacticide a and Roseobacticide B

In some embodiments, the compounds described herein are isolated and purified empirically from the organism that synthesizes the compounds.

In some embodiments, the compounds described herein are isolated and purified from bacteria of the genus *Roseobacter*. In some embodiments, the compounds described herein are isolated and purified from *P. gallaeciensis*. In some embodiments, the compounds described herein are isolated and purified from *P. gallaeciensis* BS107. In some embodiments, the compounds described herein are isolated and purified from *P. gallaeciensis* 2.10.

In some embodiments, the compounds described herein are isolated and purified from bacteria which have been contacted with one or more elicitors of Roseobacticide synthesis. In some embodiments, the compounds described herein are isolated and purified from bacteria which have been contacted with one or more components, precursors, or degradation products of cell wall lignin. In some embodiments, the compounds described herein are isolated and purified from bacteria which have been contacted with one or more intermediates in the synthesis of components, precursors, or degradation products of cell wall lignin. In some embodiments, the compounds described herein are isolated and purified from bacteria which have been contacted with one or more of; pCA (p-coumaric acid), sinapic acid, ferulic acid and cinnamic acid.

The following is an exemplary for the isolation and purification of Roseobacticide A and Roseobacticide B. One skilled in the art can easily modify this example and adapt it for isolation and purification of other Roseobacticides produced by the Roseobacticide clade bacteria, e.g., Roseobacticide C-EE disclosed herein.

*P. gallaeciensis* BS107 is streaked out from frozen stocks and maintained on Marine Broth (Difco 2216) supplemented with 1.5% agar and incubated at 30° C. for two days. A 50 mL test tube containing 5 mL of ½ strength yeast extract, tryptone and sea salt medium (YTSS, per L: 2 g yeast extract, 1.25 g tryptone, 20 g sea salt) was inoculated with each strain and grown overnight at 30° C. on a horizontal rotating drum fermenter. A 500 mL Erlenmeyer flask containing 50 mL of YTSS medium and 1 mM pCA was inoculated with 0.5 mL of the overnight culture and incubated at 160 rpm and 30° C. for 3 d. The culture is expanded to 4 L of YTSS medium.

The purification of Roseobacticides was carried out in the dark or under dim light. After three days, the culture was extracted once with an equal volume of ethyl acetate. The extract was dried over $Na_2SO_4$ and evaporated to dryness in vacuo. The residue was dissolved in $CH_2Cl_2$ and fractionated by flash silica gel chromatography (40 g, d=2.5 cm, l=20 cm). Roseobacticides were eluted with a gradient of 0-20% MeOH in $CH_2Cl_2$. The fractions containing Roseobacticides, as monitored by the distinct broad 430 nm peak by UV-visible spectroscopy, were pooled, dried in vacuo, and purified further by reverse phase HPLC on a preparative Phenomenex C18 column (5 Jlm, 21.2×250 mm) operating at 12 mL/min using an isocratic elution of 35% of MeCN in H2O, followed by a gradient of 35-100% MeCN in $H_2O$ over 40 min. Roseobacticides A and B were then purified further using a semi-preparative Supelco Discovery HS C18 column (10 pm, 10×250 mm) operating at 3 mL/min with a gradient of 30-100% MeOH in $H_2O$ over 35 min. Roseobacticides A and B were purified to homogeneity by reapplication onto the Supelco Discovery HS C18 column and eluting with the same gradient. This procedure yielded 1.2 mg and 0.2 mg of Roseobacticide A and B, respectively from 4 L of *P. gallaeciensis* BS107 cultured in the presence of 1 mM pCA.

Chemical Synthesis of Roseobacticide A and Roseobacticide B

In some embodiments, the compound of Formula I described herein can chemically synthesized by any method known in the art. For example, Roseobacticide A and Roseobacticide B can be chemically synthesized according to the schemes described in FIGS. 2C and 5. In addition, one skilled in the art would be able to make modification in accordance to methods described in Asao, T. et al., 1972, J. Am. Chem. Soc. 94:3655; Morita, N. and Kitatara, Y., Tet. Lett. 1972, 9:869; and Lellek, V. and Hansen, H-J., Helv. Chim. Acta, 2001, 84:3548. These references are incorporated herein by reference in their entirety. One skilled in the art can easily make modifications and adapt the methods for the chemical synthesis of other Roseobacticides produced by the Roseobacticide clade bacteria, e.g., Roseobacticide C-EE disclosed herein.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

The activity of the algicide combinations according to the invention against algae can be measured by determining the minimum inhibitory concentrations (MIC values). (Literature: K. Grossmann, R. Berghaus, G. Retzlaff; Pesticide Science (1992), 35, 283).

Unless otherwise stated, the present invention was performed using standard procedures known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Robert Andersen (ed) Algal Culturing Techniques, 2005, Academic Press; Edmond de Hoffmann and Vincent Stroobant, Mass spectrometry: principles and applications, Wiley-Interscience, 2007; Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Methods in Molecular biology, Vol. 180, Transgenesis Techniques by Alan R. Clark editor, second edition, 2002, Humana Press, and Methods in Meolcular Biology, Vo. 203, 2003, which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Those skilled in the art will recognize, or be able to ascertain using not more than routine experimentation, many equivalents to the specific embodiments of the invention described herein. Such equivalents are intended to be encompassed by the following claims.

This invention is further illustrated by the following examples which should not be construed as limiting. The contents of all references cited throughout this application, as well as the figures and table are incorporated herein by reference.

Some embodiments of the present invention can be defined as any of the following numbered paragraphs:

1. A compound comprising the formula:

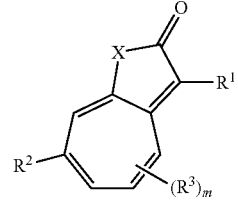

FORMULA (I)

wherein $R^1$ is optionally substituted aryl, optionally substituted heteroary, optionally substituted phenyl or an optionally substitute indole;

wherein $R^2$ is $OR^7$, $SR^7$, $SO_2R^7$, or $SSR^7$;

wherein $R^7$ is H, methyl, ethyl, propyl, butyl, pentyl, hexyl, optionally substituted alkyl, optionally substituted alkenyl, optionally substituted alkynyl, optionally substituted acyl, optionally substituted arylcarbonyl, optionally substituted aryl or formula (I);

wherein m is 0, 1, 2, 3, or 4, and wherein $R^3$ is $OR^6$, $SR^6$, $SSR^6$, halogen, CN, $N(R^6)_2$, $NO_2$, optionally substituted alkyl, optionally substituted alkenyl, or optionally substituted alkynyl;

wherein $R^6$ is H, methyl, ethyl, propyl, butyl, pentyl, hexy, optionally substituted alkyl, optionally substituted alkenyl, optionally substituted alkynyl, optionally substituted acyl;

and wherein X is O, S, $NR^6$.

2. The compound of paragraph 1, wherein the $R^1$ optionally substituted phenyl is

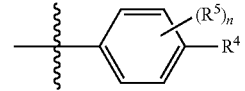

wherein $R^4$ is H, $OR^6$, $SR^6$, halogen, CN, $CF_3$, $N(R^6)_2$, $NO_2$, optionally substituted alkyl, optionally substituted alkenyl, or optionally substituted alkynyl;

n is 0, 1, 2, 3, or 4; and $R^5$ is $OR^6$, $SR^6$, $SSR^6$, halogen, CN, $CF_3$, $N(R^6)_2$, $NO_2$, optionally substituted alkyl, optionally substituted alkenyl, or optionally substituted alkynyl.

3. The compound of paragraph 2, wherein $R^4$ is H or $OR^6$.
4. The compound of paragraph 2, wherein $R^4$ is H, OH, or OMe.
5. The compound of paragraph 2, wherein $R^4$ is

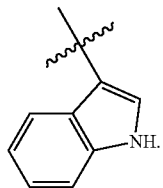

6. The compound of any paragraphs 1-5, wherein $R^7$ is

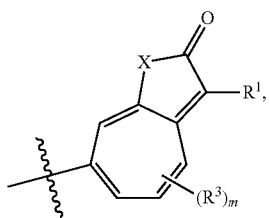

wherein the $R^1$, $R^3$, and X are as defined for formula (I).

7. The compound of any of paragraphs 1-5, wherein the $R^7$ optionally substituted arylcarbonyl is

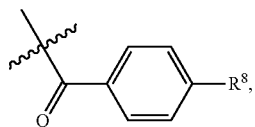

wherein $R^8$ is H, $OR^6$, $SR^6$, halogen, CN, $CF_3$, $N(R^6)_2$, $NO_2$, optionally substituted alkyl, optionally substituted alkenyl, or optionally substituted alkynyl.

8. The compound of any of paragraphs 1-7, wherein m is 1 and $R^3$ is OH, SH, or SSH.
9. The compound of any of paragraphs 1-8, wherein X is O.
10. The compound of any of paragraphs 1-9, wherein the compound is selected from the group consisting of Roseobacticide A

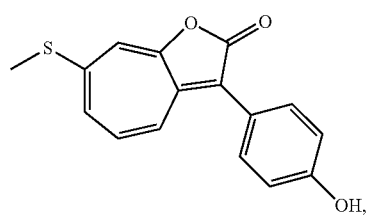

Roseobacticide B

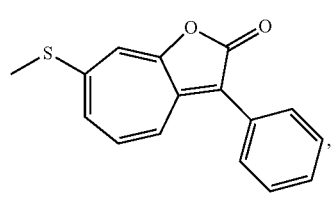

Roseobacticide C

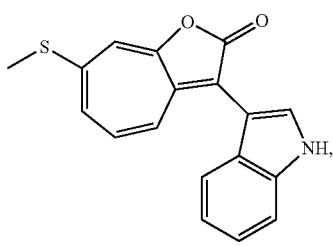

Roseobacticide D

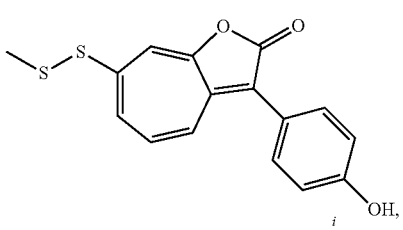

Roseobacticide E

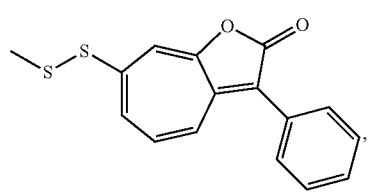

Roseobacticide F

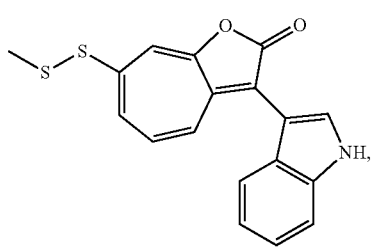

Roseobacticide G

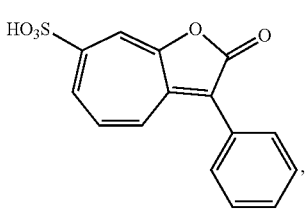

Roseobacticide H

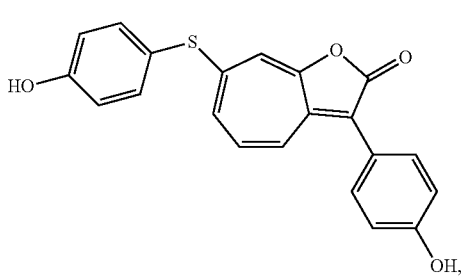

-continued

Roseobacticide I

Roseobacticide J

Roseobacticide K

Roseobacticide L

Roseobacticide M

Roseobacticide N

Roseobacticide O

-continued

Roseobacticide P

Roseobacticide Q

Roseobacticide R

Roseobacticide S

Roseobacticide T

Roseobacticide U

Roseobacticide V

-continued

Roseobacticide W
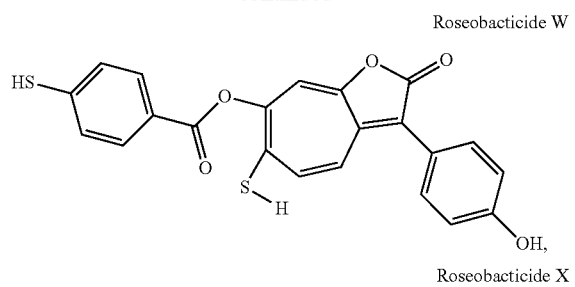

Roseobacticide X
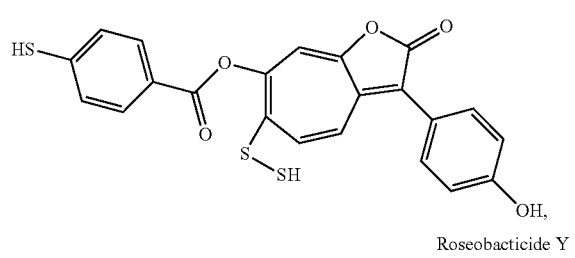

Roseobacticide Y
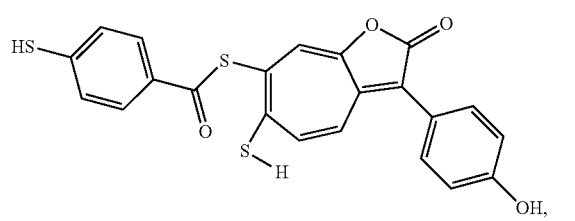

Roseobacticide Z
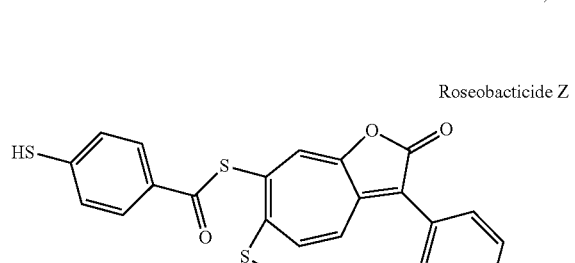

Roseobacticide AA
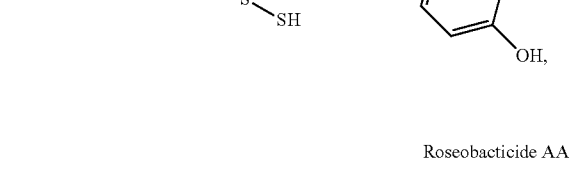

Roseobacticide BB
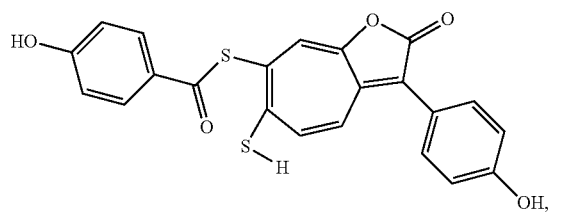

-continued

Roseobacticide CC
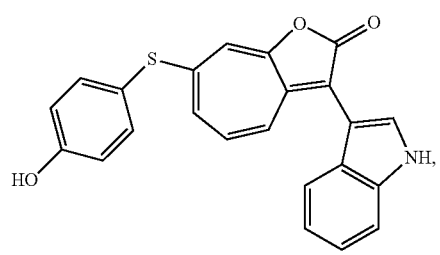

Roseobacticide DD
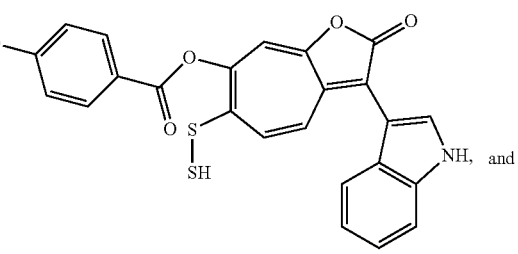

Roseobacticide EE
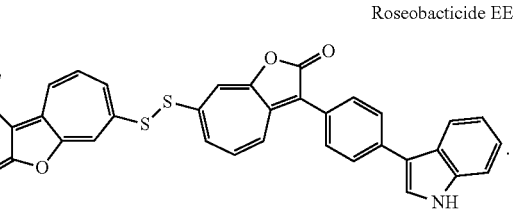

11. The compound of any of paragraphs 1-10, wherein the compound has algicidal activity.
12. The compound of paragraph 11, wherein the algicidal activity has an $LC_{50}$ of 0.01 μM to 35 μM.
13. The compound of paragraphs 11 or 12, wherein the algicide composition specifically kills the algae *Emiliana huxleyi*.
14. A composition comprising a compound of any of paragraphs 1-13.
15. An algicide formulation comprising a compound of any of paragraphs 1-13.
16. The algicide formulation of paragraph 15 further comprising an algicide, a herbicide, a bactericide or a fungicide.
17. A method of controlling algal growth in a body of water, the method comprising adding to the water a sufficient amount of a compound, composition or formulation of any of paragraphs 1-16 or a salt thereof to kill or inhibit growth of algae in the water.
18. The method of paragraph 17, wherein the body of water is selected from the group consisting of swimming pools, aquaculture ponds, freshwater ponds, aquariums, urban drainage systems and industrial cooling water systems.
19. A method for protecting an industrial product against infestation and destruction by algae, cyanobacteria and other photoautotrope microorganisms, the method comprising incorporating in the industrial product an effective amount of a compound, composition or formulation of any of paragraphs 1-16 or a salt thereof to kill and/or prevent algae growth.
20. A material or industrial product comprising a compound, composition or formulation of any of paragraphs 1-16, wherein the compound, composition or formulation applied thereon or is incorporate within.

21. The material or industrial product of paragraph 20, wherein material or industrial product is selected from the group consisting of paints, polyvinyl chloride-containing plastics, varnishes, sealing materials, textile finishes, synthetic resin rendering, wood finishes and coatings, and roof tile coatings.

EXAMPLES

Example 1

Naturally Occurring Roseobacticide A and B

Eukaryotes evolved on a planet teeming with bacteria, and close associations between the two characterize life as we know it. In some interactions the bacterial symbiont switches from a harmless or even a helpful member of its eukaryotic host's microbial community into a deadly pathogen (Rosenberg, E., et al., 2007, Nat. Rev. Microbiol. 5, 355-362). As bacteria largely sense their environment through molecules, a molecular signal from the eukaryotic host typically initiates the switch, and bacteria respond by producing molecular virulence factors Lutgendorff, F., at el., Curr. Mol. Med. 8, 282-298 (2008). Outside of medical microbiology, relatively few of these initiators and responses have been studied in molecular detail, and most of the molecular players remain to be discovered. Their discovery provides both valuable insights for microbial chemical ecology and sources of potentially useful small molecules (Clardy, J., 2005, Genome Biol. 6, 232-232.4; Shank, E. A. & Kolter R., 2009, Curr. Opin. Microbiol. 12, 205-2 14).

Among the most abundant and least investigated bacterium-eukaryote symbioses are those that occur in the oceans between bacteria and algae, especially those between members of the roseobacter clade and microscopic algae (Gonzalez, J. M. et al., 2000, Appl. Environ. Microbiol. 66, 4237-4246). The roseobacters constitute a diverse clade within the α-Proteobacteria and account for up to 60% of the bacterial community during algal blooms (Gonzalez, J. M. et al., supra). During these blooms, intermittent associations are thought to form between roseobacters and algae, in which either can be attracted to or repelled by the other (Miller, T. R. & Belas, 2006, R. Environ. Microbiol. 8, 1648-1659; Kjelleberg, S. et al., 1997, Aquat. Microb. Ecol. 13, 85-93; Joint, I. et al., 2002, Science 298, 1207-1207; Rao, D. et al., 2007, Appl. Environ. Microbiol. 73, 7844-7852. Since many algae cannot grow normally in marine settings without bacterial symbionts, bacterial colonization of algae may be largely beneficial (Matsuo,Y., at el., 2005, Science 307, 1598-1598. The bacterially conferred benefit is not well understood, but some studies suggest that roseobacter metabolites may be antibiotics and auxins, which suppress the growth of potentially parasitic bacteria and promote algal growth, respectively (Rao, D. et al., 2007, supra; Bruhn, J. B. et al., 2005, Appl. Environ. Microbiol. 71, 7263-7270). The algae, in turn, could contribute a suitable surface for roseobacter colonization and biofilm formation.

Materials and Methods
General Procedures $^1$H, $^{13}$C and 2-D NMR spectra for Roseobacticides were recorded in the inverse-detection probe of a Varian Inova spectrometer (600 MHz for $^1$H, 150 MHz for $^{13}$C). $^{13}$C NMR spectra were recorded on the same instrument with a broadband probe. The 1-D/2-D NMR spectra for Roseobacticide A and B were collected in a 3 mm Norell Select Series NMR tube (Sigma Aldrich) and a 1.7 mm NMR Capillary tube (Wilmad), respectively. UV-visible absorbance spectra were collected on an Amersham Biosciences Ultrospec 5300 Pro Spectrophotometer. HPLC purifications were carried out on an Agilent 1100 or 1200 Series HPLC system equipped with a photo diode array detector. HPLC-MS analysis was performed on an Agilent 1200 Series HPLC system equipped with a diode array detector and a 6130 Series ESI mass spectrometer using an analytical Phenomenex Luna C18 column (5 μm, 4.6×100 mm) operating at 0.7 mL/min with a gradient of 10% MeCN in H2O to 100% MeCN over 25 min. High resolution mass spectrometry (HR-MS) and tandem MS (MS/MS) were performed at the University of Illinois Urbana-Champaign Mass Spectrometry Facility.

Bioinformatic Analyses of the E. Huxleyi Genome.

Characterized Arabidopsis proteins known to be involved in lignin biosynthesis were used as queries into the JGI V 1.0 database hosted at JGI using BLASTp and default settings. The top scoring candidate homolog was then used as a query back into the Arabidopsis genome and into the nr database. Candidates were deemed as orthologous if the initial query was returned or a named homologue thereof with an E-value above 1E-30 and better than the next best homologue of a different function by at least 2 orders of magnitude.

HPLC-MS Analysis of E. Huxleyi Cultures.

Approximately 10-day old cultures of two strains of E. huxleyi (strain CCMP1516 and strain CCMP372) were obtained from the CCMP. A 10 mL aliquot of each was frozen and lyophilized to dryness. A 15-30 mg aliquot of the dried material was dissolved in 0.3 mL MeOH and supplemented with 15 μL formic acid. The resulting suspension was sonicated briefly and heated to 90° C. for 30-45 min. The mixture was then spun down in a centrifuge, filtered and analyzed by HPLC-MS using a Phenomenex Luna C18 column (5 μm, 4.6×100 mm) operating at 0.7 mL/min with a gradient of 15% MeCN in H2O (+0.1% formic acid) to 100% MeCN (+0.1% formic acid) over 25 min. The samples were also analyzed by HPLC on a Supelco Discovery C18 analytical column (5 μm, 4.6×250 mm) using a S3 gradient of 15% MeCN in H2O (+0.1% formic acid) to 85% MeCN in H2O (+0.1% formic acid) over 34 min. In each case, commercially available p-coumaric acid was analyzed under the same conditions as standard.

Cultivation of Roseobacter Strains and LC-MS Analysis

Roseobacter (Phaeobacter gallaeciensis BS107, Ruegeria sp. R11 and Silicibacter pomeroyi DSS3) and other marine strains (see Table 4) were streaked out from frozen stocks and maintained on Marine Broth (Difco 2216) supplemented with 1.5% agar and incubated at 30° C. for two days. A 50 mL test tube containing 5 mL of ½ strength yeast extract, tryptone and sea salt medium (YTSS, per L: 2 g yeast extract, 1.25 g tryptone, 20 g sea salt) was inoculated with each strain and grown overnight at 30° C. on a horizontal rotating drum fermenter. A 500 mL Erlenmeyer flask containing 50 mL of YTSS medium and 0-3 mM pCA was inoculated with 0.5 mL of the overnight culture and incubated at 160 rpm and 30° C. for 3 d. After 3 d, each culture was extracted once with an equal volume of ethyl acetate, dried in vacuo, resuspended in methanol and analyzed by HPLC-MS as described above.

Addition of pCA to YTSS medium led to a drop of pH from 7.5±0.05 to 6.9±0.05. However, Roseobacticide production was independent of the initial pH of the medium: experiments in which the pH of the YTSS medium (+1 mM pCA) was adjusted to 7.5 prior to inoculation with P. gallaeciensis BS107 revealed a similar level of Roseobacticides as those in FIG. 1B (data not shown). The experiments described above were also carried out in Marine Broth (Difco 2216) and in roseobacter minimal medium (Östling, J., et al., 1991, S. FEMS Microbiol. Ecol. 86, 83-94). In the absence of pCA, no Roseobacticides were observed under these conditions, similar to results obtained in YTSS medium (data not shown).

*P. gallaeciensis* cultivated in YTSS medium in the presence of 1 mM pCA for 3 d had an $OD_{650}$ nm that was 17±8% lower than those cultivated in the absence of pCA, as determined from triplicate experiments. The profiles shown in FIG. 1B have not been corrected for the lower cell density observed in the presence of pCA.

Purification of Roseobacticide A and B. The purification of Roseobacticides was carried out in the dark or under dim light. Four L of YTSS medium containing *P. gallaeciensis* BS107 and 1 mM pCA were cultured as described above. After three days, the culture was extracted once with an equal volume of ethyl acetate. The extract was dried over $Na_2SO_4$ and evaporated to dryness in vacuo. The residue was dissolved in $CH_2Cl_2$ and fractionated by flash silica gel chromatography (40 g, d=2.5 cm, l=20 cm). Roseobacticides were eluted with a gradient of 0-20% MeOH in $CH_2Cl_2$. The fractions containing Roseobacticides, as monitored by the distinct broad 430 nm peak by UV-visible spectroscopy, were pooled, dried in vacuo, and purified further by reverse phase HPLC on a preparative Phenomenex C18 column (5 µm, 21.2×250 mm) operating at 12 mL/min using an isocratic elution of 35% of MeCN in H2O, followed by a gradient of 35-100% MeCN in $H_2O$ over 40 min. Roseobacticides A and B were then purified further using a semi-preparative Supelco Discovery HS C18 column (10 µm, 10×250 mm) operating at 3 mL/min with a gradient of 30-100% MeOH in $H_2O$ over 35 min. Roseobacticides A and B were purified to homogeneity by reapplication onto the Supelco Discovery HS C18 column and eluting with the same gradient. This procedure yielded 1.2 mg and 0.2 mg of Roseobacticide A and B, respectively.

Roseobacticide A. TLC($CH_2Cl_2$:MeOH, 92:8 v/v): $R_f$=0.55; UV/vis λmax 262 nm, 432 nm; HRMS (m/z): [M]+ calculated for $C_{16}H_{12}O_3S$, 285.0585. found 285.0578. See Table 2 for NMR data. Roseobacticide B. TLC($CH_2Cl_2$: MeOH, 92:8 v/v): $R_f$=0.58; UV/vis λmax 262 nm, 316 nm, 430 nm; HRMS (m/z): [M]+calculated for $C_{16}H_{12}O_2S$, 269.0637. found 269.0635. See Table 3 for NMR data.

X-Ray Diffraction Analysis of Roseobacticide A

Crystals of Roseobacticide A were grown from a 1:1 mixture of $CH_2Cl_2$/hexanes by slow evaporation. Data on a crystal of Roseobacticide A mounted on a diffractometer was collected at 100 K. The intensities of the reflections were collected using a Bruker APEX II CCD diffractometer ($Mo_{K\alpha}$ radiation, λ=0.71073 Å) equipped with an Oxford Cryosystems nitrogen flow apparatus. The collection method involved 0.5° scans in ω at 26° in 2θ. Data integration down to 0.82 Å resolution was carried out using SAINT V7.23A (Bruker diffractometer, 2005) with reflection spot size optimization. Absorption corrections were made with the program SADABS (Bruker diffractometer, 2005). The structure was solved by the direct method procedure and refined by least-squares methods using SHELXS-97 and SHELXL-97 (Sheldrick, 2000). Non-hydrogen atoms were refined anisotropically, and hydrogen atoms were allowed to ride on the respective atoms. Crystal data as well as details of data collection and refinement are summarized in Table 1.

Assays of Roseobacticide A Against Selected Bacterial Strains

Selected bacterial strains (see Table 4) were tested against Roseobacticide A using the disc diffusion assay (Gauvreau, D. & Waring, M., 1982, J. Appl. Microbiol. Biotechnol. 115: 104-110). Overnight cultures of each test strain in YTSS were diluted 1000-fold into YTSS containing 0.7% agar and poured into standard Petri dish plates. Blank paper discs (8 mm, Fisher Scientific) were loaded with 50 µg of phaeobactin A and placed on top of the agar. The plates were incubated at 30° C. for 12-24 h and the presence or absence of an inhibition zone was monitored visually. Ampicillin (0.5 µg) and MeOH were used as positive and negative controls, respectively. In addition, the assay was carried out in 96 well plates according to the 2003 guidelines of the Clinical and Laboratory Standards Institute (CLSI, formerly NCCLS) with minor changes.

Roseobacters were grown and tested in YTSS medium, *B. subtilis* 3610 in LB, and *P. tunicate* D2 in Marine Broth (Difco 2216). Inocula for each test organism were prepared by suspending a colony from an agar plate into 5 mL of YTSS, LB, or Marine Broth in 15 mL bacterial culture tubes. These were grown overnight, and then adjusted to $1\times10^8$ cells/mL. These cell suspensions were used as inocula for 96 well plate assays: 10 µL of inoculum, corresponding to $1\times10^6$ cells was added to 90 µL of the appropriate medium and supplemented with 10 µL medium (negative control), 10 µL of MeOH (negative control), 10 µL of 0.5 mg/mL, or 0.25 mg/mL of Roseobacticide A. The assay against each test strain was carried out in duplicate. The plate was incubated without shaking for 24 hours at 30° C., and the $OD_{650}$ nm determined on a Molecular Devices 96 well plate reader. No significant difference in $OD_{650}$ nm was observed in wells supplemented with medium vs. those supplemented with MeOH. The $OD_{650}$ nm for the wells containing Roseobacticide A in all each cases was between 80-100% of the value determined for the respective negative controls.

Assays of Roseobacticide A and B Against Selected Algal Strains

The algaecidal effect of Roseobacticide A and B was tested against five axenic microalgae (the Prymnesiophytes *Emiliana huxleyi* (CCMP372) and *Isochrysis* sp. (CCMP468), the green alga *Tetraselmis suecica* (CCMP908), the diatom *Chaetoceros muelleri* (CCMP1318) and the cryptomonad *Rhodomonas salina* (CCMP1319)). All strains were grown on L1 media except for CCMP1318, which was grown in L1+Si (Guillard, R. R. L. & Hargraves, P. E., 1993, Phycologia 32: 234-236). All strains were maintained at 24° C. under 12 h:12 h light:dark illumination.

To perform assays, algal cultures were diluted 1:1 with the medium they were grown in and then 1 mL aliquots were placed in a 48 well microtitre plate and treated with 0.01-0.000000001 mg/mL of Roseobacticide A or B, or alternatively with MeOH solvent, or medium (as controls) and incubated for 24 h at 24° C. under 12 h: 12 h light:dark illumination. Each treatment was monitored microscopically at 2, 12 and 24 h. Cell counts were determined by flow cytometry and compared to the solvent control.

Flow cytometry. For flow cytometry counts, duplicate 0.5 ml samples were fixed with 0.125% (vol/vol) glutaraldehyde in the dark for 10 min. Cells were then frozen in an ethanol dry ice bath and stored at −80° C. until analyzed. Cell concentrations were measured with an EPICS flow cytometer using red fluorescence and forward angle light scattering properties to identify the cells as previously described (Cavender-Bares, K. K., et al., 1998, Limnol. Oceanogr. 43:1383-1388).

Results

One *Roseobacter* genus bacteria, *Phaeobacter gallaeciensis*, associates with marine eukaryotes, including algae, produces the auxin phenylacetic acid, and the potent broad spectrum antibiotics tropodithietic acid (TDA, (1), FIG. 1A) and its valence tautomer thiotropocin (FIGS. 1A and 2) (Rao, D. et al., 2007, supra; Geng, H. F., et al., 2008, R. Appl. Environ. Microbiol. 74, 1535-1545; Thiel, V. et al., 2010, Org. Biomol. Chem. 8, 234-246). However, the fate of this mutualistic *P. gallaeciensis*-alga symbiosis in the presence of a compromised algal host is not known. Here the inventors report that a small molecule generated by compromised algae induces *P. gallaeciensis* BS107 to produce potent but selective phytotoxins that are herein named Roseobacticides A and B.

While not wishing to be bound by theory, it is likely that the initiator of the mutualist-pathogen switch would be produced by compromised algae. As algae senesce, their cell walls deteriorate and breakdown products would be released into the surrounding medium. Since lignin and lignin-like compounds were recently identified as components of red and green algal cell walls (Martone, P. T. et al., 2009, Curr. Biol. 19, 169-175; Delwiche, C. F., et al., 1989, Science 245, 399-401), the lignin breakdown product p-coumaric acid (pCA, FIGS. 1A and 3), which could indicate algal senescence, was tested as a signal. In addition to serving as a small molecule proxy of algal health, pCA has been shown to be taken up by diverse bacteria—including the roseobacter *Silicibacter pomeroyi*—and used to biosynthesize p-coumaroyl-homoserine lactone (pCA-HSL, FIG. 1A, 4), a hybrid signaling molecule that can globally regulate gene expression (Schaefer, A. L. et al., 2008, Nature 454, 595-599).

Figure 1B:
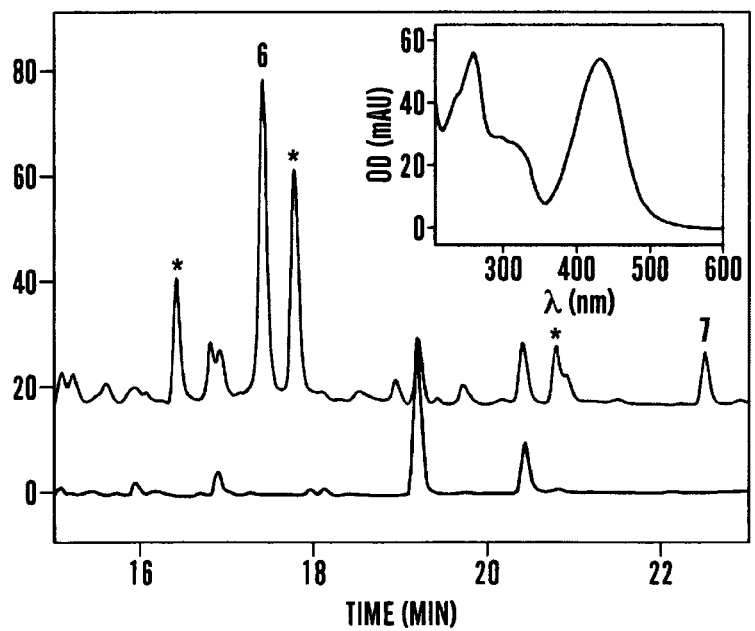
FIG. 1B shows the HPLC-MS profile of the ethanol extract of *P. gallaeciensis* BS107 cultures 72 h after inoculation in the absence (lower trace) and presence (upper trace) of 1 mM pCA. The peaks labeled with asterisks contain the 430 nm absorption feature typical for Roseobacticides. Inset, UV-visible absorbance spectrum of Roseobacticide A (6).
Figure 1C:
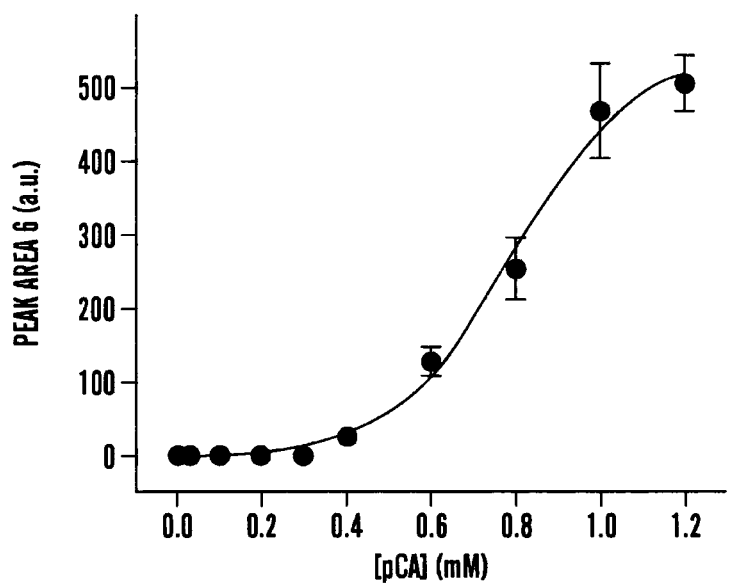
FIG. 1C shows a graph of the dose-response of (6) as a function of [pCA]. Each point is the average of two independent measurements±standard deviation. (a.u., arbitrary units). The line is a dose-response fit and yields an $EC_{50}$ of 0.79±0.03 mM.
Figure 6A:
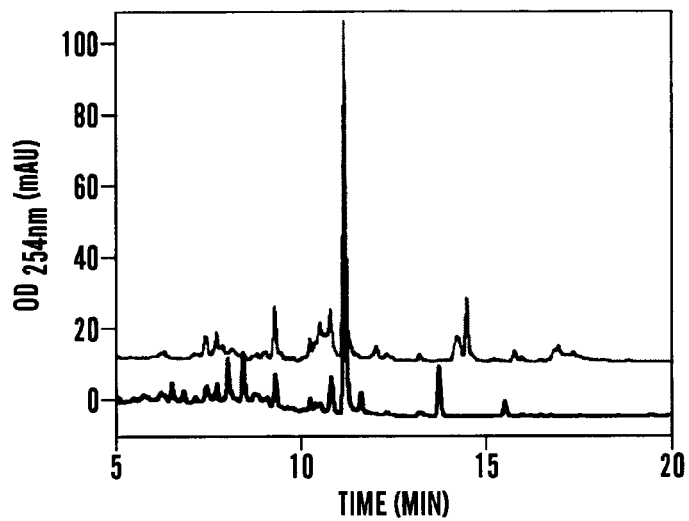
FIG. 6A shows the effect of pCA on *Silicibacter pomeroyi* DSS3 wherein Roseobacticide production is monitored by HPLC-MS. The cultures were grown in the absence (black lower trace) or presence (upper trace) of 1 mM pCA. After three days, they were extracted with ethyl acetate and analyzed. The UV-visible spectra of the small new peaks that are observed only in the presence of pCA in both profiles do not correspond to those of Roseobacticides.
Figure 6B:
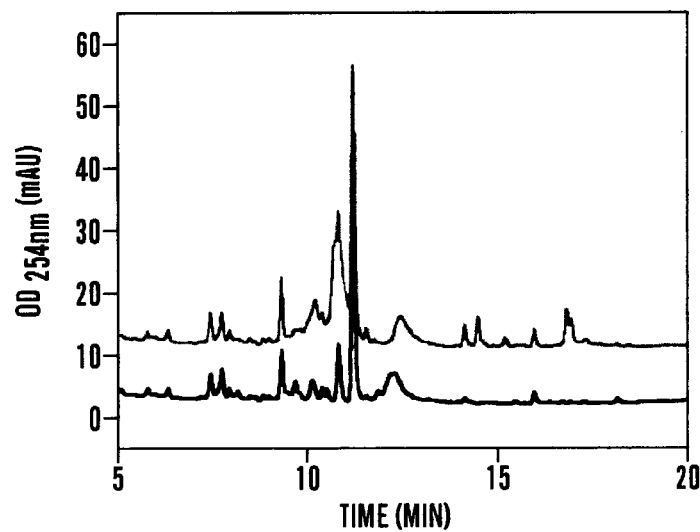
FIG. 6B shows the effect of pCA on *Ruegeria* sp. R11 wherein Roseobacticide production is monitored by HPLC-MS. The cultures were grown in the absence (black lower trace) or presence (upper trace) of 1 mM pCA. After three days, they were extracted with ethyl acetate and analyzed. The UV-visible spectra of the small new peaks that are observed only in the presence of pCA in both profiles do not correspond to those of Roseobacticides.
Figure 7A:
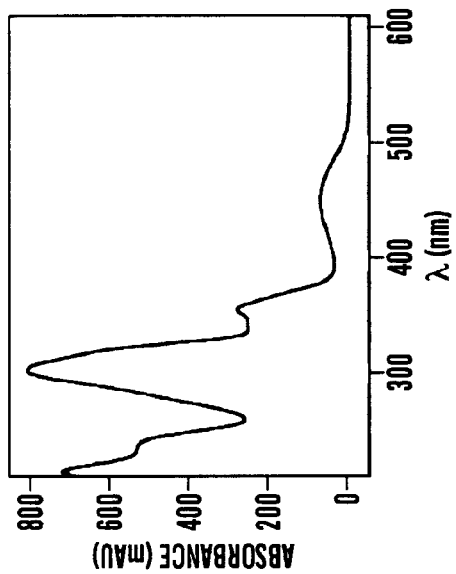
FIG. 7A shows the TDA production by *Phaeobacter gallaeciensis* BS107 grown in the absence of 1 mM pCA for three days, as monitored by HPLC-MS.
Figure 7C:
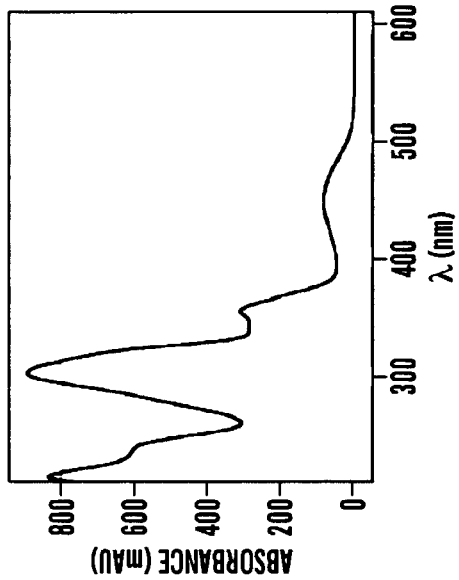
FIG. 7C shows the UV-visible spectra of TDA by *Phaeobacter gallaeciensis* BS107 grown in the absence of 1 mM pCA for three days. The peaks corresponding to TDA are marked.
Figure 7B:
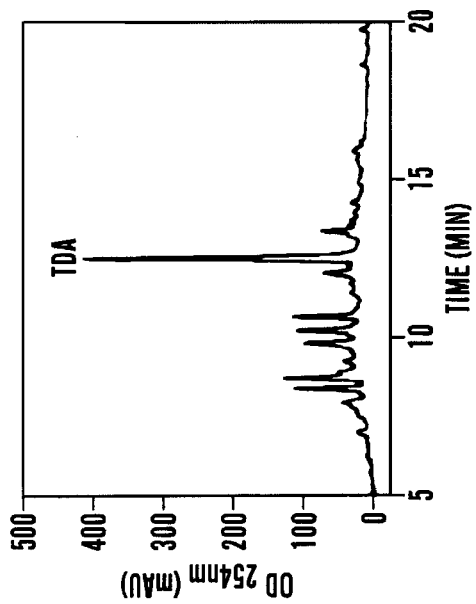
FIG. 7B shows the TDA production by *Phaeobacter gallaeciensis* BS107 grown in the presence of 1 mM pCA for three days, as monitored by HPLC-MS.
Figure 7D:
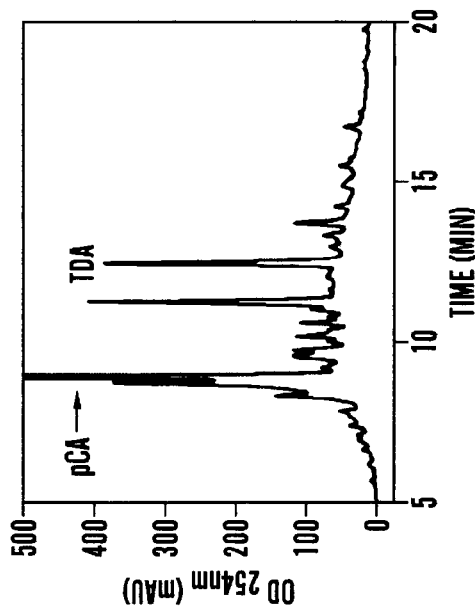
FIG. 7D shows the UV-visible spectra of TDA by *Phaeobacter gallaeciensis* BS107 grown in the presence of 1 mM pCA for three days. The peaks corresponding to TDA are marked.

The inventors cultured three roseobacter strains—*S. pomeroyi* DSS-3, *Ruegeria* sp. R11, and *P. gallaeciensis* BS107—in the presence of varying pCA concentrations (0.1-3 mM). At various time points, the cultures were extracted with ethyl acetate and analyzed by HPLC-MS. The HPLC-MS profiles from *S. pomeroyi* and *Ruegeria* sp. R11 cultures showed no significant pCA-dependent changes (FIG. 6). However, in *P. gallaeciensis* BS107, pCA (1 mM) stimulated the production of a family of compounds characterized by a broad 430 nm peak in the UV-visible spectrum (FIG. 1B). In the absence of pCA, these compounds were not produced by *P. gallaeciensis* under any of the conditions that were investigated. In addition, pCA regulated the production of only selected compounds; it did not, for example, affect TDA (Rosenberg, E., et al., 2007, Nat. Rev. Microbiol. 5, 355-362) production by *P. gallaeciensis* BS107 (FIG. 7).

Figure 2A:
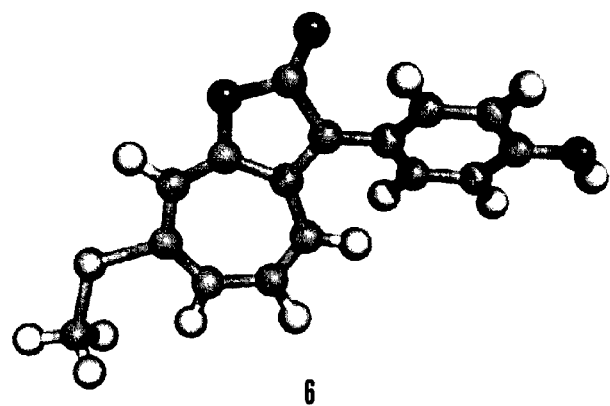
FIG. 2A shows crystal structure of Roseobacticide A solved to 0.82 Å resolution.
Figure 2B:
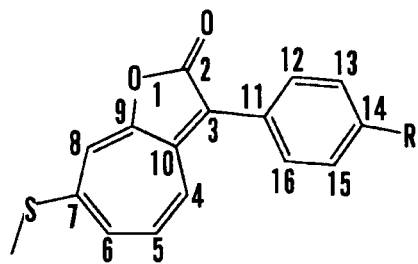
FIG. 2B shows the structures of Roseobacticides A and B and their numbering scheme.
Figure 2C:
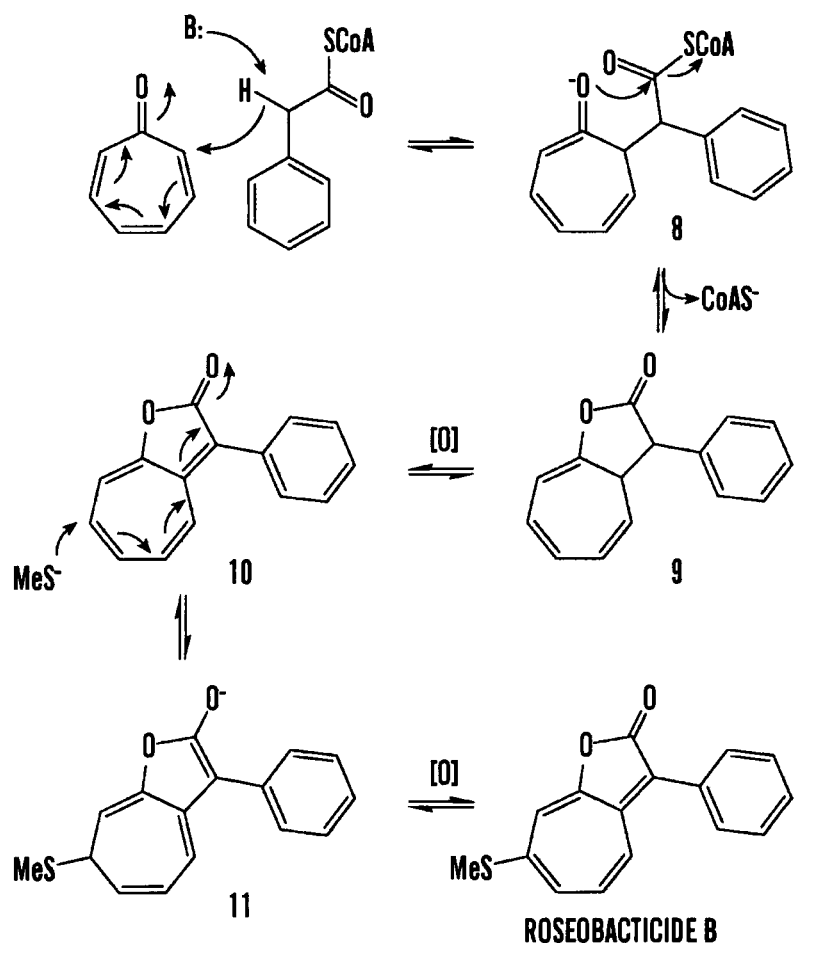
FIG. 2C shows a putative biosynthetic scheme for Roseobacticide B.
Figure 5:
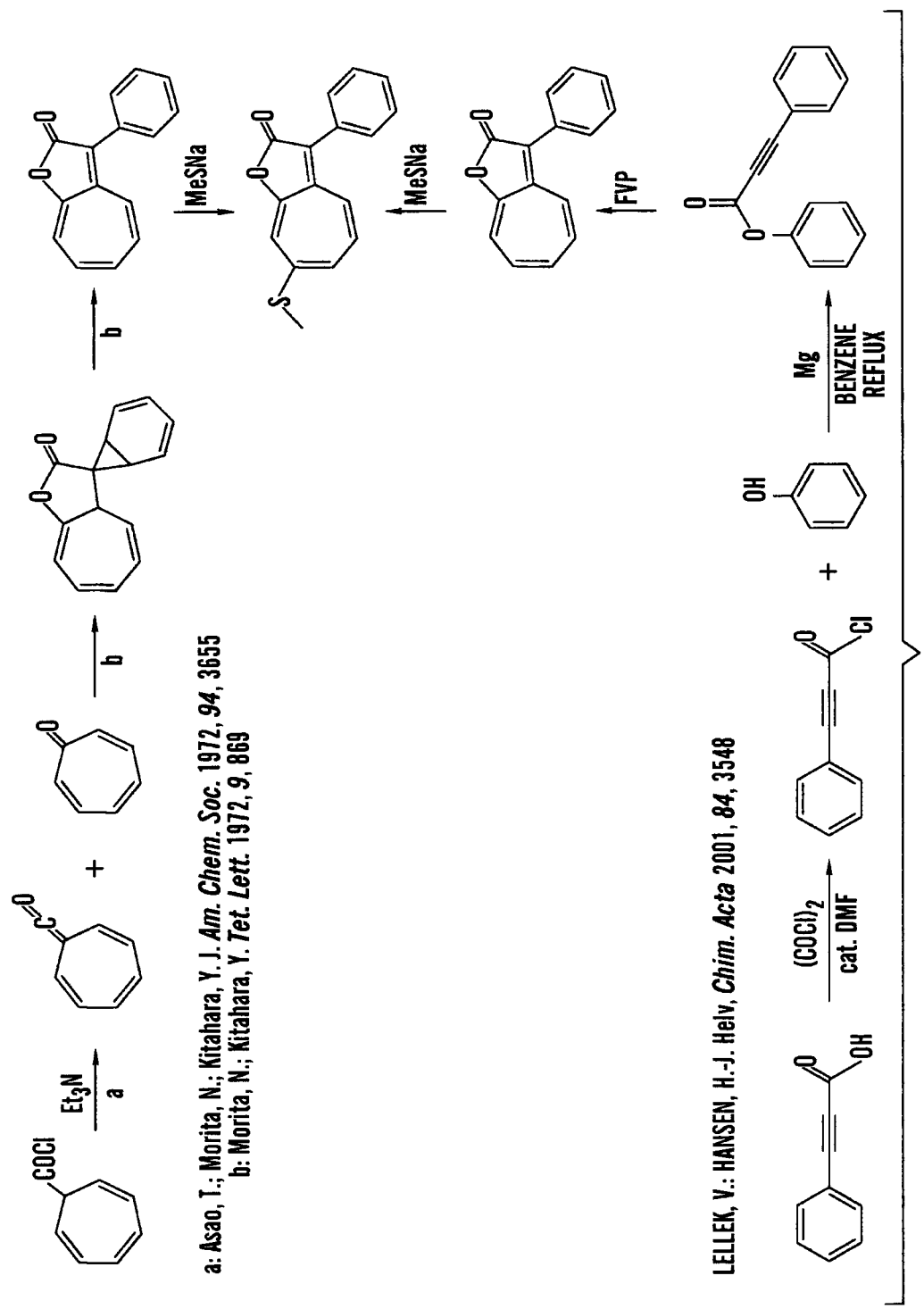
FIG. 5 shows other possible schemes for the chemical synthesis of Roseobacticides.
Figure 8:
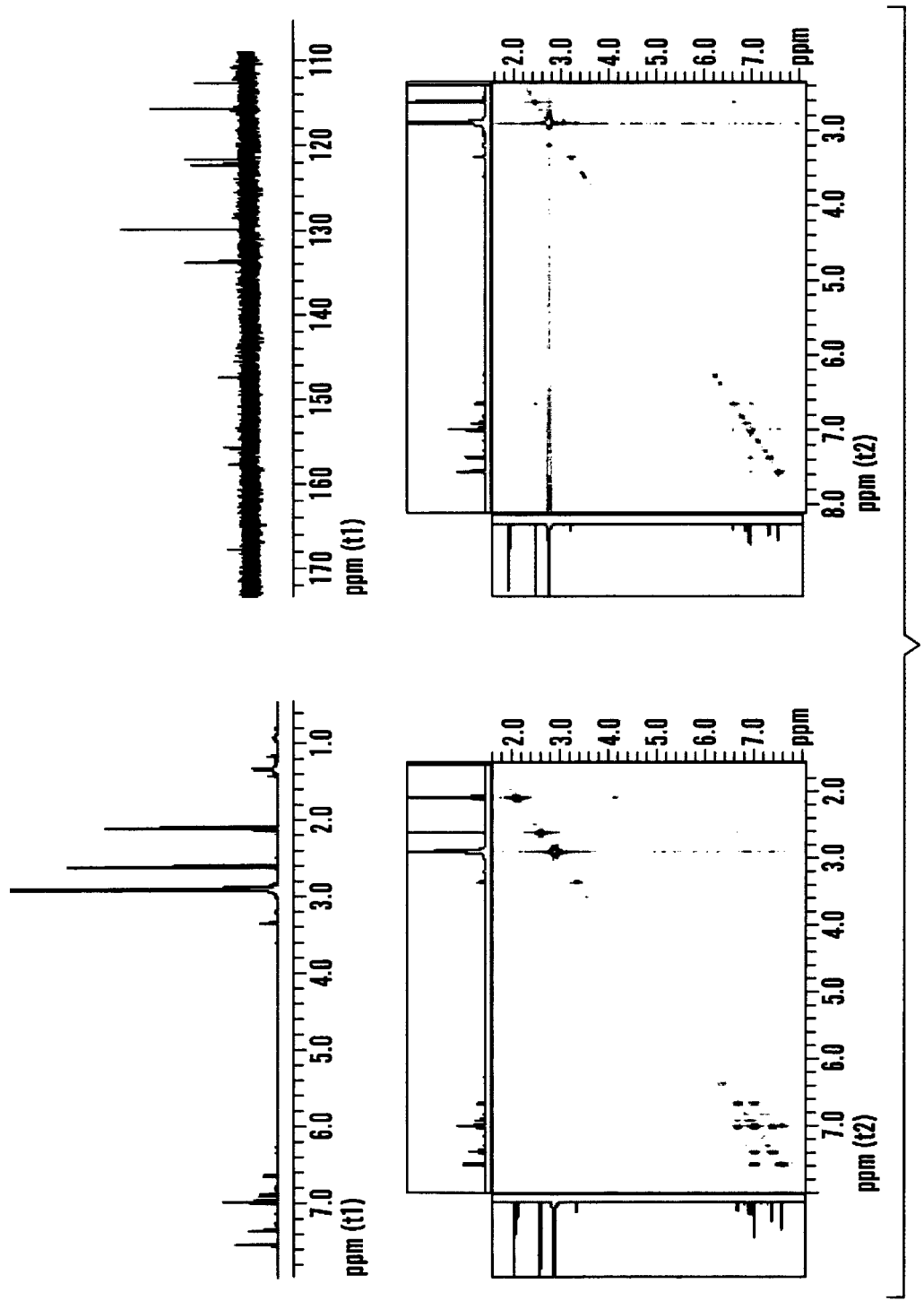
FIG. 8 shows the NMR spectra for Roseobacticide A in $d_6$-acetone. $^1H$ (top left), $^{13}C$ (top right), gCOSY (middle, left), NOESY (middle right), gHSQC (bottom left), and gHMBC (bottom right) spectra are shown. See Table 2 for assignment of the NMR data.
Figure 8:
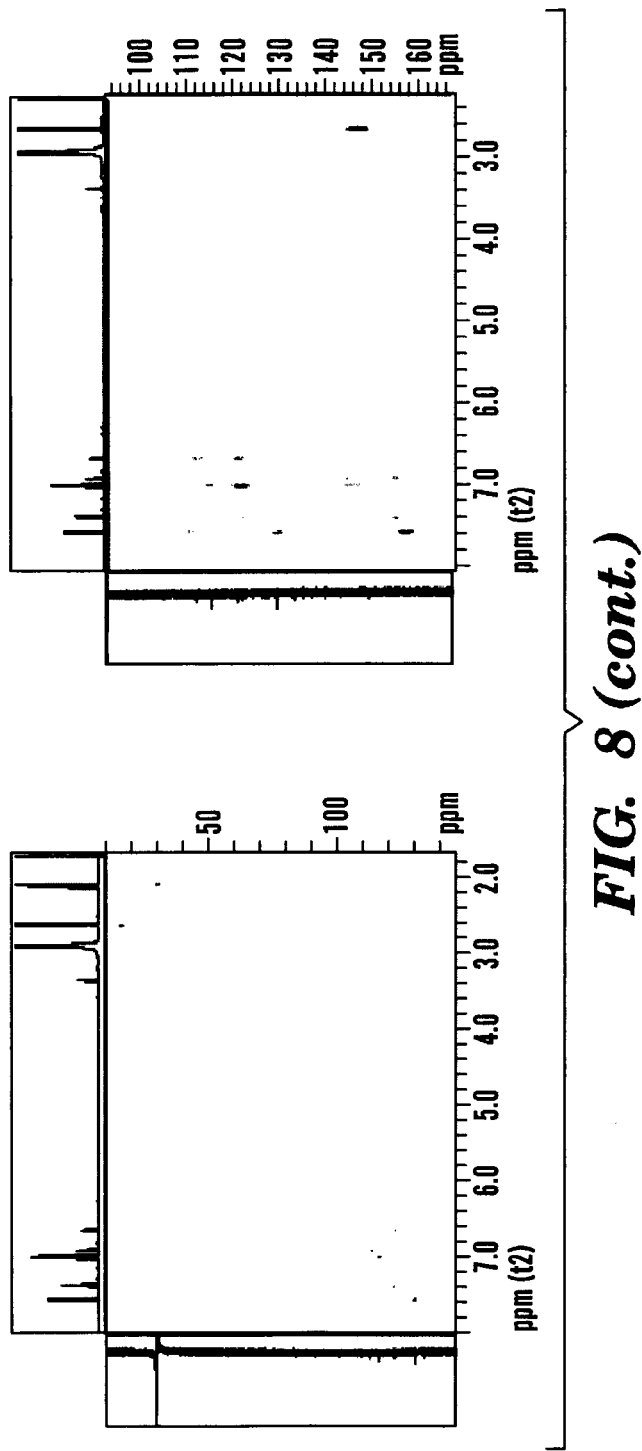
Figure 9A:
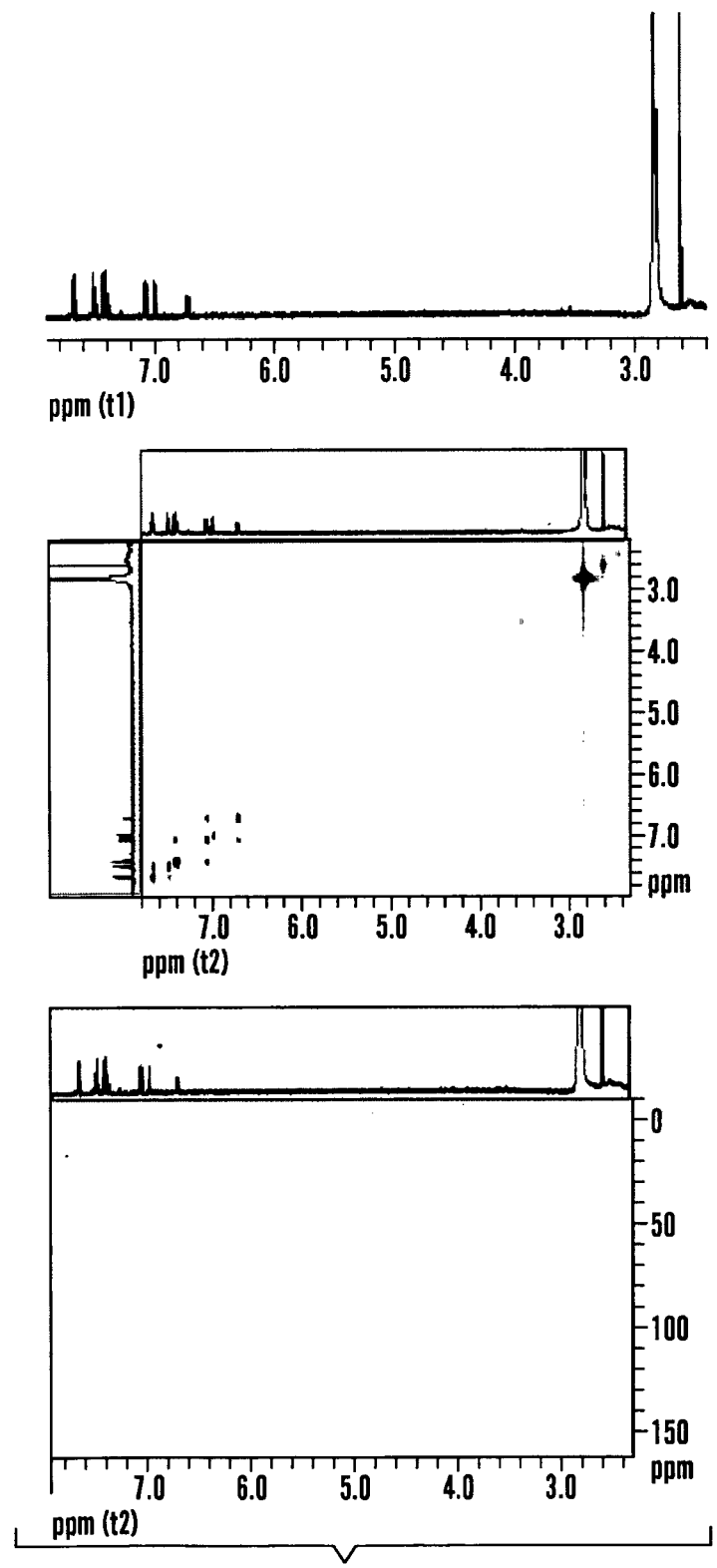
FIG. 9A shows NMR spectra for Roseobacticide B in $d_6$-acetone. $^1H$ (top), gCOSY (middle), and gHSQC (bottom) spectra are shown. See Table 3 for assignment of the NMR data.
Figure 9B:
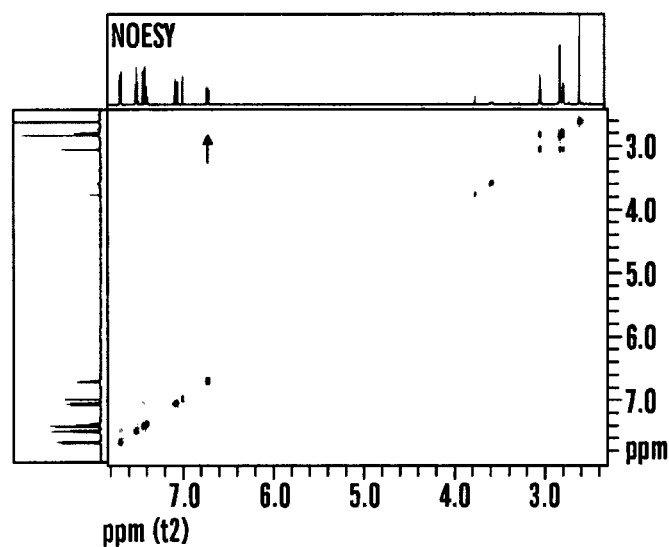
FIG. 9B shows the NOESY NMR spectra for Roseobacticide B in $d_6$-acetone.

To examine the nature of the compounds induced in the presence of pCA further, two compounds were purified to homogeneity from 4 L cultures and named Roseobacticide A (1.2 mg) and Roseobacticide B (0.1 mg), respectively. High resolution MS analysis indicated molecular formulas of $C_{16}H_{12}O_3S$ and $C_{16}H_{12}O_2S$ for Roseobacticide A and B, respectively. The low H/C ratio of 0.75 complicated structural elucidation by NMR methods. Consequently, Roseobacticide A was crystallized by slow evaporation from $CH_2Cl_2$/hexanes and structurally characterized by single crystal X-ray diffraction analysis (Table 1). This analysis provided the backbone connectivity, but some ambiguities in distinguishing C and O atoms remained. The complete structure of Roseobacticide A was finally solved by interpreting $^1H$, $^{13}C$, gCOSY, gHSQC and gHMBC spectra (FIG. 8 & Table 2) in light of the template provided by the X-ray analysis (FIGS. 2A and 5). With the structure of Roseobacticide A in hand, the structure of Roseobacticide B was easily characterized by analyzing 1-D and 2-D NMR data (FIGS. 2B, 6 and 9 & Table 3) Due to limited sample quantities, a gHMBC spectrum was not recorded for Roseobacticide B. The structure was assigned definitively based on $^1H$, gCOSY and gHSQC spectra, HR-MS and the knowledge of the structure of Roseobacticide A. The structures of Roseobacticides A and B have no close relatives among known natural products or synthetic molecules. They share a 1-oxaazulan-2-one bicyclic core with an 8-thiomethyl group and a 3-phenyl or 3-(p-hydroxyphenyl) substituent. The bicyclic part of Roseobacticide A is planar, and its plane is rotated 33° around the C3-C11 bond relative to the plane of the p-hydroxyphenyl substituent (FIG. 2A).

The inventors also investigated how this unusual Roseobacticide core was biosynthesized. Recent reports have noted that tropone, phenylacetic acid and methanethiol are all produced by *P. gallaeciensis* BS107, and these building blocks suggest a model for the biosynthesis of Roseobacticide B (FIG. 2C) (Thiel, V. et al., 2010, Org. Biomol. Chem. 8, 234-246). In this model, tropone undergoes a favored 1,8-addition of the enolate of phenylacetyl-CoA (Rigby, J. H. & Zbur Wilson J., 1984, J. Am. Chem. Soc. 106, 8217-8224; Nair, V., et al., 2006, J. Org. Chem. 71, 8964-8965), to give intermediate 7, followed by lactonization and release of CoA to yield intermediate 8, a formal [8+2] annulation product of the starting substrates. A two-electron oxidation of 8 to 9, followed by 1,8-addition of methanethiol to C7 and another two-electron oxidation yields Roseobacticide B.

The molecules so far uncovered in this symbiosis are a tribute to phenylalanine's versatility, as tropone and phenylacetic acid, potential precursors of the Roseobacticides, are biosynthesized from phenylalanine, as is pCA, the induction signal, and most of the components of cell wall lignin. The conversion of phenylalanine to tropone and to phenylacetic acid has been well documented (Thiel, V. et al., 2010, Org. Biomol. Chem. 8, 234-246; Ismail, W. et al., 2003, Eur. J. Biochem. 270, 3047-3054). The known pathway from phenylalanine to pCA involves phenylalanine ammonia lyase (PAL) and cinnamic acid hydroxylase (MacDonald, M. J. & D'Cunha, G. B., 2007, Biochem. Cell Biol. 85, 273-282; Czichi, U., & Kindl, H., 1975, Planta 125, 115-125). PAL has also been shown to reversibly transform pCA to Tyr (MacDonald, M. J. & D'Cunha, G. B., 2007, supra). An interesting feature of this pathway would be the use of exogenous pCA in the biosynthesis of Roseobacticides. However, the *P. gallaeciensis* genome does not encode a PAL homologue. Alternatively, pCA may be converted to pCA-HSL (Schaefer, A. L. et al., 2008, Nature 454, 595-599), which could in turn signal the induction of the genes comprising the Roseobacticide biosynthetic pathway (Schaefer, A. L. et al., 2008, Nature 454, 595-599; Lee, Y.-W., et al., 1996, Gene 179, 83-88).

Figure 3C:
FIG. 3A-3C shows the algaecidal activity of Roseobacticide A against *Emiliana huxleyi*. *E. huxleyi* was exposed to methanol (solvent control) for 24 hr (FIG. 3A) and to 3.5 µM Roseobacticide A for 12 hr (FIG. 3B) and 24 hr (FIG. 3C). Panels contain live samples viewed by light microscopy and are typical of the three experiments; scale bar=2 µm.
Figure 3B:
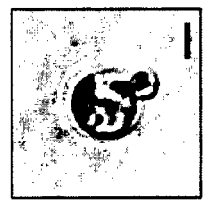
Figure 3A:
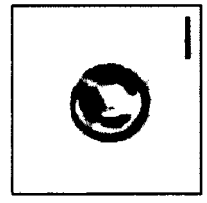
Figure 4:
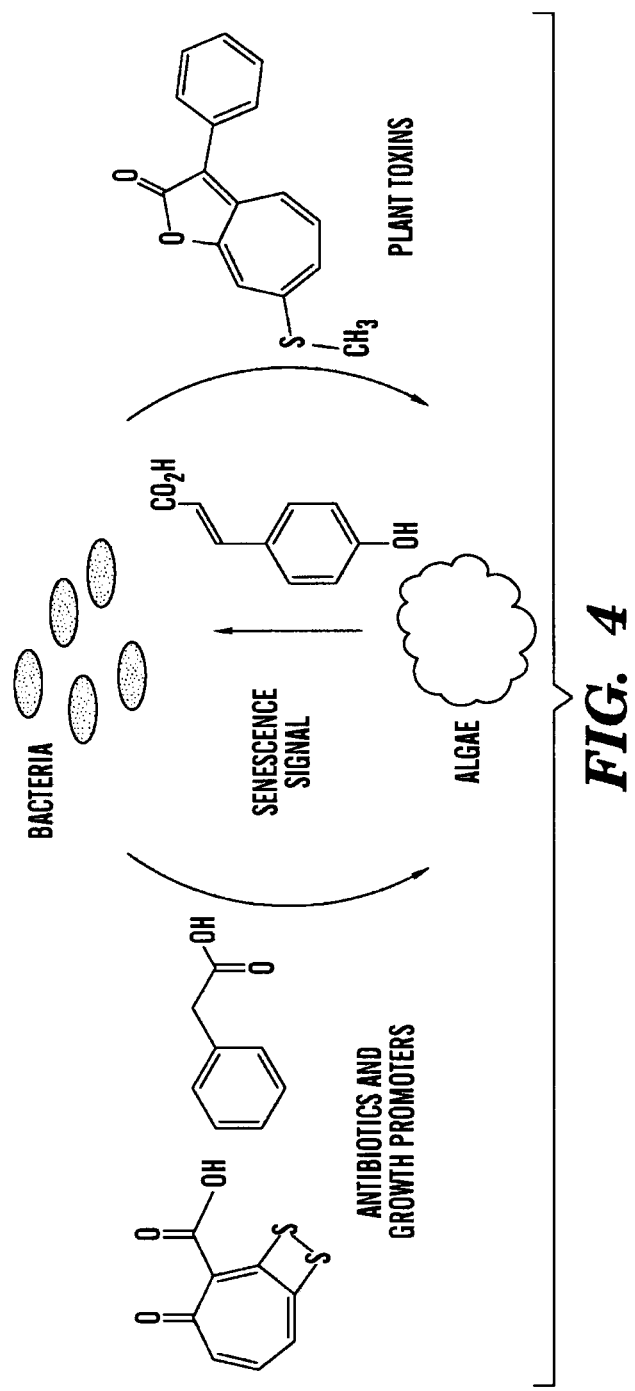
FIG. 4 is a graphical representation of the symbiotic relationship between the bacteria and algae.
Figure 10A:
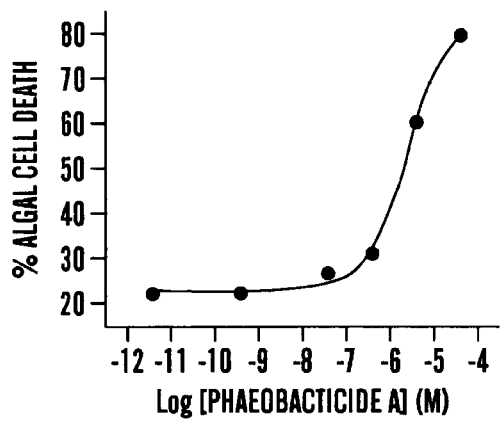
FIG. 10A shows the dose response curve of Roseobacticide A against *Emiliana huxleyi*. The data (black dots) were fitted to a standard dose-response equation (line) yielding $IC_{50}$ values of ≥2.2 µM. Microscopy showed that 20% of the algal cell population are damaged yet intact at the lowest Roseobacticide concentration tested but the loss of chlorophyll places them outside the gated algal population (micrographs not shown).
Figure 10B:
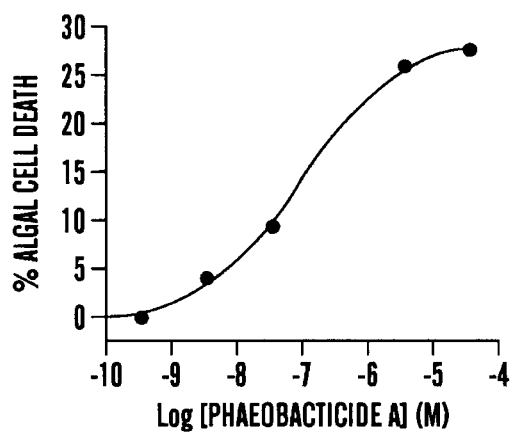
FIG. 10B shows the dose response curve of Roseobacticide A against *Rhodomonas salani*. The data (black dots) were fitted to a standard dose-response equation (line) yielding $IC_{50}$ values of ≥0.10 μM. Only a subpopulation appears to be susceptible to Roseobacticide A (micrographs not shown).
Figure 10C:
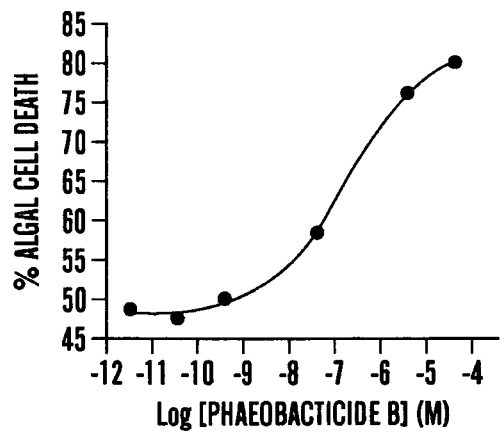
FIG. 10C shows the dose response curve of Roseobacticide B against against *E. huxleyi*. The data (black dots) were fitted to a standard dose-response equation (line) yielding $IC_{50}$ values of ≥0.19 μM. Microscopy showed that 48% of the algal cell population are damaged yet intact at the lowest Roseobacticide concentration tested but the loss of chlorophyll places them outside the gated algal population (micrographs not shown).
Figure 11B:
FIG. 11B shows the effect of Roseobacticide A on *Chaetoceros muelleri* cell shape in the presence of 3.5 μM Roseobacticide A after 24 h.
Figure 11A:
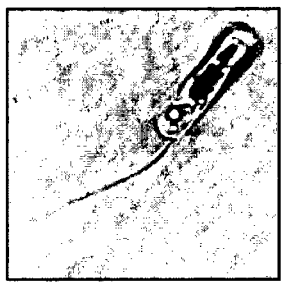
FIG. 11A shows the effect of Roseobacticide A on *Chaetoceros muelleri* cell shape in the absence of 3.5 μM Roseobacticide A after 24 h.
Figure 12D:
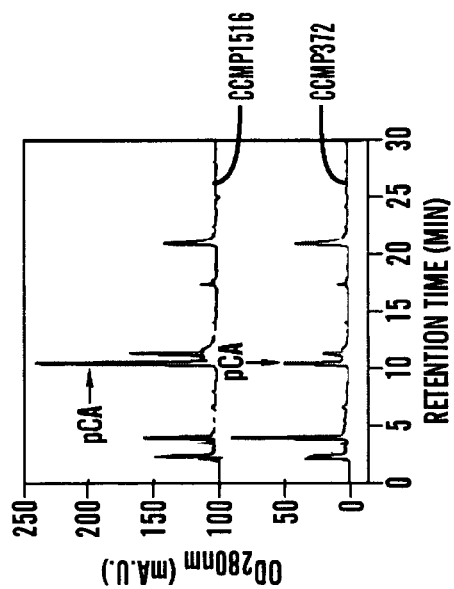
Figure 12B:
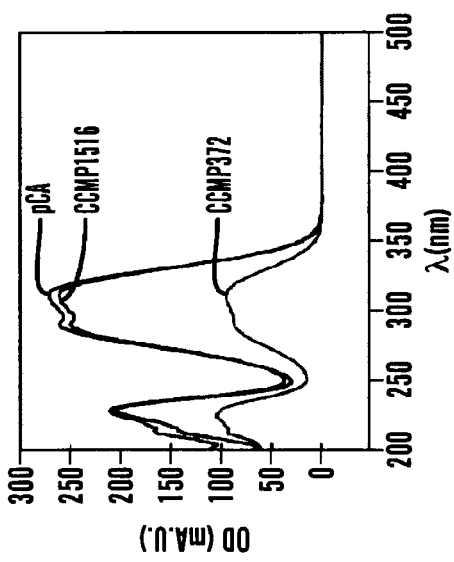

To determine their role in mediating the roseobacter-algal symbiosis, the effects of Roseobacticides on bacteria and microalgae were tested. The half-maximal inhibitory concentration ($IC_{50}$) was determined against a panel of marine bacteria and *B. subtilis* 3610, however, no significant antibacterial activity was detected ($IC_{50}>0.16$ mM, Table 4). Assays against a diverse selection of microalgae (the Prymnesiophytes *Emiliana huxleyi* and *Isochrysis* sp., the green alga *Tetraselmis suecica*, the diatom *Chaetoceros muelleri* and the cryptomonad *Rhodomonas salina*) showed that Roseobacticides had specific and potent algaecidal activity. Incubation of *E. huxleyi* with Roseobacticide A and B resulted in cell lysis after 24 h, with cellular damage visible after 12 h (FIG. 3). The loss of chloroplasts suggests that Roseobacticides may be acting directly on the chloroplast or that they are inducing apoptosis causing loss of cellular integrity. The $IC_{50}$s were determined by flow cytometry as it allowed thousands of cells to be rapidly counted for each concentration of Roseobacticide tested. Roseobacticide A showed an $IC_{50}$ of ≥2.2 μM and 0.10 μM against *E. huxleyi* and *R. salina*, respectively (FIG. 10 & Table 4). The other three algal strains were less susceptible with $IC_{50}$s>35 μM, though *C. muelleri* showed major morphological changes upon incubation with Roseobacticide A (FIG. 11). Roseobacticide B was only tested against *E. huxleyi* yielding an $IC_{50}$ of 0.19 μM (FIG. 10). Based on the recovered amounts of 6 and 7, their bulk solution concentration in the 41 cultures would be ~1 μM and 0.2 μM, respectively. However, the concentration encountered by the algal host with a bacterial biofilm cannot be accurately determined.

The production of pCA and dimethylsulfoniopropionate (DMSP; a major algal metabolite that some roseobacters, including *P. gallaeciensis*, can use as a sole C and S source) by other micro- and macroalgae, and by terrestrial plants found in the marine environment, suggests that *P. gallaeciensis* may interact with a variety of hosts in the ocean. Although there is no direct evidence for a naturally occurring *E. huxleyi-P. gallaeciensis* symbiosis, several observations suggest that they may interact. Their geographic ranges overlap, as they have both been isolated from the same sites (the North Sea and the Tasman Sea). In addition, *E. huxleyi* is a prolific producer of DMSP, which *P. gallaeciensis* can take up and transform. Finally, the diverse primary and secondary metabolism of *P. gallaeciensis* and its quorum sensing and biofilm-forming repertoire imply host interactions in agreement with the isolation of *Phaeobacter* spp. from a range of marine eukaryotes and algae.

Figure 13:
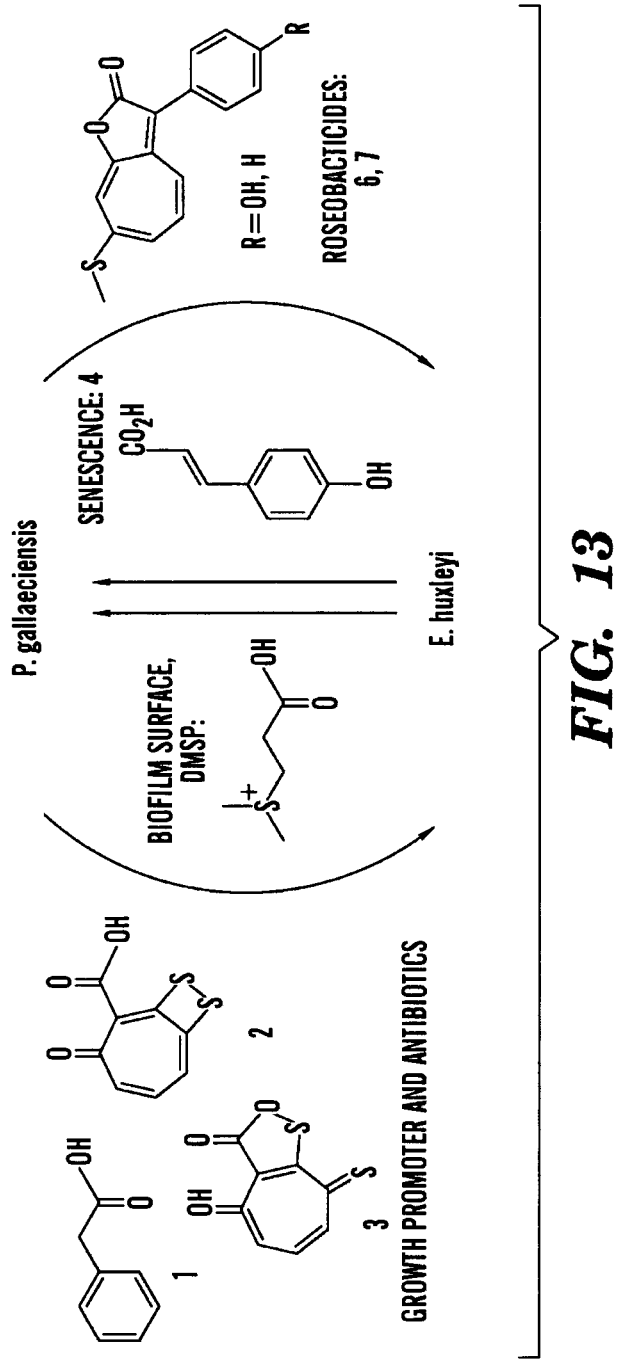
FIG. 13 shows the proposed working model for the interaction between *E. huxleyi* and *P. gallaciensis*. In the mutualistic phase, *E. huxleyi* is healthy and provides DMSP and a biofilm surface to *P. gallaeciensis*, which in turn produces algal growth promoters and antibiotics (1-3) to protect *E. huxleyi*. The interaction turns pathogenic when *E. huxleyi* senesces and releases the algal breakdown product 4, which induces *P. gallaeciensis* to produce the potent algaecides 6 and 7.

The most parsimonious explanation for the findings described herein is that there are two distinct phases in the *P. gallaeciensis*-algal interaction (FIG. 13).

The fact that Roseobacticides are antialgals produced in response to pCA argues that they modulate the *P. gallaeciensis*-algal symbiosis. When the algal host is healthy, the symbiosis is mutualistic with *P. gallaeciensis* producing the TDA antibiotic, to protect the algal host, and phenylacetic acid, a plant growth promoter (Thiel, V. et al., 2010, Org. Biomol. Chem. 8, 234-246; Ashen, J. B., et al., 1999, J. Phycol. 35, 493-500; Ashen, J. B. & Goff, L., 1996, J. J. Phycol. 32, 286-297). But when algal cells begin to senesce and release pCA, *P. gallaeciensis* is induced to produce the Roseobacticides and the interaction becomes parasitic. The shift could redirect tropone, which *P. gallaeciensis* produce as a TDA precursor, and phenylacetic acid to form Roseobacticides A and B, which kill the algae—a shift of health- and growth-promoting small molecules into toxins. The commonality in using phenylacetic acid as an auxin and as a potential precursor in the synthesis of an algaecide may provide an important regulatory switch in converting *P. gallaeciensis* from a mutualist to a parasite. This shift in the symbiosis may occur to allow *P. gallaeciensis* to secure the plentiful food sources provided by the aging algal cells. Alternatively, it may provide *P. gallaeciensis* with a selective advantage allowing them to rapidly dissociate from a dying host, disperse, and re-associate with healthy algae elsewhere. The peak in roseobacter abundance observed at the conclusion of blooms supports both scenarios (Gonzalez, J. M. et al., 2000; Appl. Environ. Microbiol. 66, 4237-4246; Lamy, D. et al., 2009, Aquat. Microb. Ecol. 58, 95-107).

Example 2

Determination of the Inhibition of Algae Growth

The cells of an algae species can be cultivated for several generations in any defined medium known in the art that will support growth of the algae. The algicide, Roseobacticide A-EE or a compound comprising the formula I described herein is then added in various concentrations. Chlorohexidine (=CHD) can be tested in comparison to Roseobacticide A-EE or a compound comprising the formula I described herein used a positive control. A control free of algicide is also included in the experiment. The Roseobacticide A-EE or a compound comprising the formula I described herein can be used in all of the examples herein (Examples 2-5) as a 0.5-1 mg/mL solution or ~0.05-0.1% weight/vol.

The test batch can be produced by mixing appropriate amounts of nutrient solution concentrate, water, stock solution of the test algicide and inoculation (seed) material of an exponentially growing alga culture. The alga genera used in the test can be found in any conceivable location, to wit, on the ground, on moist flower pots, in standing and flowing water, on moist rocks and even in the air. The present invention is not limited to the specific alga species utilized herein. Whether a specific alga species is susceptible to treatment by the algaecide of present invention can be easily determined by simply repeating the examples herein using the alga species to be tested for susceptibility.

The test batches can be incubated for a minimum time of 72 h during which the cell number was determined every 24 h.

The inhibition is measured as a reduction of the growth in comparison to a control culture grown under identical conditions. The control culture can be a culture which has not been treated with a test algicide, e.g., a culture treated with a buffer solution or diluted nutrient solution.

Example 3

Determination of the Algicidal Activity in the Suspension Test

The cells of the alga species are cultivated several days on inclined alga tubes in any defined medium known in the art that will support growth of the algae and washed off for the test with the defined medium used for culture.

The test algicide: Roseobacticide A-EE or a compound comprising the formula I, is produced by mixing appropriate amounts of nutrient solution, water stock solution of the test substance and inoculation material of the alga culture.

The test batches are then incubated 14 days at room temperature under exposure to light (24 hours/day (=h/d) in each instance) and evaluated visually daily in comparison to the control cultures.

The spectrum of activity and spectrum of intensity of the alga culture in comparison to the control cultures indicate the strength of the algicidal activity of the test algicide. Typical observations include lysis of algal cells, decomposition of the entire chlorophyll, water color shifts from green to colorless; and no more changes recognizable in the further course of the test, that is, no cell division of the algae are visible any more.

Example 4

Test in a Test Basin (15 m$^3$)

Roseobacticide A-EE or a compound comprising the formula I can be added to greenish and turbid pond water containing algae. Appearance of the water is then observed with time, after 24 hrs, 2 days, 1 week and 2 weeks. Initially, the water appearance after 24 hr should be clear and not turbid. After 3 weeks, slight alga growth may be recognizable.

The references cited herein and throughout the specification are incorporated herein by reference.

Example 5

Roseobacticides: Small Molecule Modulators of an Algal-Bacterial Symbiosis

Marine bacteria and microalgae engage in dynamic symbioses mediated by small molecules. As described in Example 1, an algal senescence signal produced by E. huxleyi elicits the production of novel algaecides, the roseobacticides, from the bacterial symbiont. By expanding the number of elicitors, nine new members of the roseobacticide family, rare bacterial troponoids, were identified, providing insights into both their biological roles and their biosynthesis. The qualitative and quantitative changes in the levels of roseobacticides induced by the additional elicitors and the elicitors' varied efficiencies support the concept of host-targeted roseobacticide production. Structures of the new family members arise from variable substituents at the C3 and C7 positions of the roseobacticide core as the diversifying elements and suggest that the roseobacticides result from modifications and combinations of aromatic amino acids. Together these studies support a model in which algal senescence converts a mutualistic bacterial symbiont into an opportunistic pathogen of its host(s).

Investigating the chemistry underlying microbial symbioses provides opportunities to discover new small molecules in the context of the biological roles they have evolved to fulfill.[1] Described elsewhere herein are roseobacticides A and B (FIG. 14, 6, 7), which contain the previously unreported 1-oxaazulan-2-one core, and their ability to affect marine phytoplankton with nM potency. The bacterial symbiont that produces these roseobacticides, Phaeobacter gallaeciensis BS107,[3] belongs to the roseobacter clade, a large group of marine α-proteobacteria that can account for up to 25% of all bacteria in typical coastal communities.[4] P. gallaeciensis BS107 is easily cultured in the laboratory. Under these conditions, it produces a number of secondary metabolites including the antibiotic tropodithietic acid (2), its precursor 12, and the plant growth promoter phenylacetic acid (1).[5] P. gallaeciensis BS107 associates with Emiliania huxleyi, a globally distributed single-celled microalga covered with ornate $CaCO_3$ disks.[2,6] E. huxleyi is a major contributor (80-90%) to massive (104-105 $km^2$) seasonal algal blooms that are easily visible in satellite images, and it, along with other microphytoplankton, produces nearly half of the Earth's atmospheric oxygen.[7] In addition to fixing $CO_2$ through photosynthesis, E. huxleyi sequesters $CO_2$ in the $CaCO_3$ disks that surround each algal cell, and also plays a role in the global sulfur cycle by reducing dissolved sulfate to methionine, cysteine, and dimethylsulfoniopropionate (DMSP, 13).[8] DMSP attracts roseobacter (and other) bacteria, which use it as a carbon and sulfur source.[9] The bacteria metabolize DMSP to volatile DMS, which in the atmosphere is converted to condensation nuclei for water droplets.[4,10] Thus, roseobacter-microalgal symbioses play key roles in important biogeochemical processes.[4,11]

Numerous studies had shown that the symbiosis between bacteria in the roseobacter clade, like P. gallaeciensis BS107, and microphytoplankton, like E. huxleyi, were dynamic, that is, the partners were at times attracted to and at other times repelled by one another.[12,13] Recent findings indicated that terrestrial plant-associated bacteria can detect monomeric components of the heteropolymer lignin that are released into the surrounding soil when plants senesce and generate quorum-sensing signals in response.[14] As lignin components have been identified in green, red and brown algae, it was plausible that marine bacteria associated with algae might be responsive to lignin-related signals[15]. Examination of E. huxleyi, a member of the haptophytes and thus a precursor to the green algal lineage, revealed production of significant quantities of p-coumaric acid (pCA, 14), making E. huxleyi the first haptophyte shown to produce lignin components.[2] In addition, it is demonstrated herein that P. gallaeciensis BS107 responds to pCA by producing, instead of quorum-sensing signal molecules, a class of potent algicides, herein referred to as the roseobacticides, that kill E. huxleyi, and affect two other microalgal strains at nM concentrations.

Figure 14:
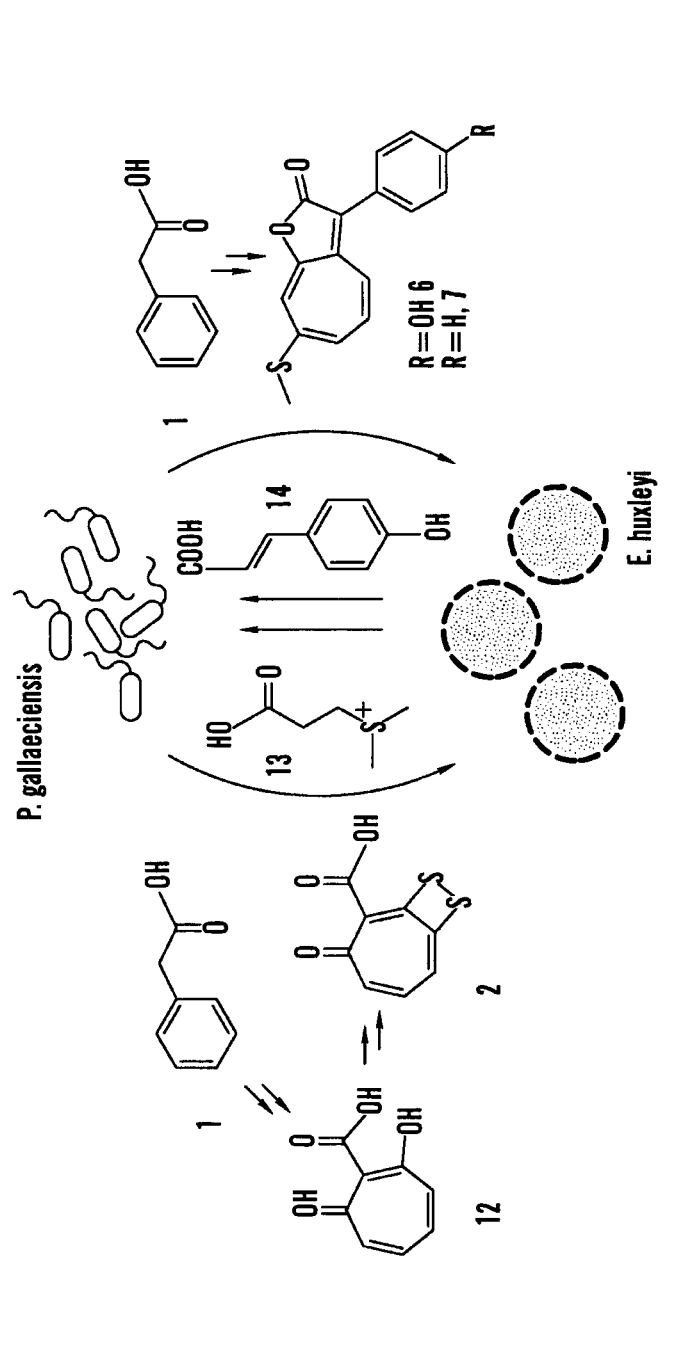
FIG. 14 depicts a proposed model for the interaction between *P. gallaeciensis* B107 and *E. huxleyi*. The two phases of the interaction are shown on the left (mutualistic) and on the right (pathogenic). In the mutualistic phase, *E. huxleyi* provides DMSP (13) and an attachment surface, and the bacterial symbiont provides growth promoter (1) and the antibiotic TDA (2), which is biosynthesized from precursor (12). When *E. huxleyi* senseces, it releases pCA (14), which elicits production of the anti-algal compounds, the roseobactidcides (6, 7), likely derived from (1).

These results led to the model shown in FIG. 14. In this model, the interaction is mutualistic when the algal host is healthy. The host provides the bacteria a solid surface along with a C- and S-source (13).[16] In return, the bacteria produce antibiotic 2 to protect the host from bacterial pathogens and growth promoter 1. The relationship changes when the host senesces, as signaled by the release of pCA into the environment, which causes the bacteria to produce roseobacticides. This switch from mutualist to pathogen allows the bacteria to secure the plentiful food supply provided by the dying host and to associate with healthy algae elsewhere in the bloom. The bacteria's behavioral change corresponds to a metabolic switch since the core of the roseobacticides can, in principle, be formed by joining the building block of antibiotic 2 and growth promoter 1—a switch transforming molecules that facilitate algal growth to potent and selective phytotoxins.

The inventors examined a larger panel of elicitors, which led to a dramatic expansion of the roseobacticide family through complex quantitative and qualitative changes in bacterial metabolism. The study is expanded to include other members of the roseobacter clade and their responses to the larger panel of elicitors.

Materials and Methods

Materials and Strains.

Figure 15:
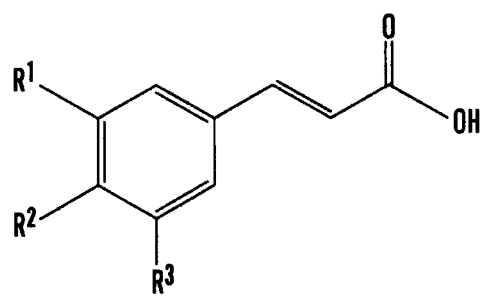
FIG. 15 depicts lignin precursors or breakdown products examined as elicitors of roseobacticide production in this work.

Candidate elicitors 14-18 (FIG. 15) and sea salt used for preparation of culture media were obtained from Sigma-Aldrich. Other media components were from Becton-Dickinson.

General Procedures.

HPLC purifications were carried out on an Agilent 1200 Series analytical or preparative HPLC system equipped with a photodiode array detector. Low resolution HPLC-MS analysis was performed on the same analytical system equipped with a 6130 Series ESI mass spectrometer using an analytical Phenomenex Luna C18 column (5 µm, 4.6×100 mm) operating at 0.7 mL/min with a gradient of 30% MeCN in H2O to 100% MeCN over 20 min. High resolution HPLC-ESI-MS and tandem MS were carried out on an Agilent 1200 Series HPLC equipped with a photodiode array detector and a 6520 Series LC/Q-TOF using the same column and gradient as above. HR-MS and tandem MS were calibrated to within 3 ppm and 12 ppm, respectively. $^1H$, $^{13}C$ and $^2D$ NMR spectra were recorded in the inverse-detection probe of a Varian Inova spectrometer (600 MHz for 1H, 150 MHz for 13C). Chemical shifts were referenced to the residual solvent peaks in acetone-d6 or methanol-$d_4$.

Cultivation of Roseobacter Strains.

Preparative-scale (2-8 L) cultivation of P. gallaeciensis BS107 (or other roseobacter strains) was carried out in half-strength yeast extract-tryptonesea salt (YTSS) medium, which consists of (per L): 20 g Sigma sea salt, 2 g yeast extract, and 1.25 g tryptone. P. gallaeciensis BS107 (or other roseobacter strains) were streaked out from frozen culture stocks and maintained on Marine Broth agar plates (Difco 2216) at 30° C. Overnight cultures were initiated by inoculating 5 mL YTSS medium in 15 mL culture tubes and shaking these overnight at 250 rpm and 30° C. A 0.5 L Erlenmeyer flask containing 50 mL YTSS medium was inoculated with 0.5 mL of the overnight culture and grown for 12-18 h at 30° C. and 160 rpm. Large 4 L Erlenmeyer flasks, each containing 0.4 L YTSS medium, were inoculated with 4 mL of the overnight culture and supplemented with 1 mM of each of the elicitors (14-18). The cultures were grown for 3 d at 30° C. and roseobacticides purified as described below.

Elicitor Dose-Response Analysis.

Eight to ten 0.25 L Erlenmeyer flasks each containing 25 mL of YTSS medium and a range of elicitor concentrations (between 0 and 1.2 mM) were inoculated with 0.25 mL of an overnight *P. gallaeciensis* BS107 culture prepared as described above. These were grown at 30° C. and 160 rpm. After 3 d, each culture was extracted twice with 25 mL of EtOAc. The organic phase was combined, dried over $Na_2SO_4$, and subsequently dried in vacuo. The residue was resuspended in 0.3 mL MeOH and analyzed by HPLC-MS as described above. The amount of roseobacticide B (7) produced, which was quantified by massion extraction ($[M+H]^+$=269), was plotted against the concentration of the elicitor. The maximal amount of 7 was normalized to 100%, and the $EC_{50}$, the elicitor concentration where production of 7 was half-maximal, was obtained by fitting the data to equation 1, where $B_{max}$ and $B_{min}$ are the maximal (~100%) and minimal (~0%) amounts of 7 and p is a Hill slope parameter to account for variations in the slope. $B_{max}$ and $B_{min}$ were allowed to vary to obtain the optimal fit as judged by the $R^2$ correlation value.

$$\text{Amount of } 7 = B_{min} + \frac{B_{max} - B_{min}}{1 + 10^{((EC_{50} - [elicitor]) \times p)}} \quad (1)$$

Purification of Roseobacticides.

After 3 d, the large-scale cultures were extracted twice with an equal volume of EtOAc. The organic phase was combined, dried over $Na_2SO_4$, and subsequently dried in vacuo. The residue was weighed, resuspended in a small volume of MeOH, mixed with a 3-fold excess of Celite (by weight), and dry-loaded onto a C18-functionalized silica gel column (~3 g, d=15 mm, 1=40 mm), which had been equilibrated in 15% MeCN in $H_2O$. The column was then washed with 10 column volumes (CV) of 15% MeCN, and roseobacticides eluted with a step gradient of 10 CV of 30% MeCN, 10 CV of 75% MeCN, which contained roseobacticides, and 10 CV of 100% MeCN. The 75% MeCN fraction was dried in vacuo and purified on a preparative Phenomenex Phenyl-Hexyl column (5 μm, 21.2×250 mm) operating at 12 mL/min with a gradient of 40% MeCN in H2O to 100% MeCN over 40 min. Fractions, which contained roseobacticides, as judged by their UV-visible spectra and by analytical HPLC-MS, were further purified on a semi-preparative Agilent Eclipse XDB-C8 column (5 μm, 9.4×250 mm) operating at 3 mL/min using a gradient of 35% MeCN in H2O to 80% MeCN over 40 min. Reapplication of the material onto the same column (or a Supelco Discovery C18 column (10 μm, 10×250 mm) or a Phenomenex Luna Phenyl-Hexyl column (5 μm, 10×250 mm), depending on the roseobacticide) using the same flow rate and gradient afforded pure material.

Structural Elucidation.

Structures of roseobacticides were elucidated using standard 1D ($^1$H and $^{13}$C) and 2D (gCOSY, gHSQC, gHMBC, NOESY) NMR spectra. In addition, HRMS and tandem MS were utilized as described above. $^1$H NMR spectra, tables of $^2$D NMR data, HR-MS and tandem MS results for each compound are shown in FIGS. 21-30 and Tables 7-16. Degradation analysis for 20-22, 26, and 27 was carried out by incubating a small amount of each compound (~100 μL, ~5 μg) with 5 mM (~10 μL) of the disulfide reducing agent dithiothreitol in MeOH for 1-3 h at room temperature, followed by analysis of the reaction products (~50 μL) by HPLC-MS as described above.

Results

Additional Roseobacticide Elicitors.

Figure 20B:
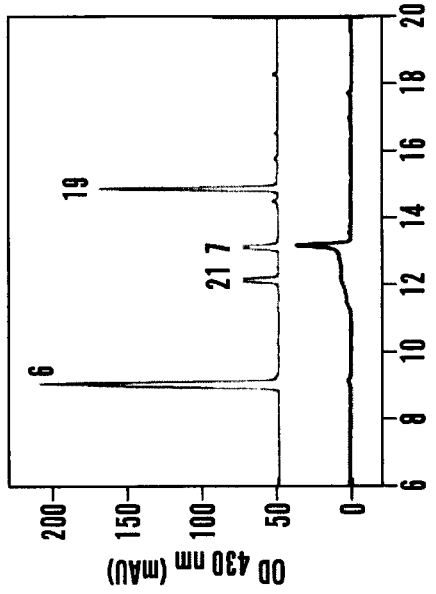
FIGS. 20A-20C depict HPLC-MS profiles of *P. gallaeciensis* BS107 cultures grown in the presence of various phenylpropanoids.
Figure 20A:
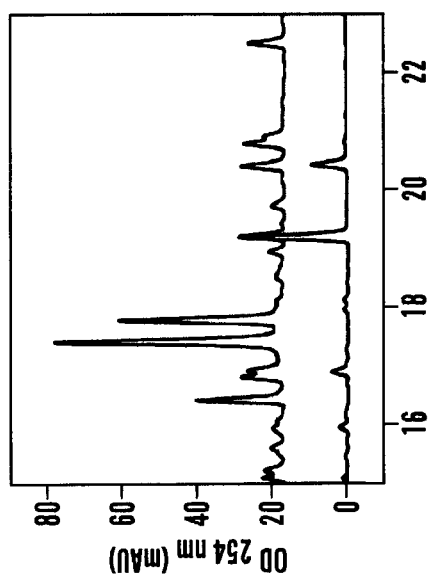
Figure 20C:
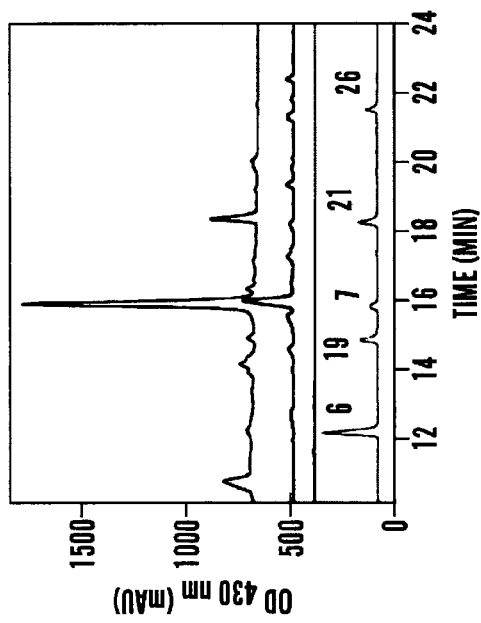

In addition to indicating that algal cell wall components may act as elicitors of bacterial metabolite production, the data presented above herein suggested that *P. gallaeciensis* BS107 is an opportunistic symbiont that could interact with a wide range of hosts. Bioinformatic analyses showed that *E. huxleyi* appears to only contain a pathway for the biosynthesis of H-lignin, the polymer resulting from linkage of pCA units. However, as the nature of lignin components varies with algal hosts,[15b] *P. gallaeciensis* BS107 could also encounter and respond to lignin monomers other than pCA. To test this hypothesis, *P. gallaeciensis* BS107 was incubated with various concentrations of pCA, sinapic acid (15) and ferulic acid (16), known components of cell wall lignin, as well as with cinnamic acid (17) and caffeic acid (18), intermediates in the biosynthesis of 14-16 (FIG. 15),[17] and the level of secondary metabolite production was assessed by HPLC-MS methods. Using 14, 15 and 16 as elicitors led to the production of a variety of new metabolites, 17 generated less dramatic results, and 18 produced no observable changes (FIGS. 20A-20C). These results indicate that other lignin monomers also activate metabolite production pathways in *P. gallaeciensis* BS107.

Figure 16:
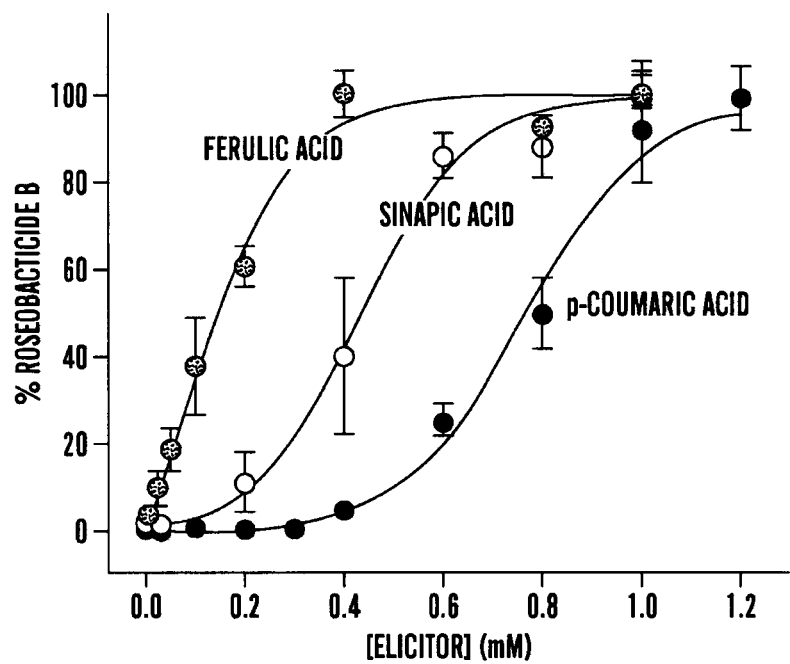
FIG. 16 depicts a graph of the dose-response analysis for three elicitors of roseobacticide production in *P. gallaciensis* BS107. The amount of (7) produced is plotted as a function of the concentrations of (14), (15), or (16), and the data fit to equation 1, yielding an $EC_{50}$ of 0.16±0.02 mM (16) and 0.43±0.03 (15). The data for (14) are from elsewhere herein, where a value of 0.79±0.03 was determined. For each elicitor, the maximal amount of (7) was normalized to 100%. Each point is the average of two independent measurements; error bars represent standard deviation about the mean.

To find optimal conditions for roseobacticide production, a dose response analysis was carried out with each of the main elicitors. *P. gallaeciensis* BS107 was incubated with varying concentrations of the elicitor, and roseobacticide B production was quantified using HPLC-ESI-MS. The analysis previously indicated a half-maximal effective concentration ($EC_{50}$) of 0.79±0.03 mM with pCA.2 With 15 and 16, $EC_{50}$ values of 0.43±0.03 and 0.16±0.02 mM, respectively, were obtained, indicating that these are more potent elicitors of roseobacticide B production in *P. gallaeciensis* BS107 (FIG. 16). Each elicitor also shows quantitative changes in the levels of roseobacticide B produced, which may have implications for the interaction of *P. gallaeciensis* BS107 with its algal hosts (see below).

Elucidation of New Roseobacticide Structures.

The compounds induced by pCA, sinapic acid and ferulic acid were purified from large-scale production cultures of *P. gallaeciensis* BS107 in the presence of each elicitor using standard solidphase extraction and HPLC methods. The structures were subsequently solved by 1D and 2D NMR spectroscopy, high resolution (HR) HPLC-ESI-MS and HR tandem ESI-MS. All structures reported below have an H/C ratio<1, and NMR analysis alone was usually not sufficient for structural elucidation necessitating tandem HR-MS and chemical degradation analyses. Using these techniques, the structures of nine new roseobacticides, which fall into four classes were elucidated (FIG. 17): (1) A phenol family with compounds 6, 20, and 24, which contain a thiomethyl, a methyl persulfide, or a p-hydroxybenzenethiol moiety at C7 and a phenol group at C3; (2) A phenyl family with compounds 7, 21, 23 and 25 containing a thiomethyl, a methyl persulfide, a sulfonate, or a p-hydroxybenzenethiol at C7 and a phenyl group at C3; (3) An indole family with roseobacticides C (19) and F (22), which contain a thiomethyl or a methyl persulfide at C7, and an indole at C3; and (4) A dimer family with roseobacticides J (26) and K (27), which consist of two roseobacticides joined through a disulfide linkage.

Figure 21:
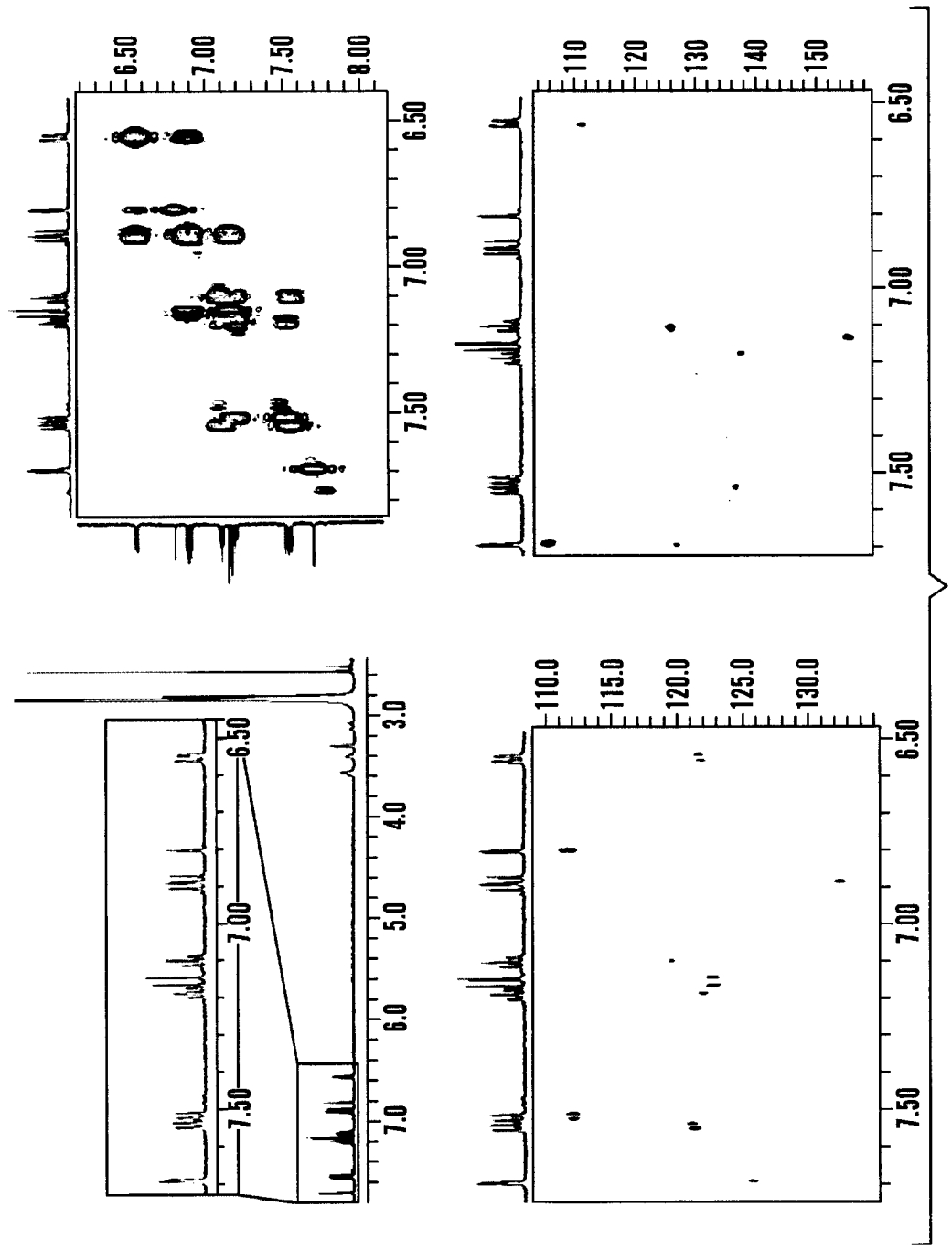
FIG. 21 depicts the NMR spectra of roseobacticide C in acetone-d6: $^1$H spectrum (top left), gCOSY (top right), gHSQC (middle left), HMBC (middle right), NOESY (bottom left), and a magnified view of the NOESY spectrum (bottom right).
Figure 21:
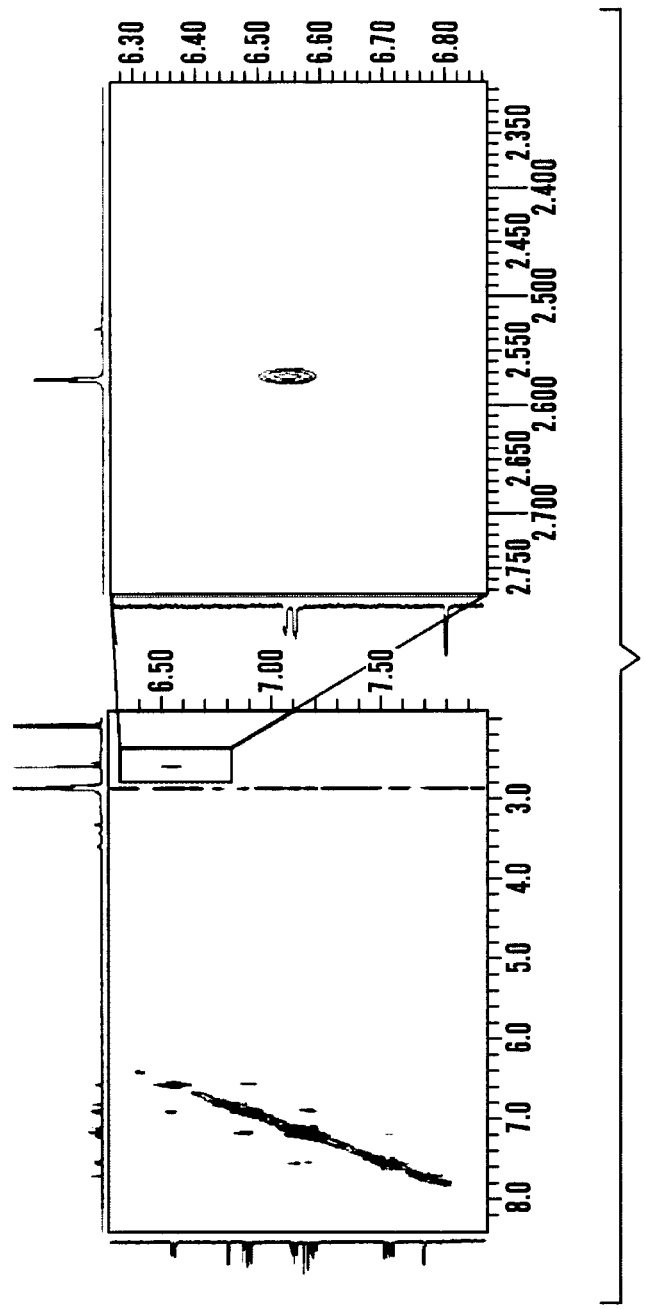
Figure 22:
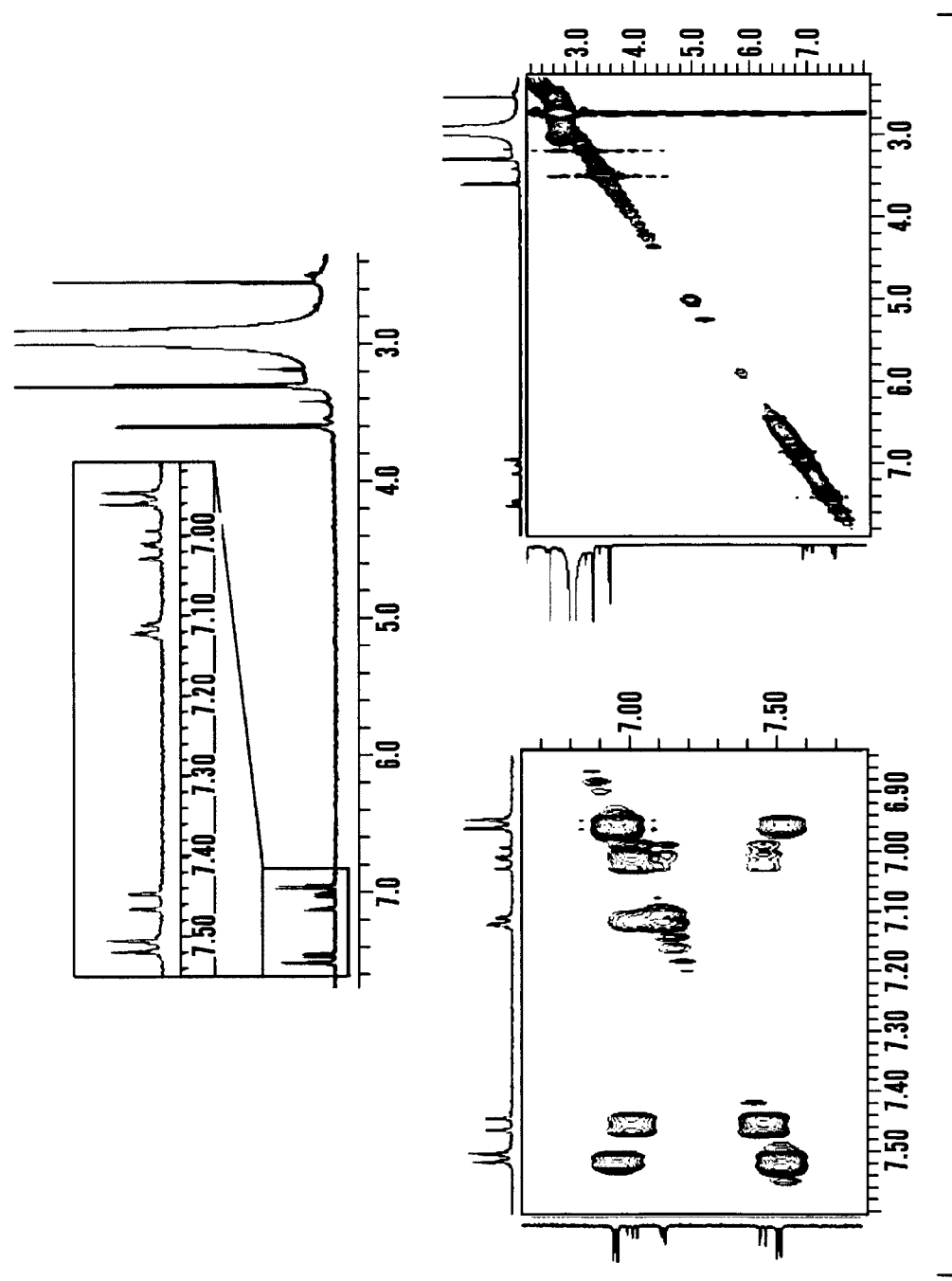
FIG. 22 depicts the NMR spectra of roseobacticide D in acetone-d6: $^1$H spectrum (top), gCOSY (middle left), NOESY (middle right), gHMBC (bottom left), gHSQC (bottom right), and a magnified view of the gHSQC spectrum (bottom right, inset).
Figure 22:
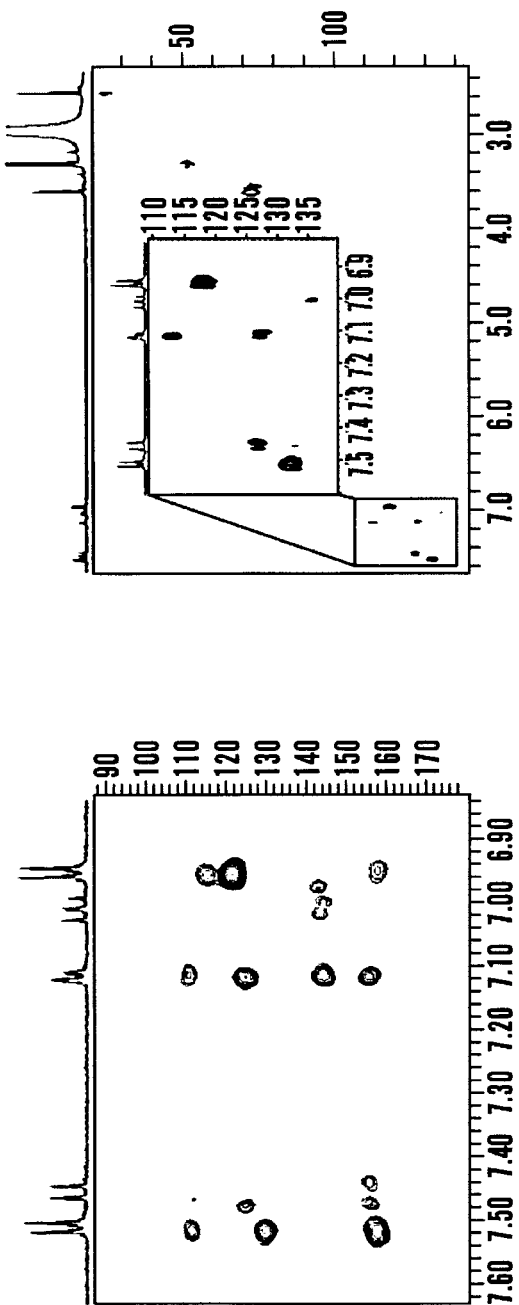
Figure 23:
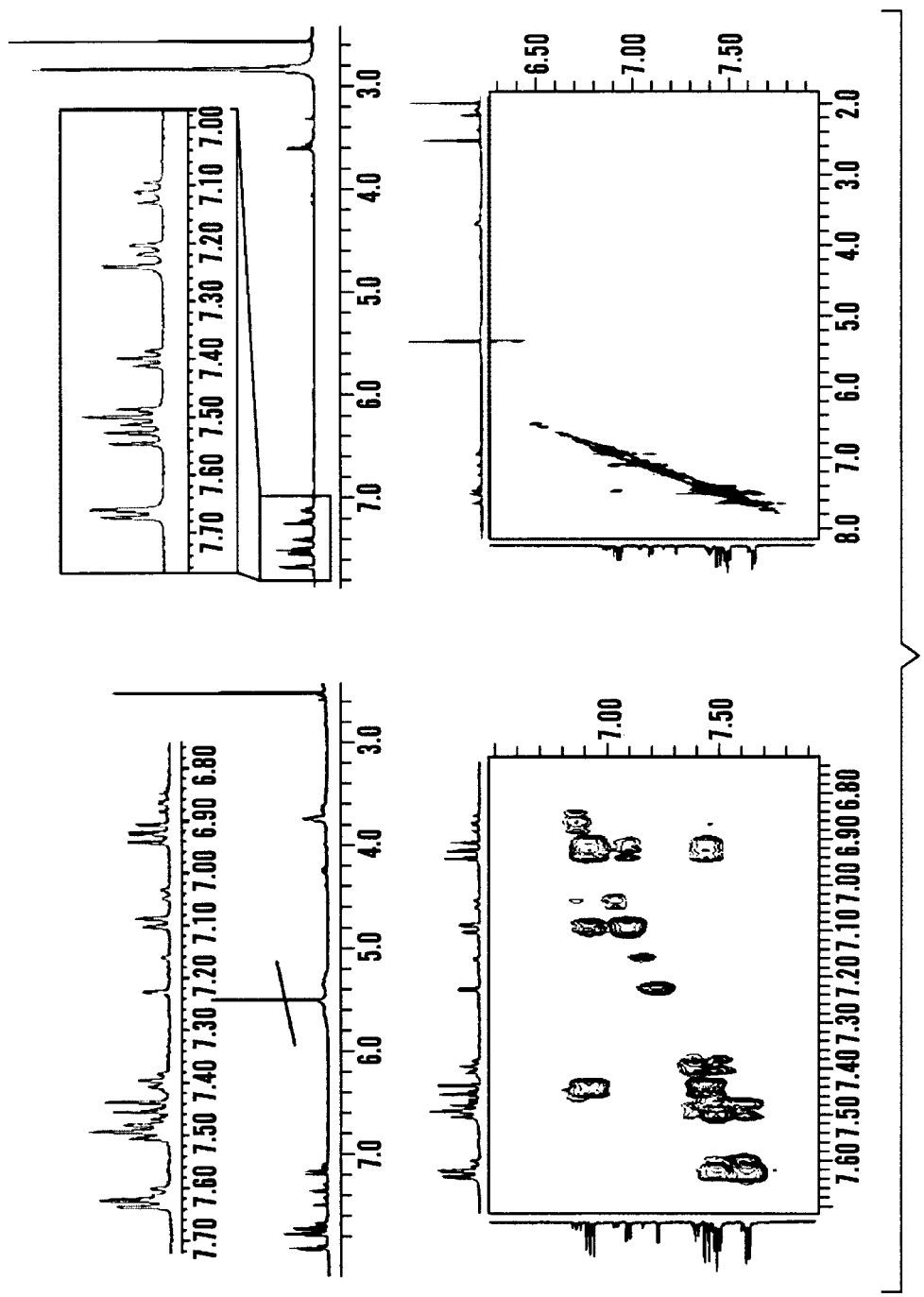
FIG. 23 depicts the NMR spectra of roseobacticide E in dichloromethane-d2: $^1$H spectrum (top left), 1H spectrum in acetone-d6 (top right), gCOSY (middle left), NOESY (middle right), gHSQC (bottom left), and a magnified view of the upfield region of the gHSQC spectrum (bottom right).
Figure 23:
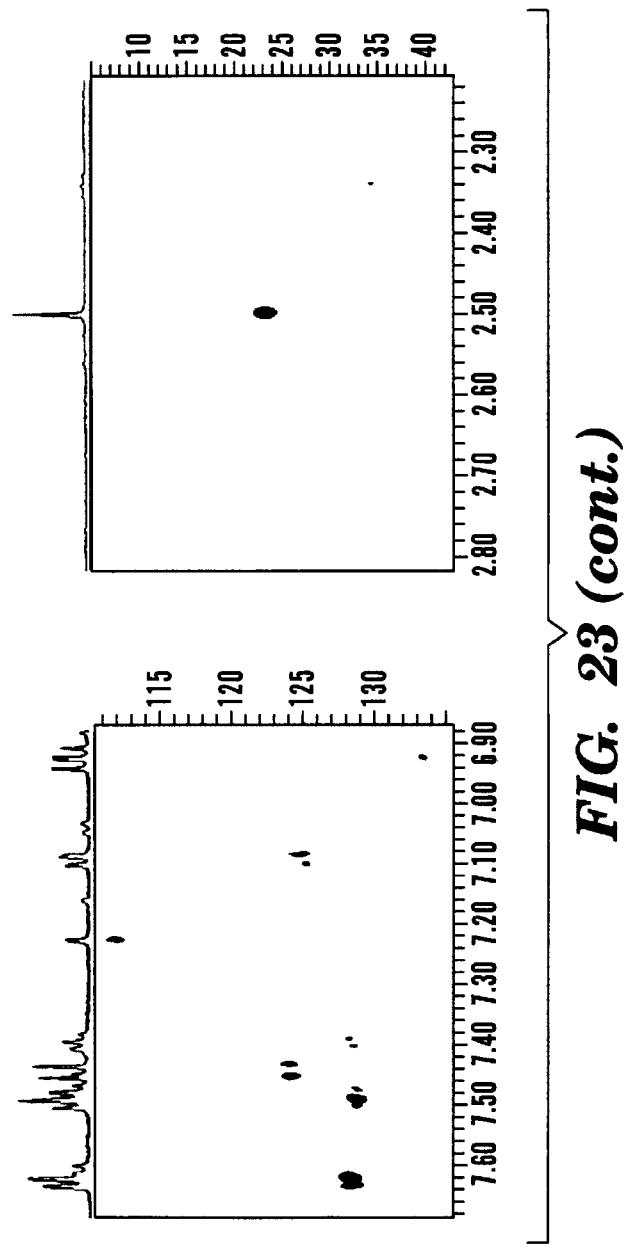
Figure 24:
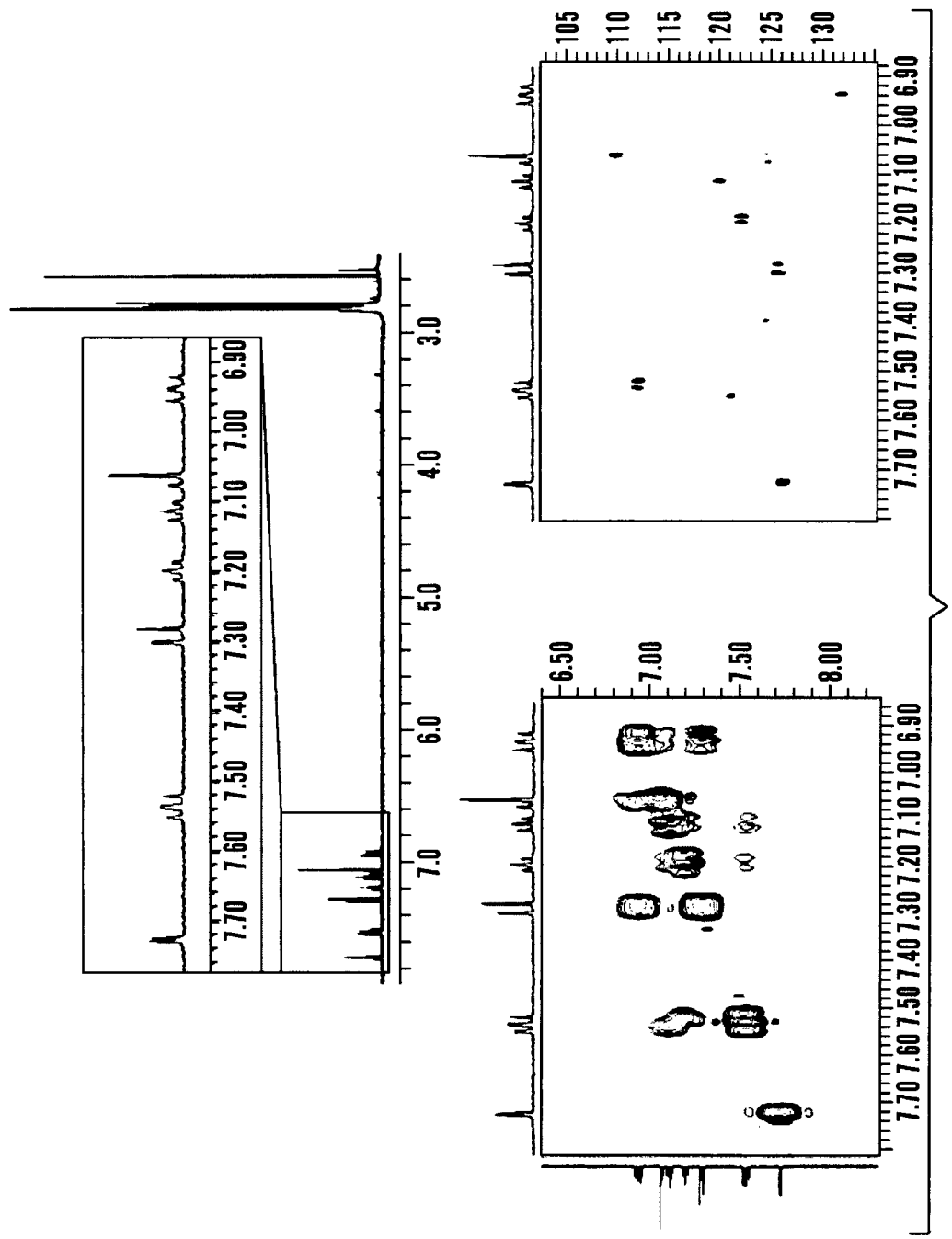
FIG. 24 depicts the NMR spectra of roseobacticide F in acetone-d6: $^1$H spectrum (top), gCOSY (middle left), gHSQC (middle right), NOESY (bottom left), and gHMBC (bottom right).
Figure 24:
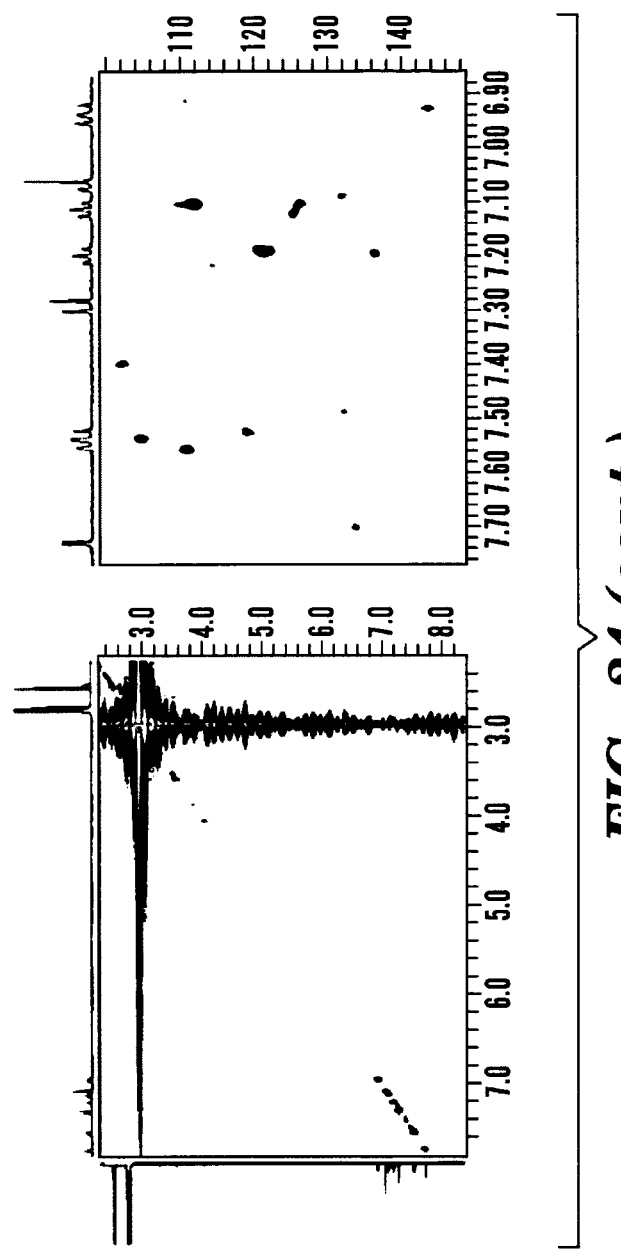
Figure 25A:
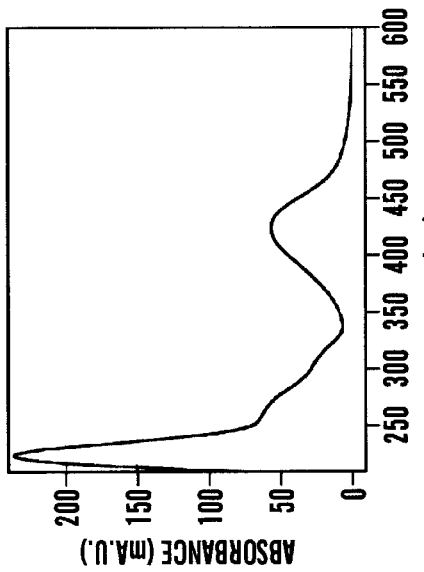
FIGS. 25A-25D depict analysis of the reactions of roseobacticides E (21) and J (26) with the reducing agent dithiothreitol (DTT).
Figure 25B:
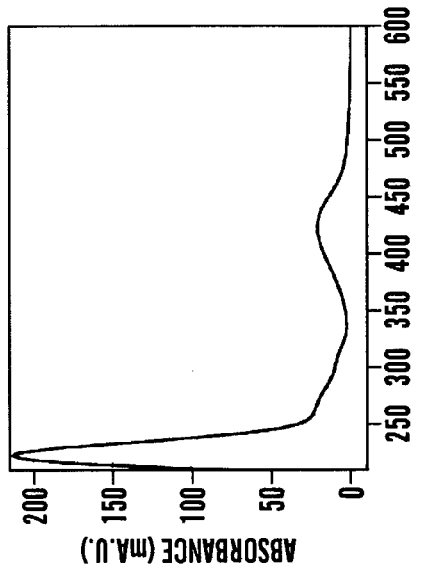
Figure 25C:
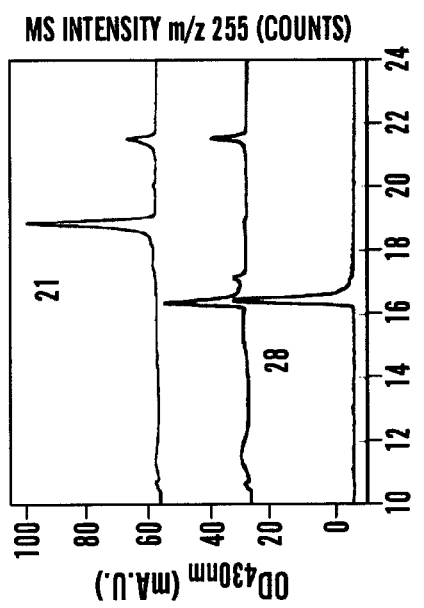
Figure 25D:
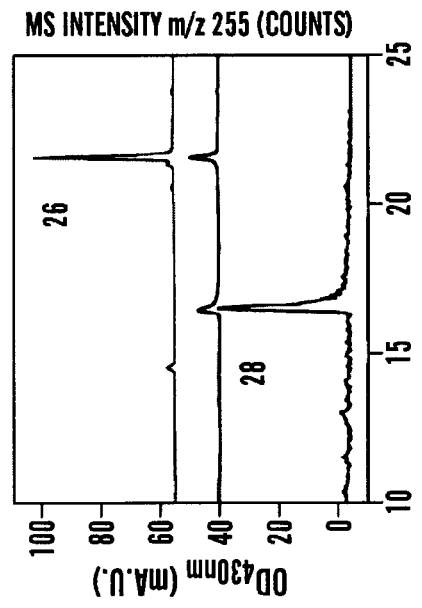
Figure 26:
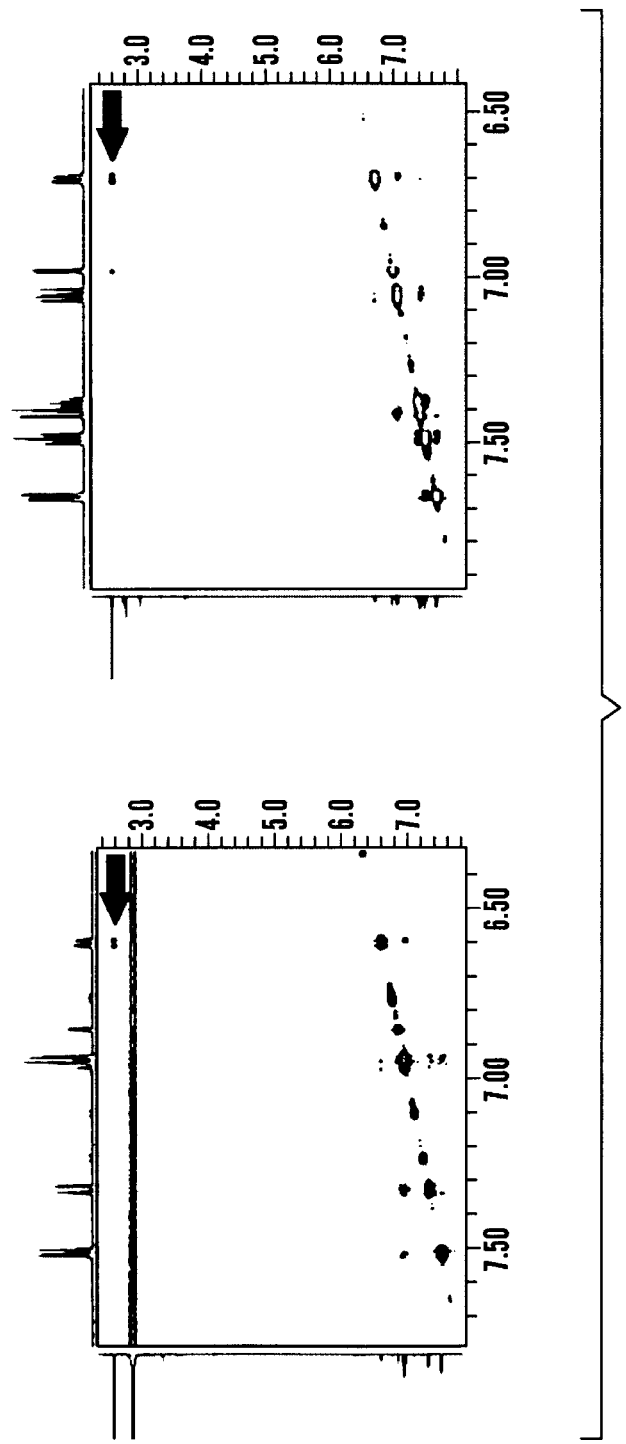
FIG. 26 depicts NOESY spectra of roseobacticides A, B, C, D, E and F. The letter on each spectra indicates the roseobacticide being analyzed. A correlation is observed between the methyl protons and the proton at C6 in roseobacticides A, B, and C, pointed out by the arrows, but not in roseobacticides D, E and F consistent with the increased distance between these protons.
Figure 26:
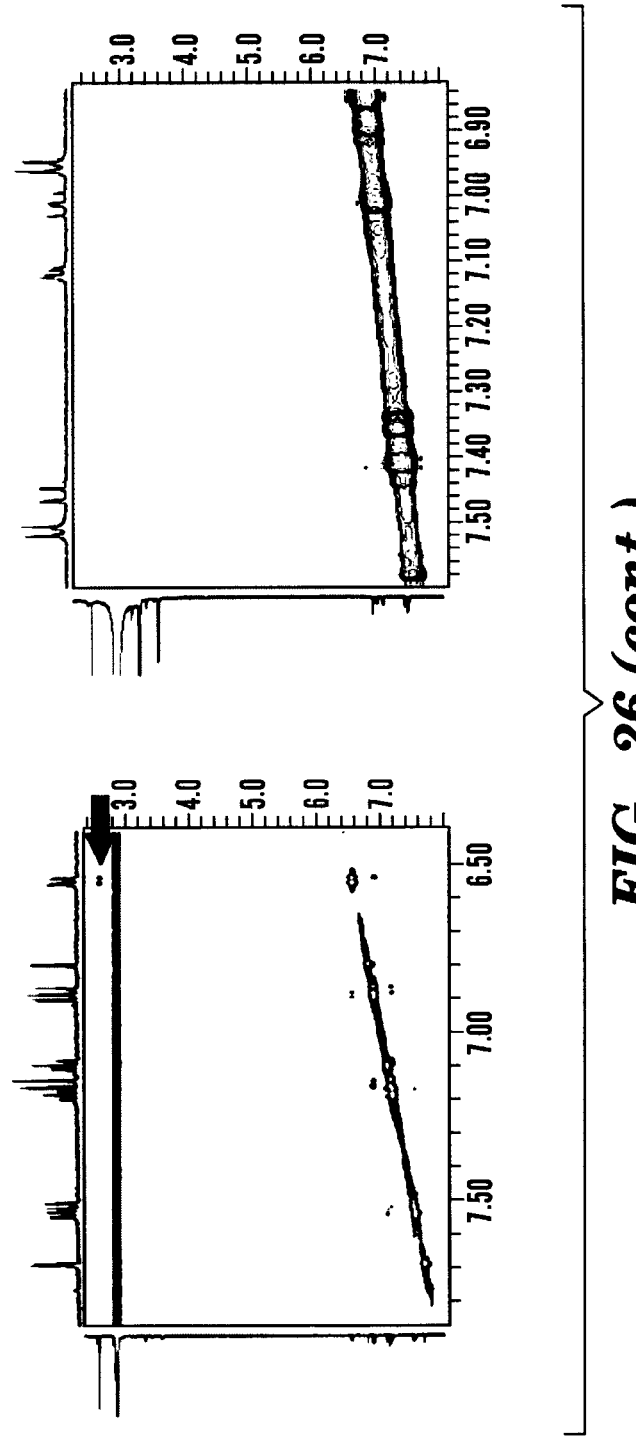
Figure 26:
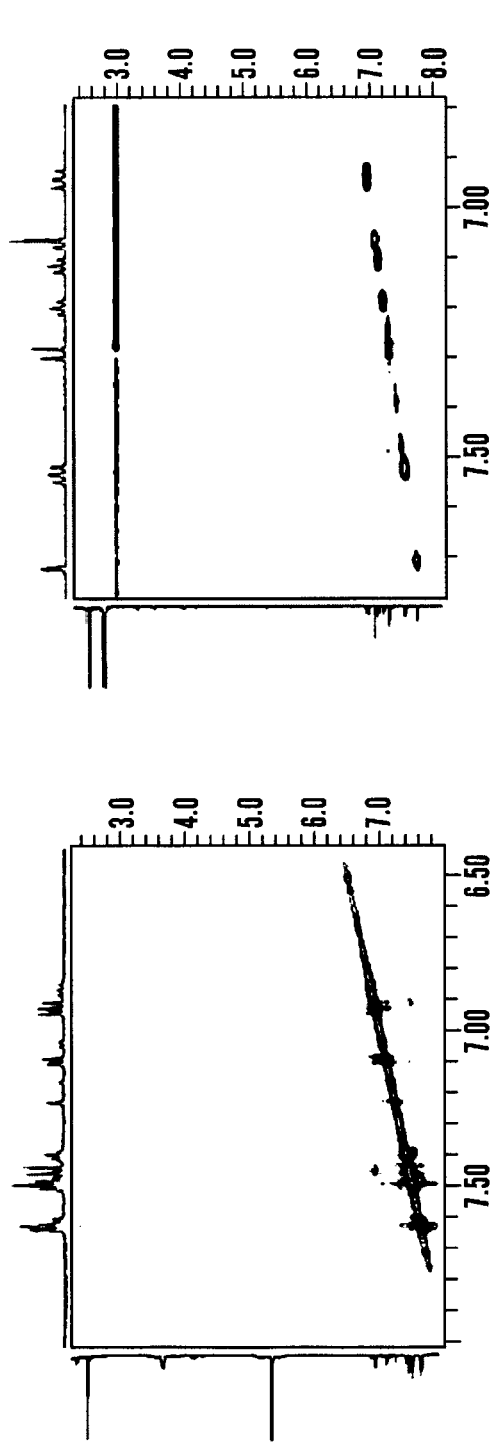
Figure 27:
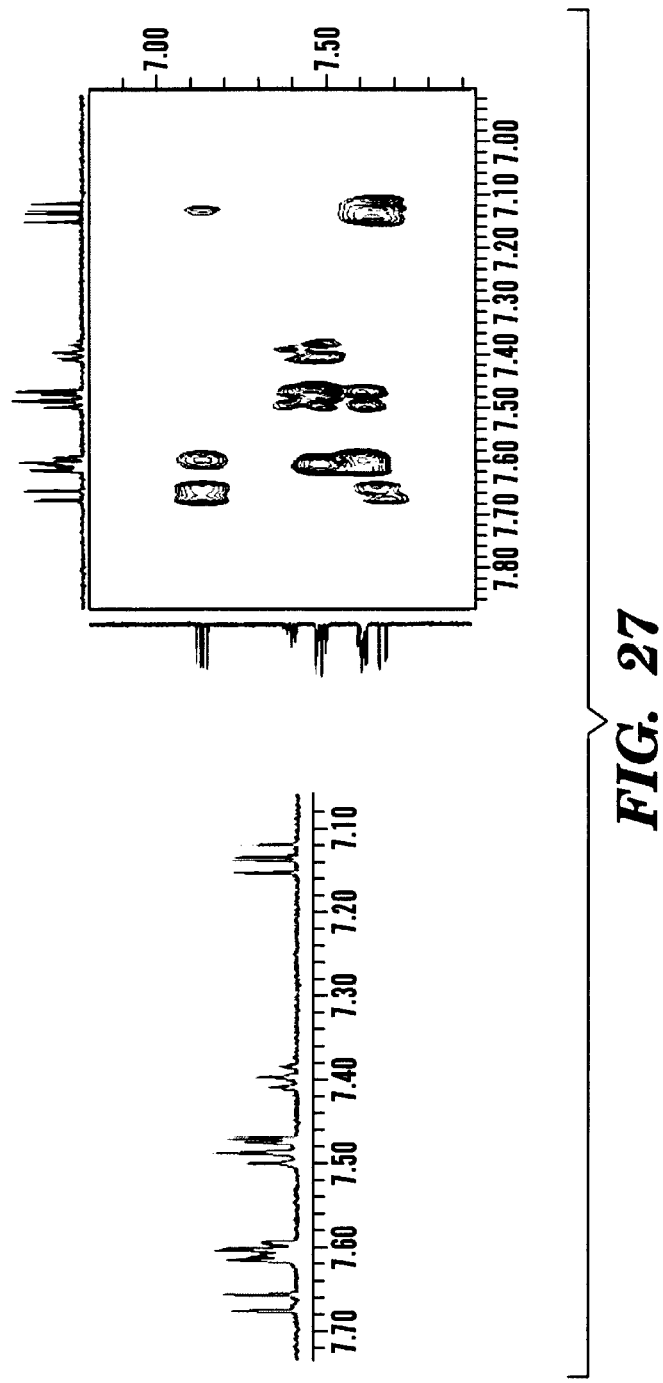
FIG. 27 depicts NMR spectra of roseobacticide G in acetone-d6: $^1$H spectrum (top left), gCOSY (top right), gHSQC (middle left), NOESY (middle right) and gHMBC (bottom).
Figure 27:
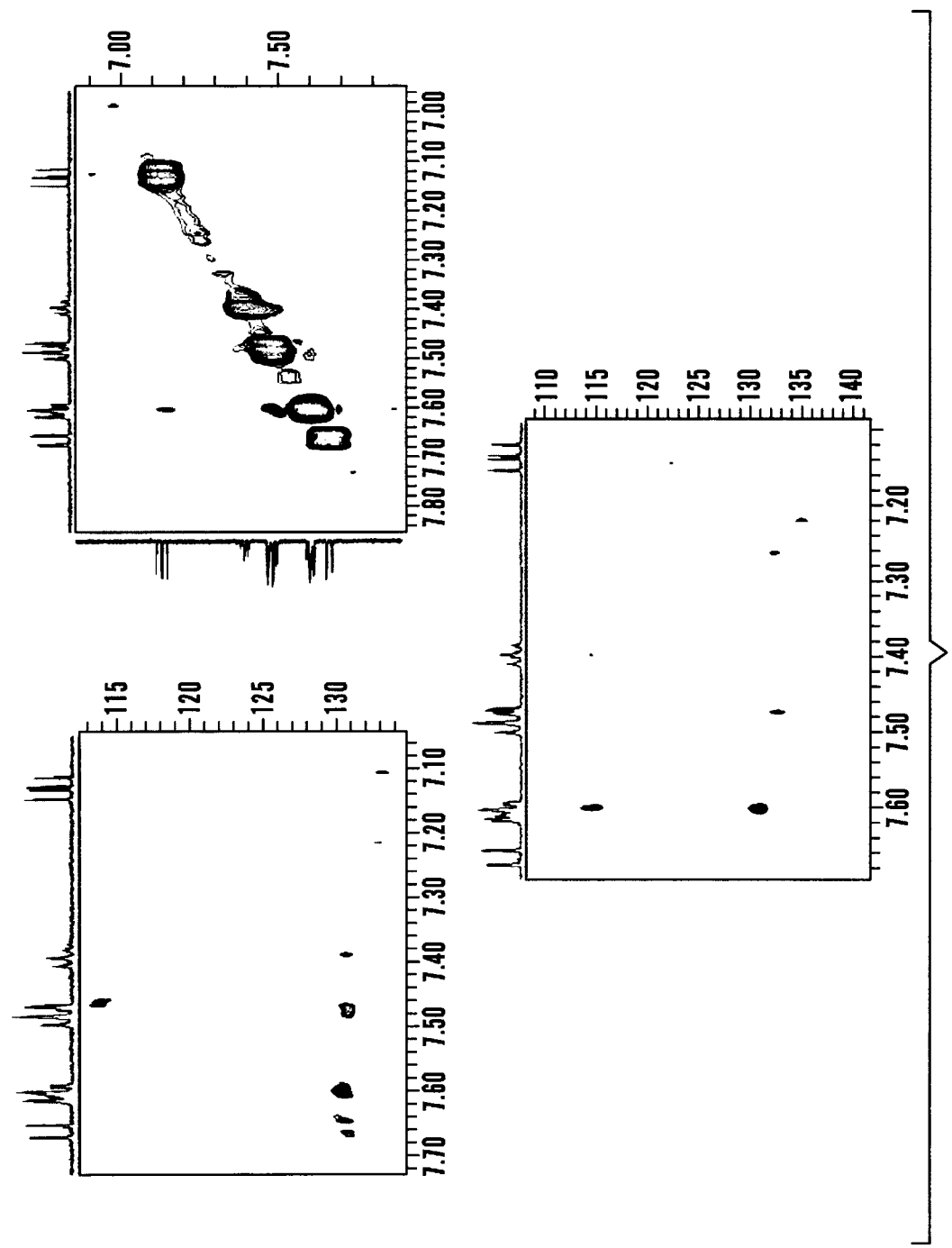
Figure 28:
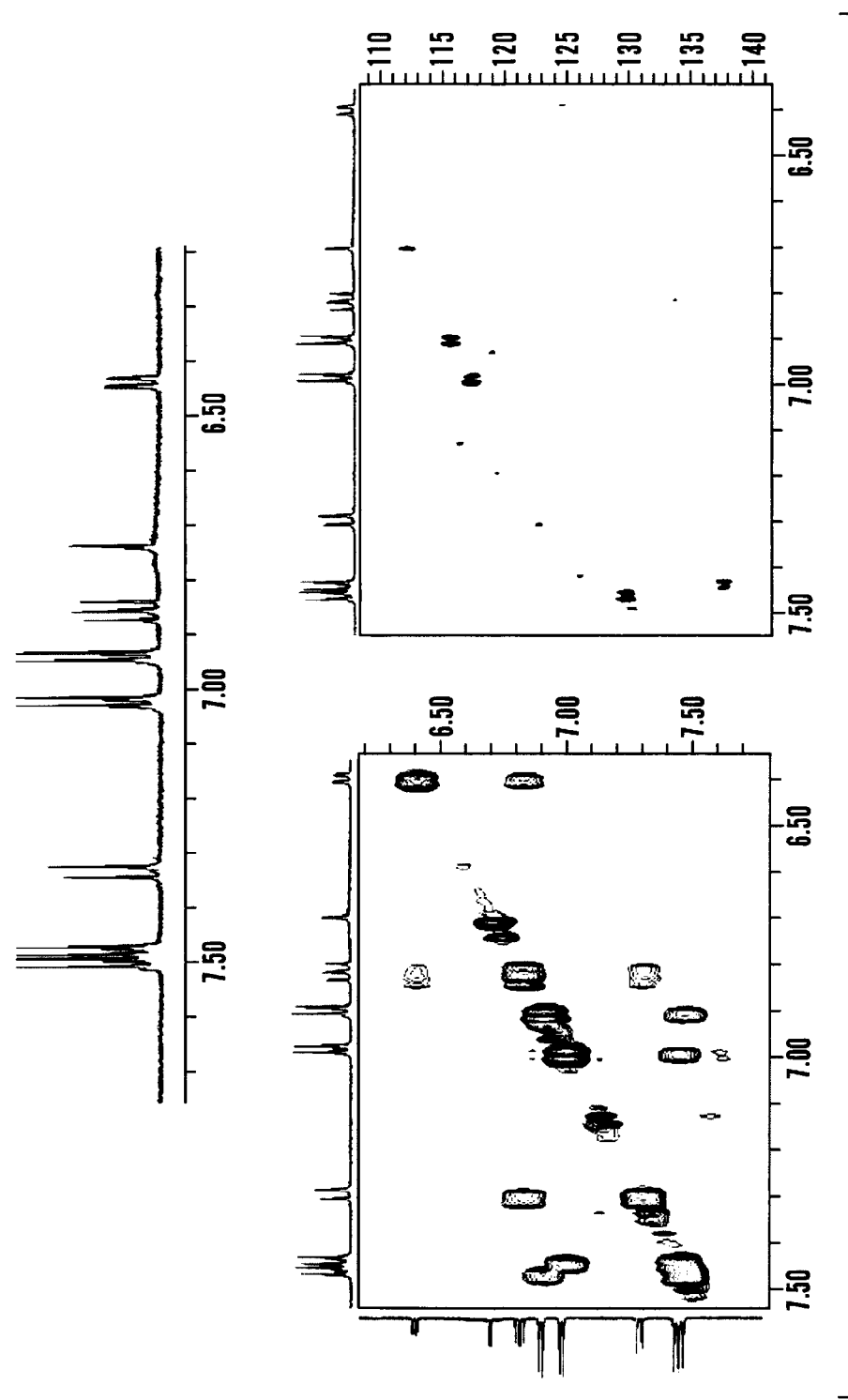
FIG. 28 depicts NMR spectra of roseobacticide H in acetone-d6: $^1$H spectrum (top), gCOSY (middle left), gHSQC (middle right), NOESY (bottom left), and gHMBC (bottom right).
Figure 28:
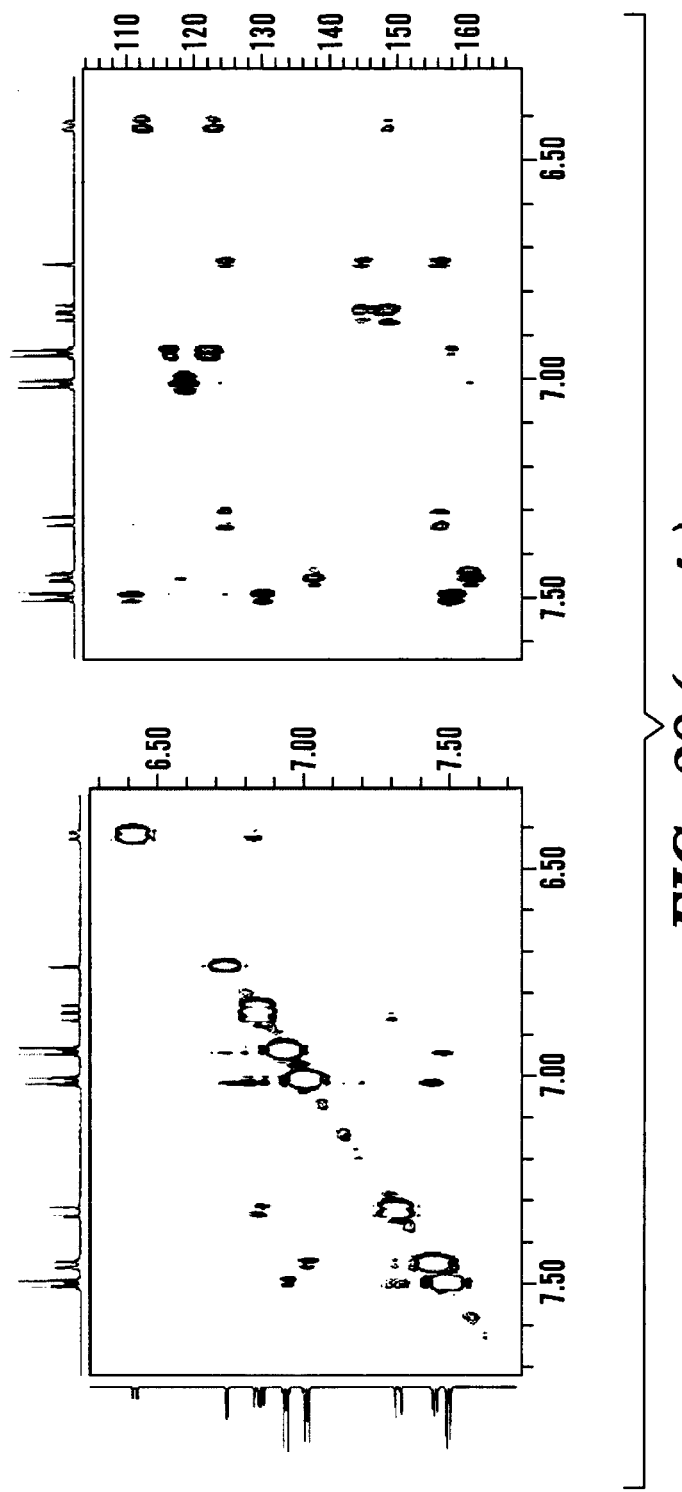
Figure 29:
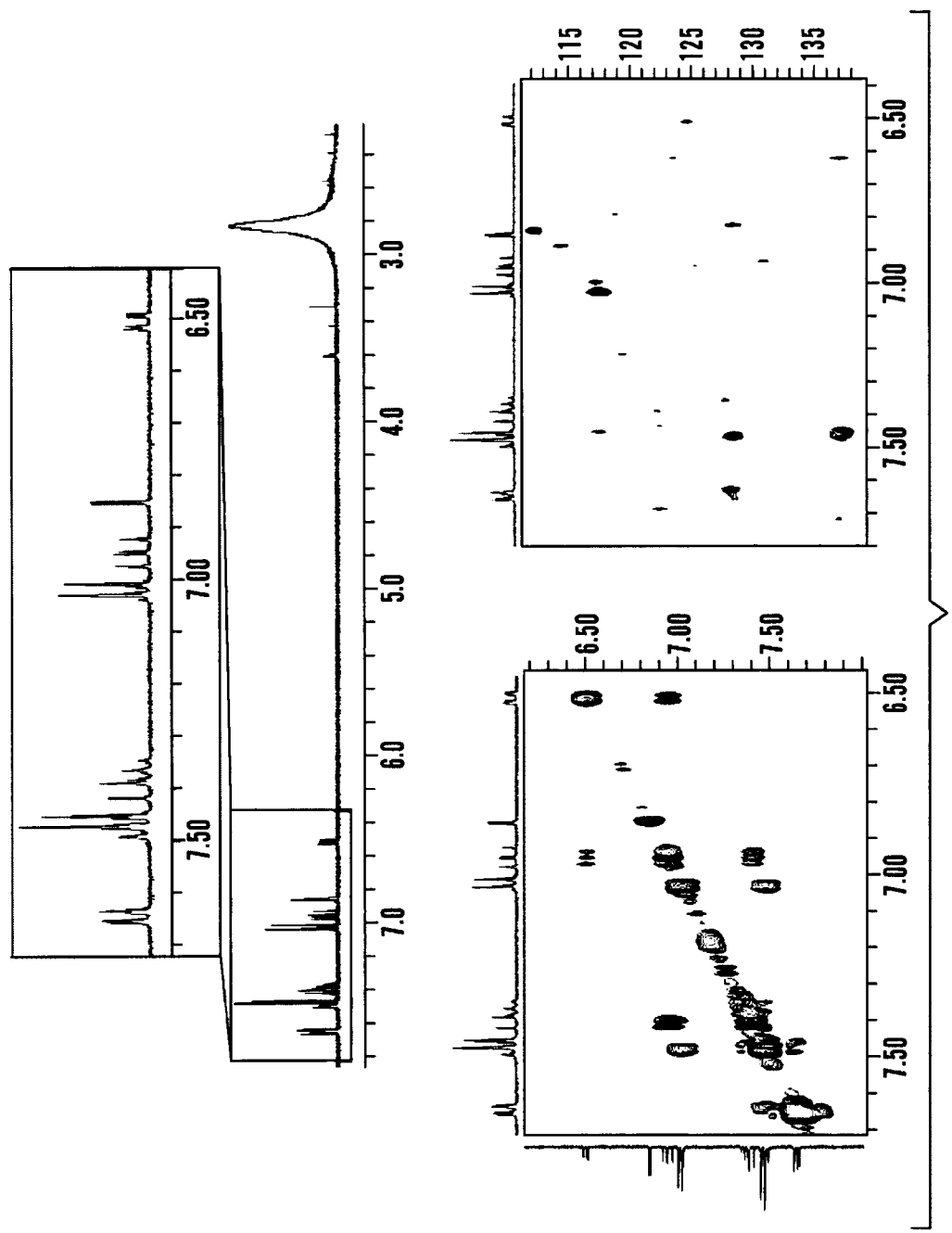
FIG. 29 depicts NMR spectra of roseobacticide I in acetone-d6: $^1$H spectrum (top), gCOSY (middle left), gHSQC (middle right), and gHMBC (bottom right).
Figure 29:
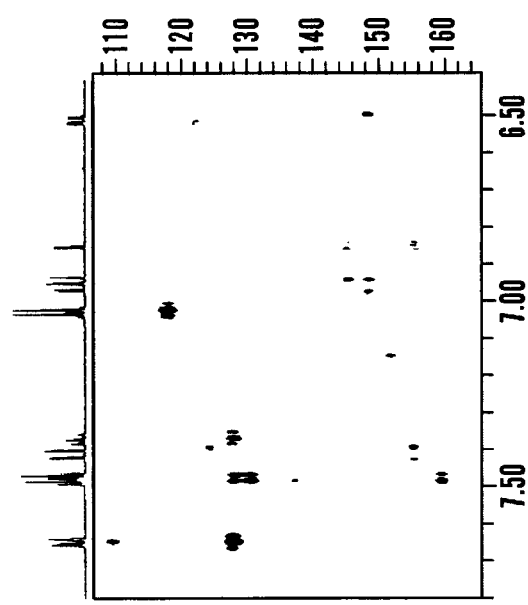

The structure of the first indole analog, roseobacticide C (FIG. 17), was solved readily from 1D and 2D NMR spectra and HR-ESI-MS (Tables 7-8). The $^1$H NMR spectrum revealed a pattern diagnostic of the 1-oxaazulan-2-one core with a different substituent at C3 (FIG. 21). $^1$H NMR, COSY, HSQC and HMBC spectra (FIG. 21; Table 9) indicated an indole group in agreement with a molecular formula of $C_{18}H_{13}NO_2S$ ([M+H]+calc. 308.0745, expt. 308.0738). Tandem HR-MS analysis was consistent with this assignment (Table 8). As with 6 and 7, the NOESY spectrum of 19 revealed a cross peak between the methyl protons and the proton at C6 (FIG. 21). The nature of the substituent at C3 in 6, 7 and 19, points to aromatic amino acids as precursors in roseobacticide biosynthesis. In addition, the presence of indole at the C3 position implicates indoleacetic acid as an intermediate in the biosynthesis of 19.[2] Because indoleacetic acid is a prominent plant and algal growth promoter,[18] the presence of 19 further supports our model in which the mutualist-to-pathogen switch results in a conversion of growth-promoting metabolites into phytotoxins.

Figure 17:
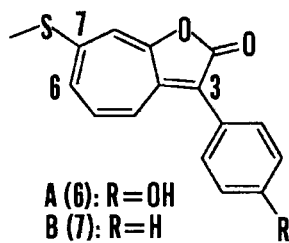
FIG. 17 depicts the structures of roseobacticides A-K.
Figure 17:
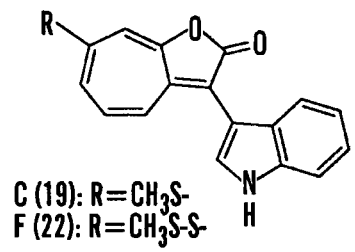
Figure 17:
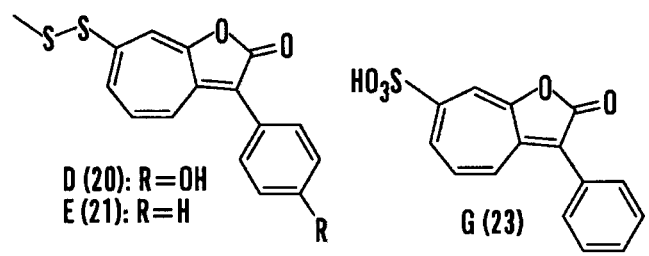
Figure 17:
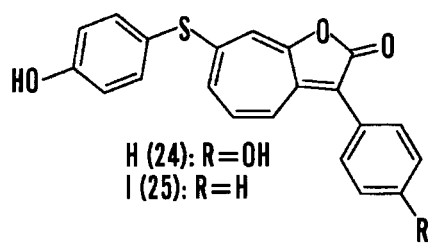
Figure 17:
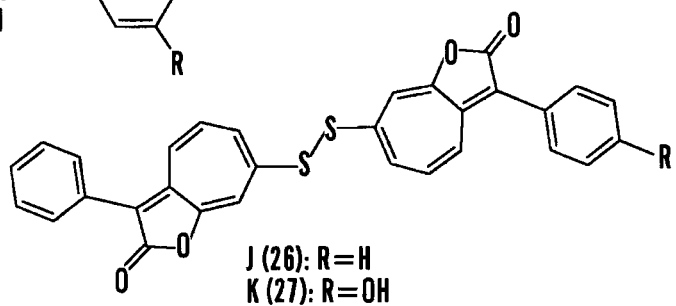
Figure 18:
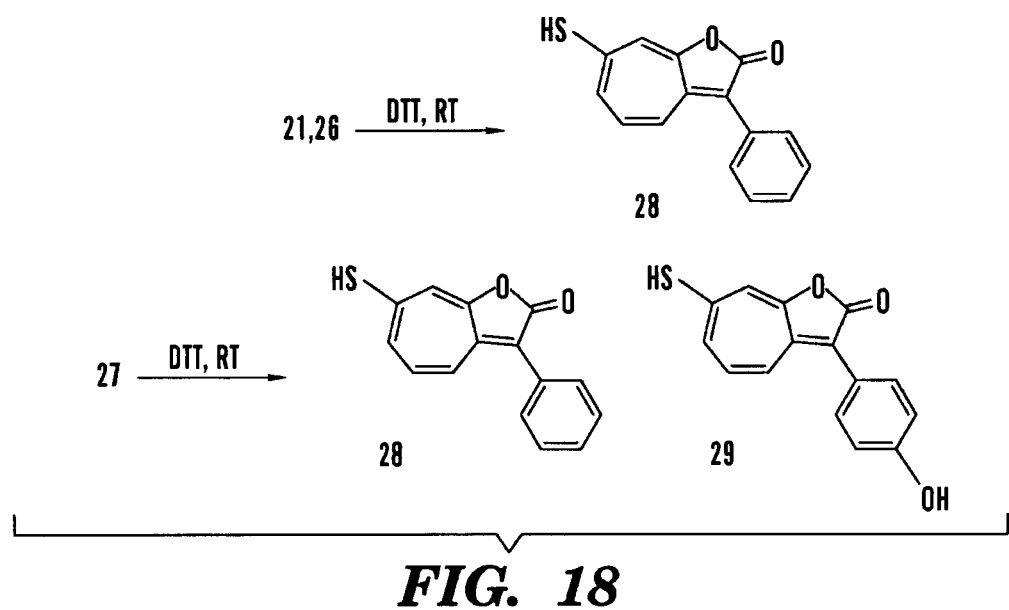
FIG. 18 depicts the products of the reactions of (21), (26), and (27) with the disulfide reducing agent dithiothreitol (DTT).
Figure 19:
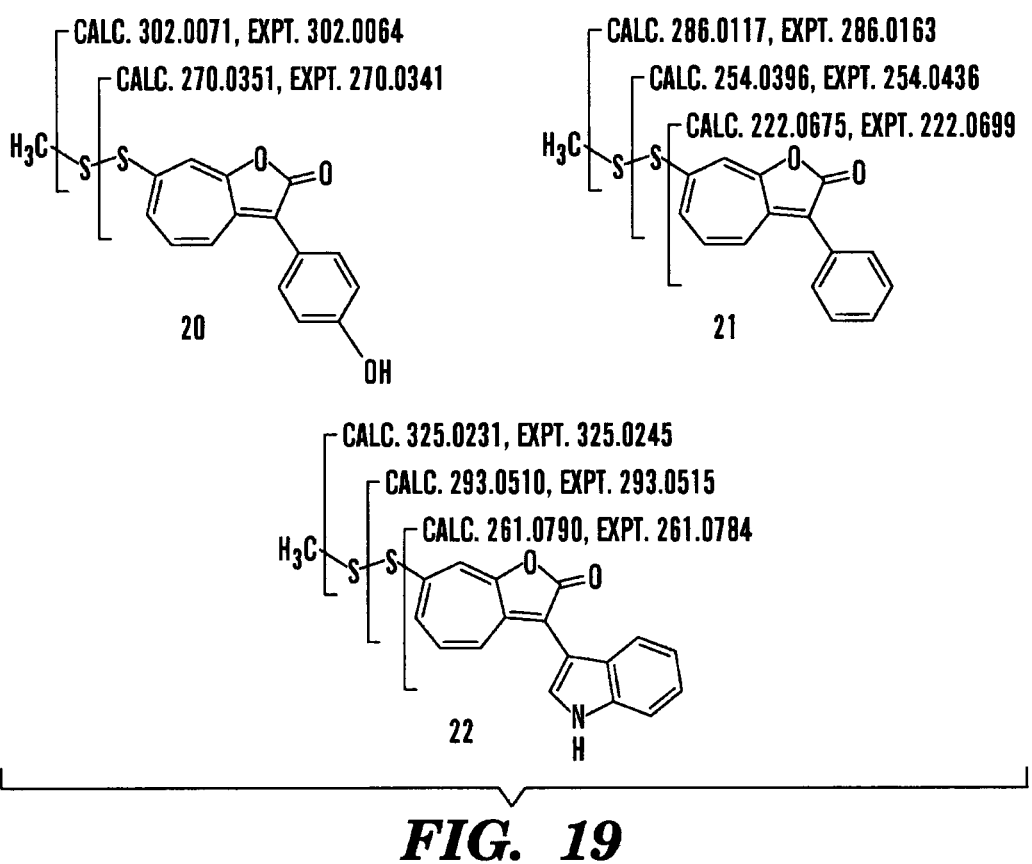
FIG. 19 depicts the major $[M+H]^+$ MS-MS fragments obtained with (20-22).

HR-ESI-MS analysis of roseobacticides D, E and F indicated that they contain an additional sulfur atom relative to roseobacticides A, B and C, respectively (Table 7). On the basis of the $^{13}C$ chemical shifts of the methyl groups in 20-22, (22-23 ppm, FIGS. 22-24; Tables 10-12) compared to that of the methyl groups in 6, 7 and 19 (~15 ppm, Table 9), it was suspected that the former contained a methyl persulfide rather than a thiomethyl group at C7. Incubation of 21 with the reducing agent dithiothreitol (DTT) followed by low resolution HPLC-MS analysis gave a fragment consistent with loss of methanethiol ((28), FIGS. 25A-25D, FIG. 18, [M+H]+ calc. 255.1, expt. 255.1) in agreement with a methyl persulfide functionality. In addition, tandem HR-MS analysis with 21 (FIG. 19) gave fragments resulting from the loss of a methyl group ([M+H]+calc. 286.0117, expt. 286.0163), loss of a thiomethyl group (M+H]+calc. 254.0396, expt. 254.0436) and loss of a methyl persulfide ([M+H]+calc. 222.0675, expt. 222.0699) establishing the structure of 21 as shown in FIG. 17. The corresponding fragments were also obtained with 20 and 22 (FIG. 19, Table 8). The NOESY spectra of 20-22 did not reveal a cross peak between the methyl protons and the C6-proton (FIG. 26), in agreement with the increased distance in a methyl persulfide substituent, and with the assigned structures. The $^1H$ NMR and HSQC spectra of 23 revealed a pattern similar to that of 7, but with major differences in $^1H$ and $^{13}C$ chemical shifts (FIG. 27; Table 13). The nature of these shifts and the broad peak of this compound during chromatography, even in the presence of 0.1% formic acid, suggested an acidic functionality. HR-MS yielded a formula of $C_{15}H_{10}O_5S$ in line with the presence of a sulfonic acid at C7. Tandem HR-MS gave fragments consistent with the loss of $SO_2$, which is diagnostic for aromatic sulfonates,[19] as well as with the loss of $SO_3H$ and CO (Table 8). The loss of CO occurred in tandem MS spectra of nearly all roseobacticides and presumably originates from collision-induced dissociation of CO from the lactone group. These fragments and the NMR spectra are consistent with the assignment of 23 as a C7-sulfonate-bearing variant of 7. The incorporation of a sulfonate in place of a thiomethyl group is further demonstration of the ability of roseobacter to modify the oxidation state of sulfur-containing compounds.[4,5c,20]

$^1H$ NMR, COSY and HSQC spectra of 24 and 25 were in line with the presence of the 1-oxaazulan-2-one core with the thiomethyl group at C7 replaced with a different substituent. The NMR data (FIGS. 28-29; Tables 14-15) pointed to a phenol-containing moiety at C7. HR-ESI-MS gave molecular formulas of $C_{21}H_{14}O_4S$ and $C_{21}H_{14}O_3S$ for 24 and 25, respectively, and together with the NMR data were indicative of a bridging sulfur atom and a hydroxyl group in the para position, rather than an ether linkage and a free thiol, raising the possibility that the substituent was a p-hydroxybenzenethiol in both cases (FIG. 17). This was confirmed by tandem HR-MS, which for both compounds gave the p-hydroxybenzenethiol fragment (Table 8, [M–H]–calc. 123.9983, expt. 123.9989 for 24 and obs. 123.9987 for 25), as well as the fragment resulting from loss of the substituent at C7 (24: [M+H]+calc. 238.0630, expt. 238.0621; 25: [M+H]+ calc. 222.0682, expt. 222.0673).

Figure 30:
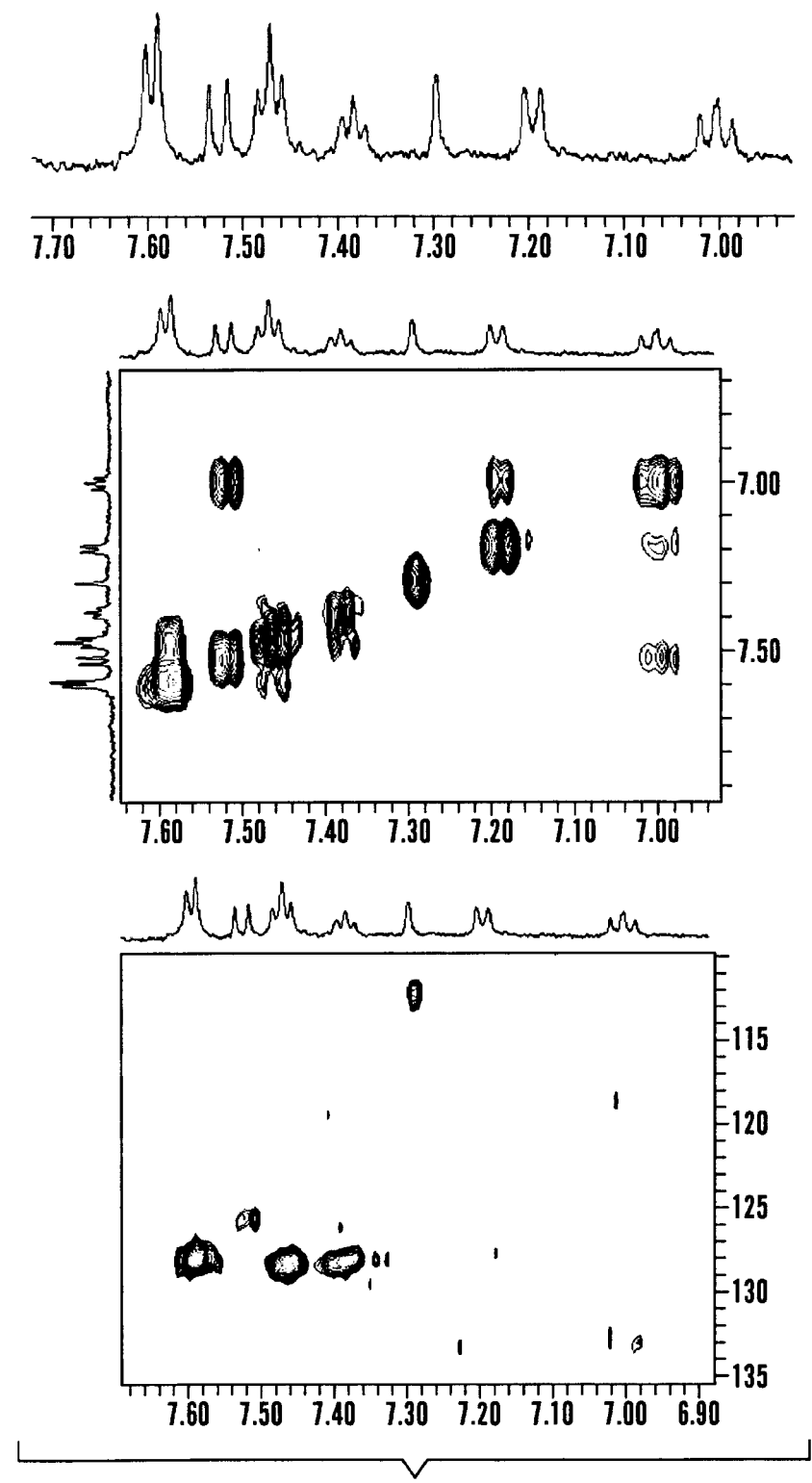
FIG. 30 depicts NMR spectra of roseobacticide J in acetone-d6: $^1$H spectrum (top), gCOSY (middle), and gHSQC (bottom).
Figure 31:
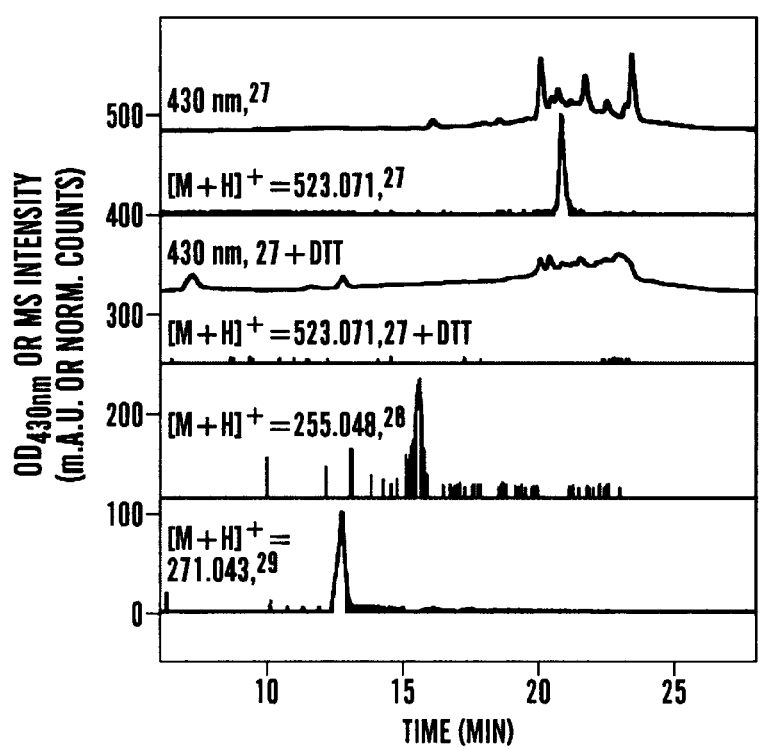
FIG. 31 depicts HR-HPLC-MS analysis of the reaction of roseobacticide K (27) with DTT. Profile of a partially purified fraction containing roseobacticide K (top trace) and extracted MS trace for the roseobacticide K ion (second trace from the top, [M+H]+=523.071). After treatment of the fraction containing roseobacticide K with DTT (fourth trace from bottom), the MS ion of roseobacticide K cannot be detected (third trace from bottom). Instead the components of roseobacticide K can be identified as seen in the extracted MS trace of 28 (second trace from bottom, [M+H]+=255.048) and of 29 (bottom trace, M+H]+=271.043).

26, by HR-MS analysis and $^1H$ NMR, HSQC, and NOESY spectra, appeared to be comprised of two roseobacticide B fragments joined end-to-end via a disulfide bond (FIG. 30; Table 16). Treatment of 26 with DTT gave rise to 28, which was also obtained after treatment of 21 with DTT (FIG. S6, [M+H]+calc. 255.1, expt. 255.1). HPLC-HR-MS monitoring of this reaction corroborated the assignment of the new peak as 28 ([M+H]+calc. 255.0480, expt. 255.0483). Tandem HR-MS analysis confirmed the structure of 26 revealing a major fragment arising from cleavage of the disulfide bond (Table 8, [M+H]+calc 254.0402, expt. 254.0398), in line with the molecular formula of $C_{30}H_{18}O4S2$ ([M+H]+calc. 507.0725, expt. 507.0736). During purification of 26, a faster-migrating fraction with a similar UV-visible spectrum was observed. The molecular formula of $C_{30}H_{18}O_5S_2$ is consistent with 27, as are the two main fragments observed by tandem HR-MS, which originate from cleavage of the disulfide bond (Table 8, [M+H]+calc. 270.0351, expt. 270.0383 and [M+H]+calc. 254.0402, expt. 254.0420). In addition, treatment of 27 with DTT led to its disappearance and formation of new peaks, one consistent with 28 (FIG. 31, [M+H]+calc. 255.0480, expt. 255.0490), and another consistent with 29 ([M+H]+calc. 271.0429, expt. 271.0439, see FIG. 18). The structure of 27 has been assigned based on its migratory properties, UV-visible spectrum, HR-MS and tandem HR-MS. This compound was produced in very small quantities insufficient for NMR analysis. Therefore, the structure shown for 27 remains tentative.

Host-Targeted Roseobacticide Production.

Having characterized the structures of the new roseobacticides, the elicitor-dependent differential production of each analog was analyzed. Table 6 summarizes the amount of each roseobacticide obtained as a function of elicitors 14-17. While there were batch-to-batch variations, sinapic acid was consistently the most effective elicitor with *P. gallaeciensis* BS107 both in the amount and diversity of roseobacticides stimulated followed by pCA, ferulic acid and cinnamic acid. As lignin monomers vary depending on the algal host,[15b] the quantitative and qualitative changes observed in Table 6 may indicate host-specific production of roseobacticides. These results also indicate that *P. gallaeciensis* BS107 produces a library of roseobacticides, but each in relatively small quantities, perhaps because of the potency of roseobacticide activity, which has been observed with 6 and 7, and the broad range of hosts with which *P. gallaeciensis* BS107 likely interacts.

Roseobacticide Production by *P. Gallaeciensis* 2.10.

Figure 32:
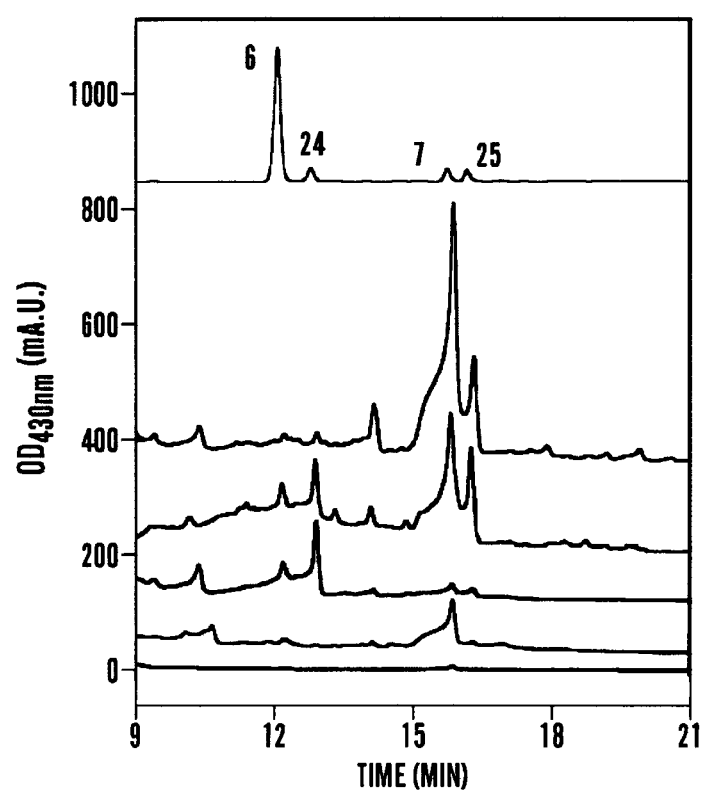
FIG. 32 depicts HR-HPLC-MS profiles of *P. gallaeciensis* 2.10 cultures grown in the presence of various phenylpropanoids. Extracts of cultures grown in the absence (bottom trace), or in the presence of 1 mM sinapic acid (second trace from the bottom), p-coumaric acid (third trace from the bottom), cinnamic acid (fourth trace from the bottom) or ferulic acid (second trace from the top) are shown. A profile of purified roseobacticides A (6), B (7), H (24), and I (25) is also shown (top trace). The presence of 6, 7, 24 and 25 in *P. gallaeciensis* 2.10 culture extracts was confirmed and quantified by HR-MS and HR-MS ion extraction, respectively. Comparison of the area of the extracted mass ion peak with a standard curve of known amounts of 6, 7, 24 and 25 yields the values shown in Table 6.

Because of the ecological contributions of bacterial-algal symbioses, it is important to identify new roseobacticide producers as a measure of the potential environmental significance of this compound class. To assess how widespread roseobacticide production is, three of the closest relatives to *P. gallaeciensis* BS107 were examined: *Phaeobacter gallaeciensis* 2.10.[12f] isolated from the green macroalga, *Ulva lactuca*; *Phaeobacter inhibens*,[3,21] isolated from the German Wadden Sea; and *Marinovumalgicola*,[22] isolated from the dinoflagellate *Prorocentrumlima*. Each strain was grown under identical conditions as *P. gallaeciensis* BS107 in the presence of 14-17. No roseobacticides were observed with *P. inhibens* or *M. algicola* under these conditions. In the case of *P. gallaeciensis* 2.10, various roseobacticides were produced as a function of the elicitor examined (FIG. 32); the data are summarized in Table 6. Compound 14 induced the production of 6, 7, 24 and 24, while 16 stimulated production of large quantities of 7 and 25. Sinapic acid resulted in production of only 7 at approximately similar levels as obtained with 17. In contrast to *P. gallaeciensis* BS107, 17 was a good elicitor in *P. gallaeciensis* 2.10. Overall, a different trend was observed with *P. gallaeciensis* 2.10 in that 16 was the strongest elicitor, followed by 17, 14 and 15. Production of roseobacticides by *P. gallaeciensis* 2.10 suggests they may be active against macroaglae, or that *P. gallaeciensis* 2.10 is, like its BS107 relative, also an opportunistic algal symbiont.

REFERENCES (1) (a) Piel, *J. Nat. Prod. Rep.* 2009, 26, 338. (b) Dudler, R.; Eberl, L. *Curr. Opin. Biotechnol.* 2006, 17, 268. (c) Schmidt, E. W. *Nat. Chem. Biol.* 2008, 4, 466, (2) Seyedsayamdost, M. R.; Case, R. J.; Kolter, R.; Clardy, J. Nat. Chem. 2011, 3, 331.

(3) Martens, T.; Heidorn, T.; Pukall, R.; Simon, M.; Tindall, B. J.; Brinkhoff, T. *Int. J. Syst. Evol. Microbiol.* 2006, 56, 1293.

(4) (a) Wagner-Döbler, I.; Biebl, H. *Annu. Rev. Microbiol.* 2006, 60, 255. (b) Buchan, A.; Gonzalez, J. M.; Moran, M. A. *Appl. Environ. Microbiol.* 2005, 71, 5665.

(5) (a) Brinkhoff, T.; Bach, G.; Heidorn, T.; Liang, L.; Schlingloff, A.; Simon, M. *Appl. Environ. Microbiol.* 2004, 70, 2560. (b) Geng, H.; Belas, R. *J. Bacteriol.* 2010, 192, 4377. (c) Thiel, V.; Brinkhoff, T.; Dickschat, J. S.; Wickel, S.; Grunenberg, J.; Wagner-Döbler, I.; Simon, M.; Schulz, S. *Org. Biomol. Chem.* 2010, 8, 234. (d) Cane, D. E.; Wu, Z.; van Epp, J. E. *J. Am. Chem. Soc.* 1992, 114, 8479.

(6) (a) Siegel, D. A.; Franz, B. A. *Nature* 2010, 466, 569. (b) Marsh, M. E. *Biochem. Physiol. B Biochem. Mol. Biol.* 2003, 136, 743.

(7) (a) Everitt, D. A.; Wright, S. W.; Volkman, J. K; Thomas, D. P.; Lindstrom, E. J. *Deep Sea Res. A* 1990, 37, 975. (b) Balch, W. M.; Holligan, P. M.; Ackleson, S. G.; Voss, K. J. *Limnol. Oceanogr.* 1991, 36, 629. (c) Holligan, P. M.; Fernandez, E.; Aiken, J.; Balch, W. M.; Boyd, P.; Burkill, P. H.; Finch, M.; Groom, S. B.; Malin, G.; Muller, K.; Purdie, D. A.; Robinson, C.; Trees, C. C.; Turner, S. M.; van der Wal, P. *Global Biogeochem. Cycles* 1993, 7, 879.

(8) (a) Wolfe, G. V.; Steinke, M.; Kirst, G. O, *Nature* 1997, 387, 894. (b) Wolfe, G. V.; Steinke, M. *Limnol. Oceanogr.* 1996, 41, 1151.

(9) (a) Howard, E. C.; Henriksen, J. R.; Buchan, A.; Reisch, C. R.; Bürgmann, H.; Welsh, R.; Ye, W.; Gonzalez, J. M.; Mace, K.; Joye, S. B.; Kiene, R. P.; Whitman, W. B.; Moran, M. A. *Science* 2006, 314, 649. (b) Vila-Costa, M.; Simo, R.; Harada, H.; Gasol, J. M.; Slezak, D.; Kiene, R. P. *Science* 2006, 314, 652. (c) Seymour, J. R.; Simo, R.; Ahmed, T.; Stocker, R. *Science* 2010, 329, 342.

(10) Reisch, C. R.; Stoudemayer, M. J.; Varaljay, V. A.; Amster, I. H.; Moran, M. A.; Whitman, W. B. *Nature* 2011, 473, 208.

(11) (a) Charlson, R. J.; Lovelock, J. E.; Andreae, M. O.; Warren, S. G. *Nature* 1987, 326, 655. (b) Bates, T. S.; Carlson, R. J.; Gammon, R. H. *Nature* 1987, 329, 319.

(12) (a) Miller, T. R.; Belas, R. *Environ. Microbiol.* 2006, 8, 1648. (b) Kjelleberg, S.; Steinberg, P.; Givskov, M.; Gram, L.; Manefield, M.; de Nys, R. *Aquat. Microb. Ecol.* 1997, 13, 85. (c) Joint, I.; Tait, K.; Callow, M. E.; Callow, J. A.; Milton, D.; Williams, P.; Camara, M. *Science* 2002, 298, 1207. (d) Matsuo, Y.; Imagawa, H.; Nishizawa, M.; Shizuri, Y. *Science* 2005, 307, 1598. (e) Keshtacher-Liebso, E.; Hadar, Y.; Chen, Y. *Appl. Environ. Microbiol.* 1995, 61, 2439. (f) Rao, D.; Webb, J. S.; Holmstrom, C.; Case, R.; Low, A.; Steinberg, P.; Kjelleberg, S. *Appl. Environ. Microbiol.* 2007, 73, 7844. (g) Mayali, X.; Azam, F. *J. Eukaryot. Microbiol.* 2004, 51, 139.

(13) Gonzalez, J. M.; Simo, R.; Massana, R.; Covert, J. S.; Casamayor, E. 0.; Pedros-Alio, C.; Moran, M. A. *Appl. Environ. Microbiol.* 2000, 66, 4237.

(14) Schaefer, A. L.; Greenberg, E. P.; Oliver, C. M.; Oda, Y.; Huang, J. J.; Bittan-Banin, G.; Peres, C. M.; Schmidt, S.; Juhaszova, K.; Sufrin, J. R.; Harwood, C. S, *Nature* 2008, 454, 595.

(15) (a) Delwiche, C. F.; Graham, L. E.; Thomson, N. *Science* 1989, 245, 399. (b) Martone, P. T.; Estevez, J. M.; Lu, F.; Ruel, K.; Denny, M. W.; Somerville, C.; Ralph, J. *Curr. Biol.* 2009, 19, 169. (c) Espineira, J. M.; Novo Uzal, E.; Gomez Ros, L. V.; Carrion, J. S.; Merino, F.; Ros Barcelo, A.; Pomar, F. *Plant Biol.* 2011, 13, 59.

(16) Gonzalez, J. M.; Kiene, R. P.; Moran, M. A. *Appl. Environ. Microbiol.* 1999, 65, 3810.

(17) (a) Davin, L. B.; Jourdes, M.; Patten, A. M.; Kim, K. W.; Vassao, D. G.; Lewis, N. G. *Nat. Prod. Rep.* 2008, 25, 1015. (b) Bonawitz, N. D.; Chapple, C. *Annu. Rev. Genet.* 2010, 44, 337.

(18) (a) Delker, C.; Raschke, A.; Quint, M. Planta 2008, 227, 929. (b) Woodward, A. W.; Bartel, B. *Ann. Bot.* 2005, 95, 707. (c) Ashen, J. B.; Cohen, J. D.; Goff, L. J. *J. Phycol.* 1999, 35, 493.

(19) (a) Eichhorn, P.; Knepper, T. P. *Environ. Toxicol. Chem.* 2002, 21, 1. (b) Andreu, V.; Pico, Y. *Anal. Chem.* 2004, 76, 2878. (c) Lara-Martin, P. A.; Gomez-Parra, A.; Köchling, T.; Luis Sanz, J.; Mazo-Gonzalez, E. *Environ. Sci. Technol.* 2007, 41, 3580.

(20) Dickschat, J. S.; Zell, C.; Brock, N. L. *Chembiochem* 2010, 11, 417. (b) Geng, H.; Bruhn, J. B., Nielsen, K. F.; Gram, L.; Belas, R. *Appl. Environ. Microbiol.* 2008, 74, 1535

(21) Vandecandelaere, I.; Segaert, E.; Mollica, A.; Faimali, M.; Vandamme, P. *Int. J. syst. Evol. Microbiol.* 2008, 58, 2788.

(22) Lafay, B.; Ruimy, R.; Rausch de Traubenberg, C.; Breittmayer, V.; Gauthier, M. J.; Christen, R. *Int. J. Syst. Bacteriol.* 1995, 45, 290.

(23) Ashen, J. B.; Goff, L. J. *Appl. Environ. Microbiol.* 2000, 66, 3024.

(24) Initial bioassays against *E. huxleyi* show that 19 and 21 are potent antialgal compounds similar to 6 and 7.

TABLE 1

| X-ray diffraction data for Roseobacticide | |
|---|---|
| Chemical Formula | $C_{16}H_{16}O_5S$ |
| $M_r$ | 320.35 |
| Crystal system, space group | Monoclinic, Cc |
| Temperature (K) | 100 |
| a, b, c (Å) | 14.708 (12), 14.7655 (14), 7.1612 (9) |
| β (°) | 95.647 (10) |
| V (Å$^3$) | 1547.7 (13) |
| Z | 4 |
| Radiation type | Mo Kα |
| μ (mm$^{-1}$) | 0.23 |
| Crystal size (mm) | 0.20 × 0.03 × 0.02 |
| Data Collection | |
| Diffractometer | CCD area detector diffractometer |
| Absorption correction | MULTI-SCAN |
| | SADABS (Bruker, 2005) |
| $T_{min}$, $T_{max}$ | 0.956, 0.995 |
| No. of measured, independent and observed [1 > 2σ(1)] reflections | 7010, 1488, 1093 |
| $R_{int}$ | 0.065 |

TABLE 1-continued

X-ray diffraction data for Roseobacticide

| | Refinement |
|---|---|
| $R[F^2 > 2\sigma(F^2)]$, $wR(F^2)$, S | 0.078, 0.219, 1.18 |
| No. of reflections | 1488 |
| No. of parameters | 205 |
| No. of restraints | 2 |
| H-atom treatment | H-atom parameters constrained |
| $\Delta\rho_{max}$, $\Delta\rho_{min}$ (e Å$^{-3}$) | 1.31, −0.32 |
| Absolute Structure | Flack H D (1983), Acta Cryst. A39, 876-881 |
| Flack parameter | 0 (10) |

X-ray diffraction data was collected by Dr. Shao-Liang Zheng at the Center for Crystallographic Studies, Harvard University. Computer programs used: APEX II (Bruker, 2007), Bruker Saint v7.23A (Bruker, 2005), SHELXS97 (Sheldrick, 1997), SHELXL97 (Sheldrick, 1997), Bruker SHELXTL.

TABLE 2

NMR spectral data for Roseobacticide A. The structure of Roseobacticide A is shown FIG. 2.

| C/H | $\delta_H$ | Multiplicity (Hz) | $\delta_C$ | HMBC |
|---|---|---|---|---|
| 2 | | | 169.7 | |
| 3 | | | 110.2 | |
| 4 | 7.37 | d (11.4) | 121.6 | C3, C6, C9, C10 |
| 5 | 7.0 | dd (9.3, 11.4) | 133.8 | C7, C10 |
| 6 | 6.64 | dd (1.7, 9.3) | 122.5 | C4, C7, C8 |
| 7 | | | 147.2 | |
| 7-CH$_3$ | 2.61 | s | 15.1 | C7 |
| 8 | 6.89 | d (1.7) | 112.6 | C6, C9, C10 |
| 9 | | | 155.0 | |
| 10 | | | 144.0 | |
| 11 | | | 121.4 | |
| 12/16 | 7.55 | m | 129.8 | C11, C14 |
| 13/15 | 6.99 | m | 115.7 | C11, C14 |
| 14 | | | 157.5 | |

TABLE 3

NMR spectral data for Roseobacticide B. The structure of Roseobacticide B is shown FIG. 2.

| C/H | $\delta_H$ | Multiplicity (Hz) | $\delta_C$ |
|---|---|---|---|
| 2 | | | |
| 3 | | | |
| 4 | 7.41 | d (11.3) | 121.5 |
| 5 | 7.05 | dd (9.3, 11.4) | 134.1 |
| 6 | 6.70 | dd (1.6, 9.4) | 122.8 |
| 7 | | | |
| 7-CH$_3$ | 2.60 | s | 15.2 |
| 8 | 6.98 | d (1.8) | 113.3 |
| 9 | | | |
| 10 | | | |
| 11 | | | |
| 12/16 | 7.48 | m | 128.6 |
| 13/15 | 7.66 | m | 128.1 |
| 14 | 7.36 | m | 128.5 |

TABLE 4

Half-maximal inhibitory concentrations (IC50) of Roseobacticide A and B against selected bacterial and algal strains.

| Strain | Phaeobacticide | IC$_{50}$ (µM) |
|---|---|---|
| *Phaeobacter gallaeciensis* BS107 | A | >160 |
| *Phaeobacter gallaeciensis* 2.10 | A | >160 |
| *Silicibacter pomeroyi* DSS3 | A | >160 |
| *Reugeria* sp. R11 | A | >160 |
| *Silicibacter* sp. TM1040 | A | >160 |
| *Bacillus subtilis* 3610 | A | >160 |
| *Vibrio anguillarum* | A | >160 |
| *Pseudoalteromonas tunicata* D2 | A | >160 |
| *Emiliana huxleyi* CCMP372 | A | ≥2.2 |
| *Emiliana huxleyi* CCMP372 | B | 0.19 |
| *Rhodomonas salina* CCMP1319 | A | 0.10 |
| *Chaetoceros muelleri* CCMP1318 | A | >35 |
| *Tetraselmis suecica* CCMP908 | A | >35 |
| *Isochrysis* sp. CCMP468 | A | >35 |

TABLE 5

Detection of homologs of characterized lignin biosynthesis proteins in *E. huxleyi*

| Enzyme abbreviation | *E. huxleyi* best genome hit | E-value | Homologous |
|---|---|---|---|
| Cinnamyl alcohol dehydrogenase (CAD) | jgi\|Emihu1\|43159\|gw1.323.6.1 | 9e−41 | Yes |
| Caffeoyl-CoA 3-O-methyltransferase (CCoAOMT) | jgi\|Emihu1\|352029\|fgenesh_newKGs_kg.14_73_2694629:1 | 2e−32 | Yes |
| 4-Coumarate:CoA ligase (4CL) | jgi\|Emihu1\|262351\|estExt_Genewise1Plus.C_410082 | 2e−68 | Yes |
| Cinnamoyl-CoA reductase (CCR) | jgi\|Emihu1\|73363\|e_gw1.228.24.1 | 2e−30 | Yes |
| Phenylalanine ammonia lyase (PAL)[a] | jgi\|Emihu1\|69043\|e_gw1.92.6.1 | 4e−39 | Yes |
| Trans-cinnamate 4-hydroxylase (C4H) | jgi\|Emihu1\|262351\|estExt_Genewise1Plus.C_410082 | 2e−63 | Yes |
| Hydroxycinnamoyl-CoA:shikimate/quinate hydroxycinnamoyltransferase (HCT) | None | NA | No |
| Caffeic acid O-methyltransferase (COMT)[b] | jgi\|Emihu1\|95632\|fgeneshEH_pg.3_307 | 1e−17 | No |
| p-Coumarate 3-hydroxylase (C3H)[c] | jgi\|Emihu1\|236829\|gm1.24100017 | 1e−17 | No |
| Ferulate 5-hydroxylase (F5H)[c] | jgi\|Emihu1\|274974\|estExt_Genemark1.C_10105 | 1e−12 | No |

[a] Reciprocal hit to *A. thaliana* of the *E. huxleyi* gene is an histidine ammonia lyase, not a phenylalanine ammonia lyase. These two enzymes are part of the same family and could accept multiple substrates.

[b] Reciprocal hit to *A. thaliana* is a general O-methyltransferase family protein, not the biochemically characterized COMT

[c] Reciprocal hit to *A. thaliana* is a general cytochrome P450 protein, not the biochemically characterized C3H or F5H

TABLE 6

Amount of roseobacticides (mg/L) produced by *P. gallaciensis* BS107 and 2.10 as a function of elicitor.

| Roseobacticides | 14 | 15 | 16 | 17 |
|---|---|---|---|---|
| BS107[a] | | | | |
| A | 0.29 | 0.08 | 0.2 | 0.04 |
| B | 0.11 | 1.1 | 0.5 | 0.2 |
| C | 0.29 | 0.45 | 0.25 | — |
| D | 0.1 | 0.09 | — | — |
| E | 0.18 | 0.47 | 0.2 | — |
| F | 0.15 | 0.19 | — | — |
| G | —[b] | 0.13 | — | — |
| H | 0.2 | 0.12 | — | — |
| I | 0.06 | — | — | — |
| J | 0.06 | 0.15 | 0.1 | — |
| K | — | 0.012[c] | — | — |
| 2.10[d] | | | | |
| A | 0.04 | —[b] | — | — |
| B | 0.08 | 0.21 | 0.7 | 0.26 |
| H | 0.1 | — | — | 0.08 |
| I | 0.06 | — | 0.17 | 0.16 |

[a]Values are averages from three (14, 15) or two (16, 17) independent isolations from large-scale cultures. Standard deviations ranged from 5-40%
[b]Denotes amounts below 0.04 mg/L.
[c]An estimate from HPLC-MS comparisons with (26).
[d]Values are averages from two independent experiments from small-scale cultures and comparison with known amounts of roseobacticides. Not that, unlike the data for *P. galaeciensis* BS107, these are not isolation yields. Standard deviations ranged from 10-35%.

TABLE 7

HR-MS results for roseobacticides C-K.

| Roseobacticide | [M + H]⁺calc | [M + H]⁺expt | Formula | Δppm |
|---|---|---|---|---|
| C | 308.0745 | 308.0738 | $C_{18}H_{13}NO_2S$ | 2.3 |
| D | 317.0307 | 317.0306 | $C_{16}H_{12}O_3S_2$ | 0.3 |
| E | 301.0358 | 301.0365 | $C_{16}H_{12}O_2S_2$ | 2.3 |
| F | 340.0467 | 340.0456 | $C_{18}H_{13}NO_2S_2$ | 3.2 |
| G | 363.0892 | 363.0698 | $C_{21}H_{14}O_4S$ | 1.7 |
| H | 347.0743 | 347.0747 | $C_{21}H_{14}O_3S$ | 1.2 |
| I | 303.0327 | 303.0316 | $C_{15}H_{10}O_5S$ | 3.6 |
| J | 507.0725 | 507.0736 | $C_{30}H_{18}O_4S_2$ | 2.2 |
| K | 523.0674 | 523.0692 | $C_{30}H_{18}O_5S_2$ | 3.4 |

TABLE 8

Selected Tandem HR-MS fragments for roseobacticides C-K.[a]

| Roseobacticide | Fragment lost | [M + H]⁺calc | [M + H]⁺expt | Δppm |
|---|---|---|---|---|
| C | —CO | 280.0784 | 280.0796 | 4.3 |
| C | —CH₃S | 260.0712 | 260.0700 | 4.6 |
| C | —CO/CH₃S | 233.0841 | 233.0838 | 1.3 |
| D | —CH₃ | 302.0071 | 302.0064 | 2.3 |
| D | —CO | 289.0357 | 289.0345 | 4.2 |
| D | —CH₃S | 270.0351 | 270.0341 | 3.7 |
| D | —CO/CH₃S | 242.0402 | 242.0404 | 0.8 |
| E | —CH₃ | 286.0117 | 286.0163 | 16 |
| E | —CH₃S | 254.0396 | 254.0436 | 16 |
| E | —CO | 226.0447 | 226.0476 | 13 |
| E | —CH₃S—S | 222.0675 | 222.0699 | 11 |
| F | —CH₃ | 325.0231 | 325.0245 | 4.3 |
| F | —CH₃S | 293.0510 | 293.0515 | 1.7 |
| F | —CH₃S—S | 261.0790 | 261.0784 | 2.3 |
| G | —CO | 275.0378 | 275.0331 | 17 |
| G | —CO/SO₃H | 194.0732 | 194.0722 | 5.2 |
| G[b] | —SO₂ | 237.0552 | 237.0553 | 0.4 |
| G[b] | —SO₂/CO | 209.0603 | 209.0592 | 5.2 |
| H | —CO | 335.0742 | 335.0752 | 3.0 |
| H | -p-OH-benzene-S— | 238.0630 | 238.0621 | 3.8 |
| H | -p-OH-benzene-S—/CO | 210.0681 | 210.0669 | 5.7 |
| H[b] | -(3-phenol)-1-oxoazulan-2-one | 123.9983 | 123.9989 | 4.8 |
| I | —CO | 319.0793 | 319.0797 | 1.3 |
| I | -p-OH-benzene-S | 222.0682 | 222.0673 | 4.1 |
| I[b] | -(3-phenyl)-1-oxoazulan-2-one | 123.9983 | 123.9987 | 3.2 |
| J | −21[c] | 254.0402 | 254.0398 | 1.6 |
| K | −21[c] | 270.0351 | 270.0383 | 12 |
| K | −22[c] | 254.0402 | 254.0420 | 7.1 |

[a]Tandem HR-MS was calibrated to within 12 ppm. Unless noted otherwise, spectra were collected in the positive ion mode.
[b]HR-MS spectra obtained in the negative ion mode.
[c]These fragments were generated by cleavage of the disulfide bond. See FIG. 18 for structures of 28 and 29.

TABLE 9

NMR data for roseobacticide C in acetone-$d_6$.

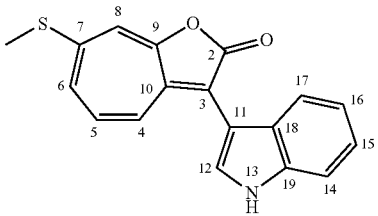

| C/H | $\delta_H$ | Multiplicity (Hz) | $\delta_C$ | COSY | HMBC |
|---|---|---|---|---|---|
| 3 | | | | | |
| 4 | 7.15 | d, 11.4 | 122.8 | H5 | C9 |
| 5 | 6.89 | dd, 11.4, 9.1 | 132.4 | H4, H6 | |
| 6 | 6.55 | dd, 9.2, 1.7 | 121.6 | H5, H8 | C8 |
| 7 | | | | | |
| 7-methyl | 2.58 | s | 15.1 | | |
| 8 | 6.80 | d, 1.8 | 111.7 | H6 | |
| 9 | | | 155.0 | | |
| 10 | | | | | |
| 11 | | | 105.5 | | |
| 12 | 7.69 | d, 2.6 | 125.8 | H13 | C11 |
| 13 | | | | | |
| 14 | 7.52 | d, 8.1 | 112.0 | H15 | |
| 15 | 7.19 | ddd, 8.1, 7.1, 1.0 | 122.0 | H14, H16, H17 | C19 |
| 16 | 7.10 | ddd, 8.1, 7.0, 1.1 | 119.5 | H14, H15, H17 | C18 |
| 17 | 7.54 | d, 8.1 | 121.3 | H16 | C19 |
| 18 | | | 125.6 | | |
| 19 | | | 136.8 | | |

TABLE 10

NMR data for roseobacticide D in acetone-$d_6$.

| C/H | $\delta_H$ | Multiplicity (Hz) | $\delta_C$ | COSY | HMBC |
|---|---|---|---|---|---|
| 3 | | | 111.1 | | |
| 4 | 7.46 | d, 11.4 | 124.4 | H5 | C9 |
| 5 | 7.01 | dd, 11.4, 9.4 | 135.3 | H4, H6 | C10 |
| 6 | 7.12 | overlap | 125.3 | H5, H8 | C4, C8 |
| 7 | | | | | |
| 7-methyl | 2.55 | s | 22.2 | | |
| 8 | 7.12 | overlap | 110.6 | H6 | C6, C9 |
| 9 | | | 156.1 | | |
| 10 | | | 144.1 | | |
| 11 | | | 121.6 | | |
| 12/16 | 7.52 | d, 8.6 | 129.7 | H13/15 | C3, C14 |
| 13/15 | 6.96 | d, 8.7 | 115.6 | H12/16 | C11, C14 |
| 14 | | | 157.5 | | |

TABLE 11

NMR data for roseobacticide E in acetone-$d_6$.

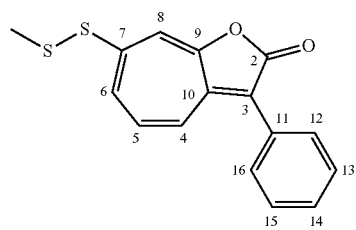

| C/H | $\delta_H$ | Multiplicity (Hz) | $\delta_C$ | COSY | HMBC |
|---|---|---|---|---|---|
| 3 | | | | | |
| 4 | 7.45 | d, 11.4 | 124.2 | H5 | |
| 5 | 6.92 | dd, 11.4, 9.2 | 133.4 | H4, H6 | |
| 6 | 7.10 | dd, 9.8, 1.6 | 125.0 | H5, H8 | |
| 7 | | | | | |
| 7-methyl | 2.50 | s | 23.2 | | |
| 8 | 7.22 | d, 1.8 | 111.9 | | |
| 9 | | | | | |
| 10 | | | | | |
| 11 | | | | | |
| 12/16 | 7.63 | m | 128.5 | H13/15 | |
| 13/15 | 7.49 | m | 128.9 | H12/16, H14 | |
| 14 | 7.40 | m | 128.2 | H13/15 | |

TABLE 12

NMR data for roseobacticide F in acetone-$d_6$.

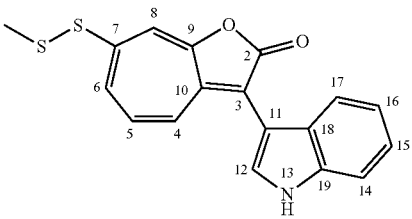

| C/H | $\delta_H$ | Multiplicity (Hz) | $\delta_C$ | COSY | HMBC |
|---|---|---|---|---|---|
| 3 | | | | | |
| 4 | 7.29 | d, 11.4 | 125.5 | H5 | |
| 5 | 6.94 | dd, 1.4, 9.0 | 131.8 | H4, H6 | C10 |
| 6 | 7.07 | overlap | 124.6 | H5, H8 | |
| 7 | | | | | |
| 7-methyl | 2.56 | s | 22.2 | | |
| 8 | 7.06 | overlap | 109.8 | H6 | |
| 9 | | | | | |
| 10 | | | 143.5 | | |
| 11 | | | 105.1 | | |
| 12 | 7.73 | d, 2.6 | 126.0 | H13 | |
| 13 | | | | | |
| 14 | 7.53 | d, 8.2 | 112.0 | H15 | C16 |
| 15 | 7.20 | ddd, 8.0, 7.1, 1.0 | 122.1 | H14, H16, H17 | C17, C19 |
| 16 | 7.11, | ddd, 8.0, 7.1, 1.0 | 119.8 | H14, H15, H17 | C14, C18 |
| 17 | 7.54 | d, 8.1 | 121.0 | H16 | C11 |
| 18 | | | 126.2 | | |
| 19 | | | 136.4 | | |

TABLE 13

NMR data for roseobacticide G in acetone-$d_6$.

| C/H | $\delta_H$ | Multiplicity (Hz) | $\delta_C$ | COSY | HMBC |
|---|---|---|---|---|---|
| 3 | | | | | |
| 4 | 7.66 | d, 11.5 | 130.9 | H5 | |
| 5 | 7.13 | dd, 11.5, 8.9 | 133.3 | H4, H6 | |
| 6 | 7.60 | overlap | 130.6 | H5, H8 | C4, C8 |
| 7 | | | 132.4 | | |
| 8 | 7.47 | d, 1.6 | 113.7 | H | C7 |
| 9 | | | | | |
| 10 | | | | | |
| 11 | | | | | |
| 12/16 | 7.61 | m | 130.5 | H13/15 | |
| 13/15 | 7.49 | m | 130.9 | H12/16, H14 | |
| 14 | 7.39 | m | 130.8 | H13/15 | |

TABLE 14

NMR data for roseobacticide H in acetone-$d_6$.

| C/H | $\delta_H$ | Multiplicity (Hz) | $\delta_C$ | COSY | HMBC |
|---|---|---|---|---|---|
| 3 | | | 110.6 | | |
| 4 | 7.32 | d, 11.5 | 122.6 | H5 | C6, C9 |
| 5 | 6.85 | dd, 11.5, 9.3 | 133.6 | H4, H6 | C7, C10 |
| 6 | 6.42 | dd, 9.3, 1,5 | 124.6 | H5, H8 | C4, C7, C8 |
| 7 | | | 148.4 | | |
| 8 | 6.74 | d, 1.8 | 112.0 | H6 | C6, C9, C10 |
| 9 | | | 156.2 | | |
| 10 | | | 144.9 | | |
| 11 | | | 121.8 | | |
| 12/16 | 7.50 | d, 8.8 | 129.8 | H13/15 | C3, C14 |
| 13/15 | 6.94 | d, 8.8 | 115.5 | H12/16 | C11, C14 |
| 14 | | | 157.7 | | |
| 17 | | | | | |
| 18/22 | 7.45 | dd, 8.7, 1.1 | 137.7 | H19/21 | C19/21, C20 |
| 19/21 | 7.01 | d, 8.7 | 117.3 | H18/22 | C20 |
| 20 | | | 160.6 | | |

TABLE 15

NMR data for roseobacticide I in acetone-$d_6$.

| C/H | $\delta_H$ | Multiplicity (Hz) | $\delta_C$ | COSY | HMBC |
|---|---|---|---|---|---|
| 3 | | | 109.2 | | |
| 4 | 7.40 | d, 11.4 | 122.1 | H5 | C6, C9 |
| 5 | 6.95 | dd, 11.4, 9.4 | 130.8 | H4, H6 | C7, C10 |
| 6 | 6.51 | dd, 9.3, 1.8 | 124.6 | H5, H8 | C4, C7, C8 |
| 7 | | | 148.3 | | |
| 8 | 6.86 | d, 1.8 | 112.1 | H6 | C6, C9, C10 |
| 9 | | | 155.5 | | |
| 10 | | | 145.3 | | |
| 11 | | | 130.5 | | |
| 12/16 | 7.65 | m | 128.0 | H13/15 | C3, C14 |
| 13/15 | 7.47 | m | 128.3 | H12/16, H14 | C11 |
| 14 | 7.37 | m | 127.6 | H13/15 | C12/16 |
| 17 | | | | | |
| 18/22 | 7.45 | d, 8.6 | 137.2 | H19/21 | C20 |
| 19/21 | 7.02 | d, 8.7 | 117.3 | H18/22 | |
| 20 | | | 159.5 | | |

TABLE 16

NMR data for roseobacticide J in acetone-$d_6$.

| C/H | $\delta_H$ | Multiplicity (Hz) | $\delta_C$ | COSY | HMBC |
|---|---|---|---|---|---|
| 3 | | | | | |
| 4 | 7.41 | d, 11.4 | 125.5 | H5 | |
| 5 | 7.00 | dd, 11.3, 9.3 | 132.6 | H4, H6 | |
| 6 | 7.19 | d, 9.3 | 127.6 | H5 | |
| 7 | | | | | |
| 8 | 7.30 | s | 112.1 | | |
| 9 | | | | | |
| 10 | | | | | |
| 11 | | | | | |
| 12/16 | 7.60 | t, 7.5 | 127.9 | H13/15 | |
| 13/15 | 7.47 | t, 7.5 | 128.3 | H12/16, H14 | |
| 14 | 7.38 | t, 7.3 | 128.1 | H13/15 | |

What is claimed:

1. The algicide formulation comprising a compound comprising the formula:

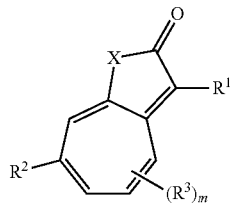

FORMULA (I)

or a salt thereof, and an algicide, a herbicide, a bactericide or a fungicide,
wherein $R^1$ is optionally substituted aryl, optionally substituted heteroaryl, optionally substituted phenyl or an optionally substitute indole;
wherein $R^2$ is $OR^7$, $SR^7$, $SO_2R^7$, or $SSR^7$;
wherein $R^7$ is H, methyl, ethyl, propyl, butyl, pentyl, hexyl, optionally substituted alkyl, optionally substituted alkenyl, optionally substituted alkynyl, optionally substituted acyl, optionally substituted arylcarbonyl, optionally substituted aryl or formula (I);
wherein m is 0, 1, 2, 3, or 4, and
wherein $R^3$ is $OR^6$, $SR^6$, $SSR^6$, halogen, CN, $N(R^6)_2$, $NO_2$, optionally substituted alkyl, optionally substituted alkenyl, or optionally substituted alkynyl;
wherein $R^6$ is H, methyl, ethyl, propyl, butyl, pentyl, hexyl, optionally substituted alkyl, optionally substituted alkenyl, optionally substituted alkynyl, optionally substituted acyl;
and wherein X is O, S, $NR^6$.

2. A method of controlling algal growth in a body of water, the method comprising adding to the water a sufficient amount of a an algicide formulation of claim 1,
wherein the body of water is selected from the group consisting of swimming pools, aquaculture ponds, freshwater ponds, aquariums, urban drainage systems and industrial cooling water systems.

3. A material or industrial product selected from the group consisting of paints, polyvinyl chloride-containing plastics, varnishes, sealing materials, textile finishes, synthetic resin rendering, wood finishes and coatings, and roof tile coatings comprising a composition or formulation comprising the formula:

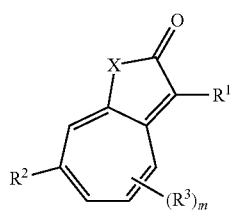

FORMULA (I)

or a salt thereof to kill, inhibit or prevent growth of algae growth,
wherein $R^1$ is optionally substituted aryl, optionally substituted heteroaryl, optionally substituted phenyl or an optionally substitute indole;
wherein $R^2$ is $OR^7$, $SR^7$, $SO_2R^7$, or $SSR^7$;
wherein $R^7$ is H, methyl, ethyl, propyl, butyl, pentyl, hexyl, optionally substituted alkyl, optionally substituted alkenyl, optionally substituted alkynyl, optionally substituted acyl, optionally substituted arylcarbonyl, optionally substituted aryl or formula (I);
wherein m is 0, 1, 2, 3, or 4, and
wherein $R^3$ is $OR^6$, $SR^6$, $SSR^6$, halogen, CN, $N(R^6)_2$, $NO_2$, optionally substituted alkyl, optionally substituted alkenyl, or optionally substituted alkynyl;
wherein $R^6$ is H, methyl, ethyl, propyl, butyl, pentyl, hexyl, optionally substituted alkyl, optionally substituted alkenyl, optionally substituted alkynyl, optionally substituted acyl;
wherein X is O, S, $NR^6$,
wherein the composition or formulation is applied thereon or is incorporated within.

4. The composition of claim 1, wherein the $R^1$ optionally substituted phenyl is

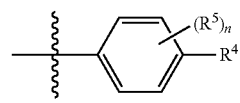

wherein $R^4$ is H, $OR^6$, $SR^6$, halogen, CN, $CF_3$, $N(R^6)_2$, $NO_2$, optionally substituted alkyl, optionally substituted alkenyl, or optionally substituted alkynyl;
n is 0, 1, 2, 3, or 4; and
$R^5$ is $OR^6$, $SR^6$, $SSR^6$, halogen, CN, $CF_3$, $N(R^6)_2$, $NO_2$, optionally substituted alkyl, optionally substituted alkenyl, or optionally substituted alkynyl.

5. The composition of claim 4, wherein $R^4$ is H or $OR^6$.

6. The composition of claim 4, wherein $R^4$ is H, OH, or OMe.

7. The composition of claim 4, wherein $R^4$ is

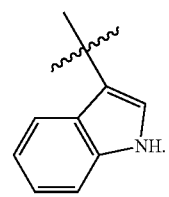 [SMILES: *c1c[nH]c2ccccc12]

8. The composition of claim 1, wherein $R^7$ is

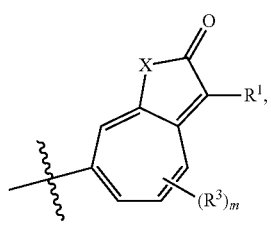

wherein the $R^1$, $R^3$, and X are as defined for formula (I).

9. The composition of claim 1, wherein the $R^7$ optionally substituted arylcarbonyl is

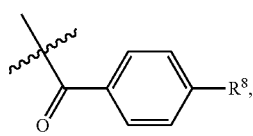

wherein $R^8$ is H, $OR^6$, $SR^6$, halogen, CN, $CF_3$, $N(R^6)_2$, $NO_2$, optionally substituted alkyl, optionally substituted alkenyl, or optionally substituted alkynyl.

10. The composition of claim 1, wherein m is 1 and $R^3$ is OH, SH, or SSH.

11. The composition of claim 1, wherein X is O.

12. The composition of claim 1, wherein the compound is selected from the group consisting of:

Roseobacticide A
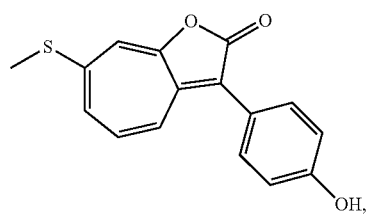

Roseobacticide B
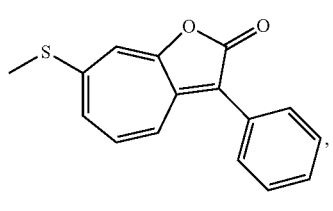

Roseobacticide C
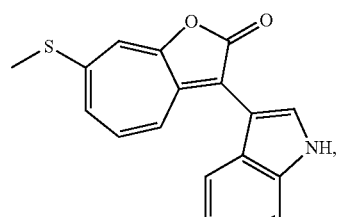

Roseobacticide D
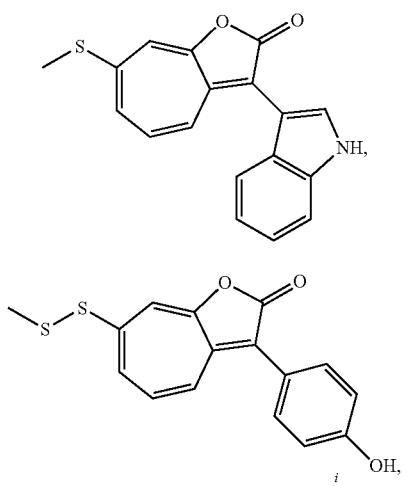

Roseobacticide E
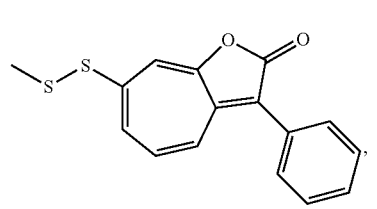

-continued

Roseobacticide F
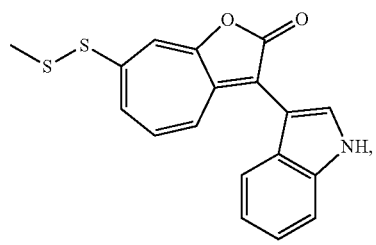

Roseobacticide G
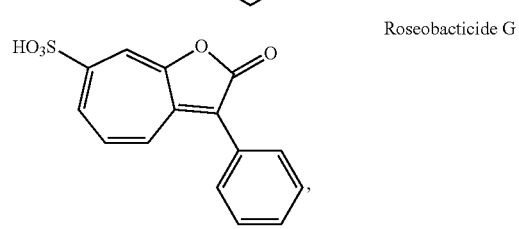

Roseobacticide H
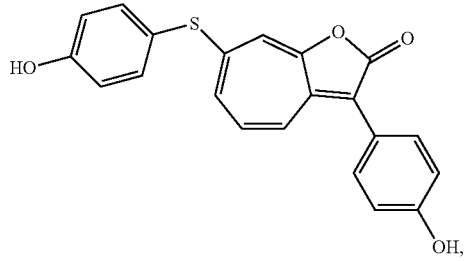

Roseobacticide I
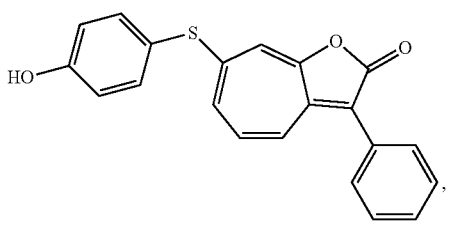

Roseobacticide J
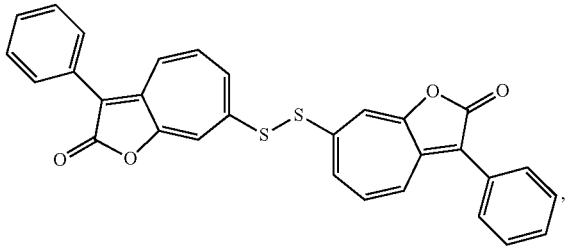

Roseobacticide K
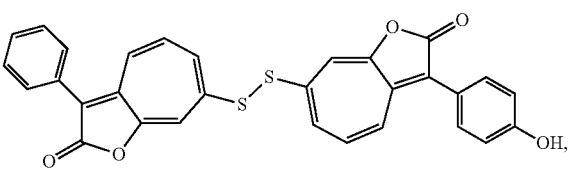

Roseobacticide L
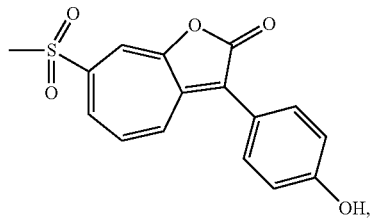
Roseobacticide M
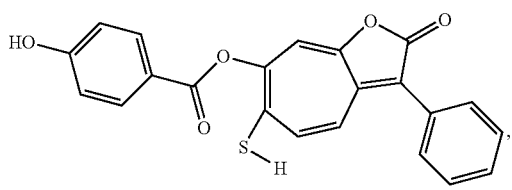
Roseobacticide N
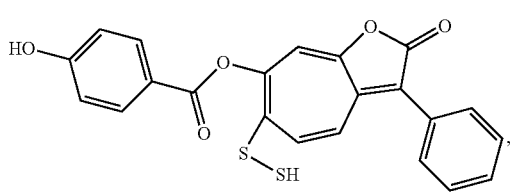
Roseobacticide O
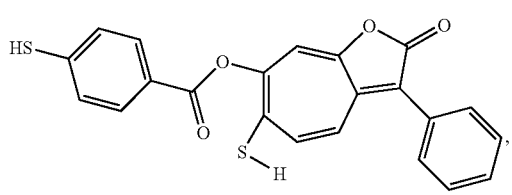
Roseobacticide P
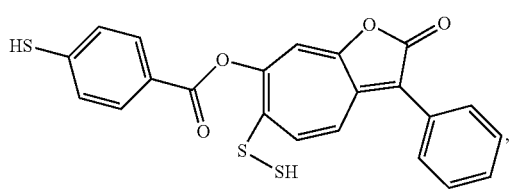
Roseobacticide Q
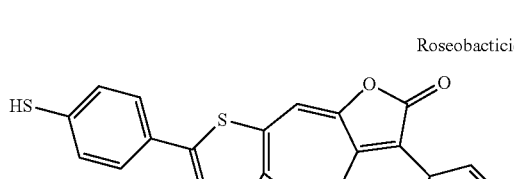
Roseobacticide R
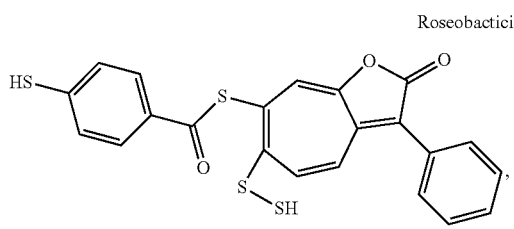
Roseobacticide S
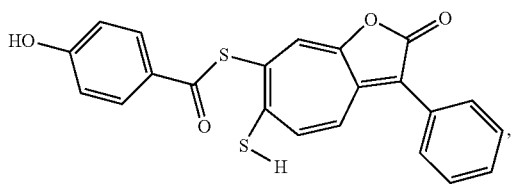
Roseobacticide T
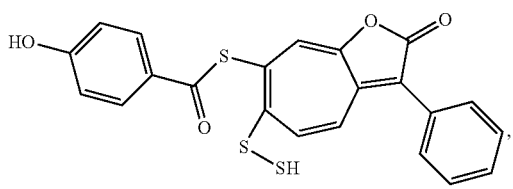
Roseobacticide U
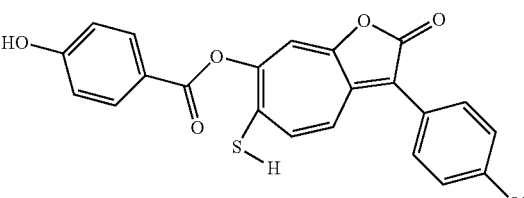
Roseobacticide V
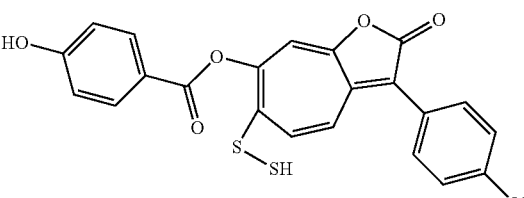
Roseobacticide W
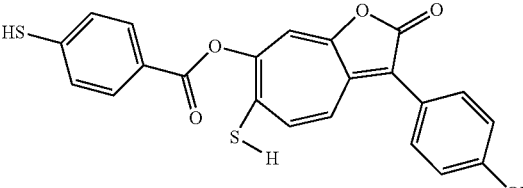
Roseobacticide X
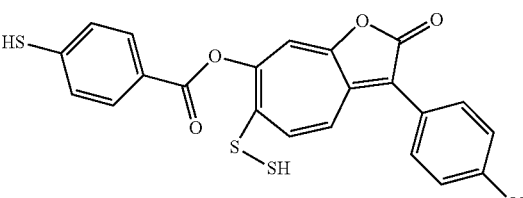

Roseobacticide Y

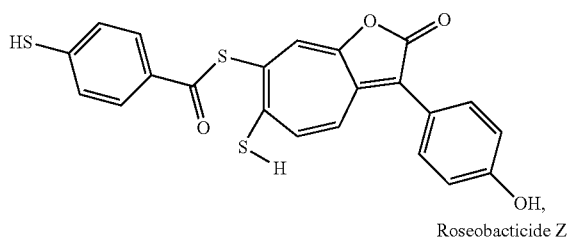

Roseobacticide Z

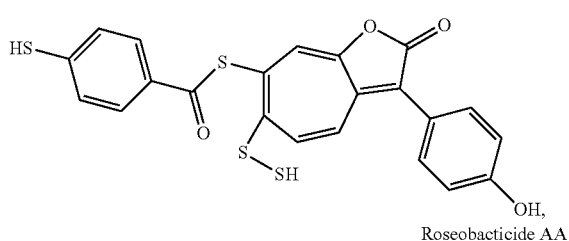

Roseobacticide AA

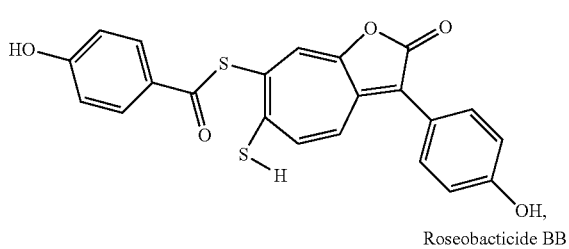

Roseobacticide BB

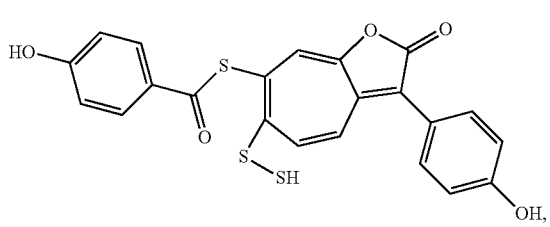

Roseobacticide CC

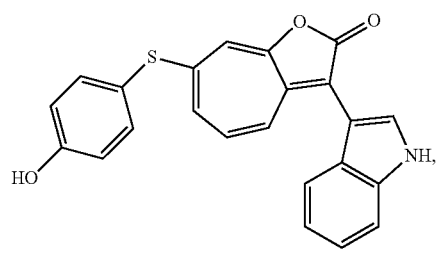

Roseobacticide DD

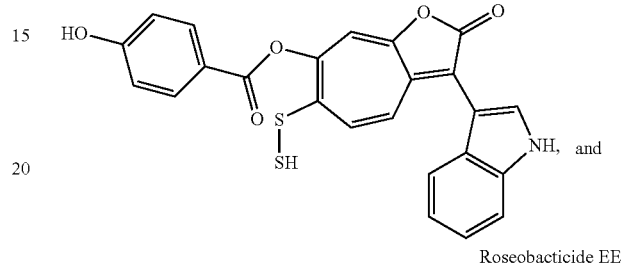

Roseobacticide EE

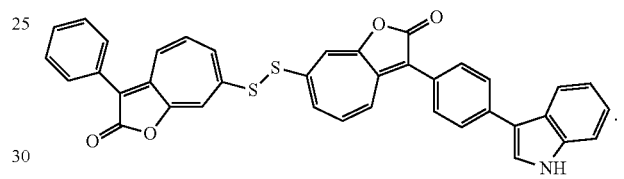

13. The composition of claim 1, wherein the compound has algicidal activity.

14. The composition of claim 13, wherein the algicidal activity has an $LC_{50}$ of 0.01 μM to 35 μM.

15. The composition of claim 13, wherein the algicide composition specifically kills the algae *Emiliana huxleyi*.

* * * * *